(12) United States Patent
Tai et al.

(10) Patent No.: US 7,976,779 B2
(45) Date of Patent: Jul. 12, 2011

(54) INTEGRATED LC-ESI ON A CHIP

(75) Inventors: Yu-Chong Tai, Pasadena, CA (US); Jun Xie, Pasadena, CA (US); Jason Shih, Yorba Linda, CA (US); Terry Lee, San Dimas, CA (US); Yunan Miao, Duarte, CA (US)

(73) Assignees: California Institute of Technology, Pasadena, CA (US); City of Hope, Duarte, CA (US)

( * ) Notice: Subject to any disclaimer, the term of this patent is extended or adjusted under 35 U.S.C. 154(b) by 1408 days.

(21) Appl. No.: 11/177,505

(22) Filed: Jul. 11, 2005

(65) Prior Publication Data
US 2006/0193748 A1    Aug. 31, 2006

Related U.S. Application Data

(63) Continuation-in-part of application No. 10/603,573, filed on Jun. 24, 2003, now abandoned.

(60) Provisional application No. 60/586,576, filed on Jul. 9, 2004, provisional application No. 60/391,822, filed on Jun. 26, 2002.

(51) Int. Cl.
*B01L 3/00* (2006.01)
*G01N 30/02* (2006.01)
*F04F 99/00* (2009.01)
*C02F 11/00* (2006.01)
*C02F 1/469* (2006.01)

(52) U.S. Cl. ............ 422/70; 422/505; 417/48; 204/600; 204/450

(58) Field of Classification Search .................. 422/505, 422/70; 417/48; 204/600, 450
See application file for complete search history.

(56) References Cited

U.S. PATENT DOCUMENTS
4,402,817 A    9/1983    Maget
(Continued)

OTHER PUBLICATIONS

Arscott, et al., "A planar on-chip micro-nib interface for NanoESI-MS microfluidic applications", J. Micromech. Microeng., vol. 14, pp. 310-316 (2004).

(Continued)

*Primary Examiner* — Lore Jarrett
(74) *Attorney, Agent, or Firm* — Foley & Lardner LLP

(57) ABSTRACT

A microfluidic system with on-chip pumping which can be used for liquid chromatography and also electrospray ionization mass spectrometry and which provides improved efficiency, better integration with sensors, improved portability, reduced power consumption, and reduced cost. The system can include (A) a main chip comprising: a substrate having a front face and a back face; a chromatography column on the front face of said substrate, wherein said column has an inlet and an outlet; an electrospray ionization (ESI) nozzle on the front face of said substrate, wherein said nozzle has an inlet and an outlet, and wherein the inlet of the nozzle is microfluidically coupled to the outlet of the column; one or more pump systems on the front face of said substrate comprising a pump chamber, one or more electrodes, and an outlet microfluidically coupled to the inlet of said column; and (B) a reservoir chip comprising a front surface and a back surface, wherein the reservoir chip has one or more cavities in the back surface which when disposed next to the front surface of the main chip extends the volume of the pump chamber of one of the pump system. Microfabrication can be used to prepare the chips, which can be assembled with a cover and inserted into a testing jig for electronic control and mass spectral analysis. Peptide separations are demonstrated which compete with present commercial systems.

13 Claims, 35 Drawing Sheets

Chip packaging after beads packing and fluid filling.

U.S. PATENT DOCUMENTS

| | | | |
|---|---|---|---|
| 4,687,423 | A | 8/1987 | Maget et al. |
| 5,994,696 | A | 11/1999 | Tai et al. |
| 6,162,367 | A | 12/2000 | Tai et al. |
| 6,193,866 | B1* | 2/2001 | Bader et al. .................. 204/450 |
| 6,245,227 | B1* | 6/2001 | Moon et al. ................ 210/198.2 |
| 6,352,838 | B1* | 3/2002 | Krulevitch et al. ............. 435/34 |
| 6,436,229 | B2 | 8/2002 | Tai et al. |
| 6,572,749 | B1 | 6/2003 | Paul et al. |
| 2003/0228411 | A1 | 12/2003 | Tai et al. |
| 2004/0124085 | A1 | 7/2004 | Tai et al. |
| 2004/0188648 | A1 | 9/2004 | Xie et al. |
| 2004/0208751 | A1* | 10/2004 | Lazar et al. ..................... 417/48 |
| 2004/0237657 | A1 | 12/2004 | Xie et al. |
| 2005/0051489 | A1 | 3/2005 | Tai et al. |
| 2009/0084685 | A1* | 4/2009 | Tai et al. ....................... 205/775 |

OTHER PUBLICATIONS

U.S. Appl. No. 09/442,843, filed Nov. 18, 1999, Tai et al.
U.S. Appl. No. 11/059,625, filed Feb. 17, 2005, Tai et al.
U.S. Appl. No. 11/192,434, filed Jul. 29, 2005, Tai et al.
U.S. Appl. No. 60/663,181, filed Mar. 18, 2005, Xie et al.
U.S. Appl. No. 60/671,309, filed Apr. 14, 2005, Xie et al.
Böhm, et al., "A closed-loop controlled electronchemically actuated micro-doesing system," J. Micromech., Microeng. vol. 10, pp. 498-504 (2000).
Cameron, et al., "Electrolytic actuators: Alterantive, high performance, material-based devices," PNAS, vol. 99, No. 12, pp. 7827-7831 (Jun. 11, 2002).
Chen, et al., "A Planar Electroosmotic Micropump," Journal of Microelectromechanical Systems, vol. 11, No. 6, pp. 672-683 (Dec. 2002).
Chen, et al., "Generating high-pressure sub-microliter flow rate in packed microchannel by electroosmotic force: potential application in microfluidic systems," Sensors and Actuators B 88, pp. 260-265 (2003).
Culbertson, et al., "Microchip Devices for High-Efficiency Separations", Anal. Chem., vol. 72, pp. 5814-5819 (2000).
Dasgupta, et al., "Electroosmosis: A Reliable Fluid Propulsion System for Flow Injection Analysis," Analytical Chemistry, vol. 66, No. 11, pp. 1792-1798 (Jun. 1, 1994).
Ekström, et al., "On-chip microextraction for proteomic sample preparation of in-gel digests", Proteomics, vol. 2, pp. 413-421 (2002).
Fortier, et al., "Integrated Microfluidic Device for Mass Spectrometry-Based Proteomics and Its Application to Biomarker Discovery Programs", Anal. Chem., vol. 77, pp. 1631-1640 (20005).
Gottschlich, et al., "Two-Dimensional Electrochromatography/Capillary Electrophoresis on a Microchip", Anal. Chem., vol. 73, pp. 2669-2674 (2001).
Harris, et al., "Shrinking the LC Landscape," Analytical Chemistry, pp. 65A-69A (Feb. 1, 2003).
He, et al., "Integrated Silica-Bead Separation Column for On-Chip LC-ESI", Solid-State Sensor, Actuator and Microsystems Workshop, Hilton Head Island, South Carolina, Jun. 6-10, 2004.
He, et al., "Ion Liquid Chromatography On-A-Chip with Beads-Packed Parylene Column", Proc. MEMS, pp. 212-215 (2004).
He, et al., "Microfabricated liquid chromatography columns based on collocated monolith support structures", J. Pharm. Biomed. Anal., vol. 17, pp. 925-932 (1998).
Herr, et al., "On-Chip Coupling of Isoelectric Focusing and Free Solution Electrophoresis for Multidimensional Separations", Anal. Chem., vol. 75, pp. 1180-1187 (2003).
Ho, et al., "Micro-Electro-Mechanical-Systems (MEMS) and Fluid Flows", Annu. Rev. Fluid Mech., vol. 30, pp. 579-612 (1998).
Hofmann, et al., "Adaptation of Capillary Isoelectric Focusing to Microchannels on a Glass Chip", Anal. Chem., vol. 71, pp. 678-686 (1999).
Jacobson, et al., "High-Speed Separations on a Microchip", Anal. Chem., vol. 66, pp. 1114-1118 (1994).
Kämper, et al., "A Self-Filling Low-Cost Membrane Micropump," International conference on Micro Electro Mechanical Systems, pp. 432-437 (Jan. 1998).
Kutter, et al., "Integrated Microchip Device with Electrokinetically Controlled Solvent Mixing for Isocratic and Gradient Elution in Micellar Electrokinetic Chromatography", Anal. Chem., vol. 69, pp. 5165-5171 (1997).
Lacher, et al., "Comparison of the performance characteristics of poly(dimethylsiloxane) and Pyrex microchip electrophoresis devices for peptide separations", J. Chromatogr. A, vol. 1004, pp. 225-235 (2003).
Laurell et al., "Miniaturization is mandatory unraveling the human proteome," Proteomics, vol. 2, pp. 345-351 (2002).
Lazar et al., "Multiple Open-Channel Electroosmotic Pumping System for Microfluidic Sample Handling," Analytical Chemistry, vol. 74, No. 24, pp. 6259-6268 (Dec. 15, 2002).
Lee et al., "Solvent Compatibility of Poly(Dimethylsiloxane)-Based Microfluidic Devices," Analytical Chemistry, vol. 75, No. 23, pp. 6544-6554 (Dec. 1, 2003).
Lee et al., "Fabrication and in vitro test of a microsyringe," Sensors and Actuators 83, pp. 17-23, (2000).
Li, et al., "Application of Microfluidic Devices to Proteomics Research", Mol. Cell Proteomics, vol. 1, pp. 157-168 (2002).
Li, et al., "Dynamic analyte introduction and focusing in plastic microfluidic devices for proteomic analysis", vol. 24, pp. 193-199 (2003).
Licklider, et al., "A Micromachined Chip-Based Electrospray Source for Mass Spectrometry", Anal. Chem., vol. 72, pp. 367-375 (2000).
Lion, et al., "Microfluidic systems in proteomics", Electrophoresis, vol. 24, pp. 3533-3562 (2003).
Liu, et al., "Electrophoretic Separation of Proteins on a Microchip with Noncovalent, Postcolumn Labeling", Anal. Chem., vol. 72, pp. 4608-4613 (2000).
Moore et al., "A Microscale Electrospray Interface Incorporating a Monolithic, Poly(styrene-divinylbenzene) Supporting for On-Line Liquid Chromatography/Tandem Mass Spectrometry Analysis of Peptides and Proteins," Analytical Chemistry, vol. 70, No. 23, pp. 4879-4884 (Dec. 1, 1998).
Munyan et al., "Electrically actuated, pressure-driven microfluidic pumps," Lap on a Chip, vol. 3, pp. 217-220 (2003).
Neagu et al., "An electrochemical active valve," Electrochimica Acta, vol. 42, No. 20-22, pp. 3367-3373 (1997).
Neagu et al., "An Electrochemical Microactuator: Principle and First Results," Journal of Microelectromechanical Systems, vol. 5, No. 1, pp. 2-9 (1996).
Nguyen et al., "MEMS—Micropumps: A Review," Transactions of the ASME, vol. 124, pp. 384-392 (Jun. 2002).
Park et al., "A Piezoelectric Micropump Using Resonance Drive with High Power Density," JSME International Journal, Series C, vol. 45, No. 2, pp. 502-509 (2002).
Paul et al., "Electrokinetic Generation of High Pressures Using Porous Microstructures," Micro Total Analysis Systems, pp. 49-52 (Oct. 1998).
Ramsey, et al., "High-Efficiency, Two-Dimensional Separations of Protein Digests on Microfluidic Devices," Anal. Chem., vol. 75, pp. 3758-3764 (2003).
Reichmuth et al., "Increasing the performance of high-pressure, high-efficiency electrokinetic micropumps using zwitterionic solute additives," Sensors and Actuators B 92, pp. 37-43 (2003).
Reyes et al., "Micro Total Analysis Systems. 1. Introduction, Theory, and Technology," Analytical Chemistry, vol. 74, No. 12, pp. 2623-2636 (Jun. 15, 2002).
Rocklin, et al., "A Microfabricated Fluidic Device for Performing Two-Dimensional Liquid-Phase Separations", Anal. Chem., vol. 72, pp. 5244-5249 (2000).
Schabmueller et al., "Self-aligning gas/liquid micropump," Journal of Micromechanics and Microengineering, vol. 12, pp. 420-424 (2002).
Selvaganapathy, et al., "Bubble-Free Electrokinetic Pumping," Journal of Microelectromechanical Systems, vol. 11, No. 5, pp. 448-453 (Oct. 2002).
Shih, et al., "Surface Micromachined and Integrated Capacitive Sensors for Microfluidic Applications", The 12th International Conf. on Solid-State Sensors, Actuators and Microsystems (Transducers 2003), Boston, USA, pp. 388-391 (Jun. 2003).

Slentz, et al., "Capillary electrochromatography of peptides on microfabricated poly(dimethylsiloxane) chips modified by cerium(IV)-catalyzed polymerization", J. Chromatogr. A, vol. 948, pp. 225-233 (2002).

Stanczyk et al., "A Microfabricated Electrochemical Actuator for Large Displacements," Journal of Microelectromechanical Systems, vol. 9, No. 3, pp. 314-320 (Sep. 2000).

Suzuki et al., "A reversible electrochemical nanosyringe pump and some consideration to realize low-power consumption," Sensors and Actuators B 86, pp. 242-250,(2002).

Svec, et al., "Design of the monolithic polymers used in capillary electrochromatography columns", J. Chromatogr. A, vol. 887, pp. 3-29 (2000).

Takamura et al., "Low-voltage electroosmosis pump for stand-alone microfluidics devices," Electrophoresis 2003, vol. 24, pp. 185-192 (2003).

Tan, et al. "Miniaturized capillary isoelectric focusing in plastic microfluidic devices", Electrophoresis, vol. 23, pp. 3638-3645 (2002).

Throckmorton, et al., "Electrochromatography in Microchips: Reversed-Phase Separation of Peptides and Amino Acids Using Photopatterned Rigid Polymer Monoliths", Anal. Chem., vol. 74, pp. 784-789 (2002).

Tsai, et al, "Application of plasma-polymerized films for isoelectric focusing of proteins in a capillary electrophoresis chip", Analyst, vol. 128, pp. 237-244 (2003).

Woias et al., "Micropumps—summarizing the first two decades," SPIE, vol. 4560, pp. 39-52 (2001).

Wu et al., "MEMS flow sensors for nano-fluidic applications," Sensors and Actuators A 89, pp. 152-158, (2001).

Xie et al., "An Electrochemical Pumping System for On-Chip Gradient Generation," Anal. Chem., vol. 76, pp. 3756-3763 (2004).

Xie et al., "An Integrated LC-ESI Chip with Electrochemical-Based-Gradient Generation," The 17th IEEE Intl. Conf. on MicroElectroMechanical Systems (MEMS 2004), Maastricht, the Netherlands, pp. 334-337 (Jan. 2004).

Xie et al., "Complete Gradient-LC-ESI System on a Chip for Protein Analysis", The 18th IEEE Intl. Conf. on MicroElectroMechanical Systems (MEMS 2005), Miami, Florida, USA, pp. 778-781 (Jan. 2005).

Xie et al., "Electrolysis-Based On-Chip Dispensing System for ESI-MS," Intl. Conf. on Micro Electro Mechanical Systems, pp. 443-446 (2003).

Xie et al., "Integrated Surface-Micromachined Mass Flow Controller", The 16th IEEE Intl. Conf. on MicroElectroMechanical Systems (MEMS 2003), Kyoto, Japan, pp. 20-23 (Jan. 2003).

Xie, et al., "Surace micromachined electrostatically actuated micro peristaltic pump", Lab Chip, vol. 4, pp. 495-501 (2004).

Zeng et al., "Fabrication and characterization of electroosmotic micropumps," Sensors and Actuators B 79, pp. 107-114 (2001).

* cited by examiner

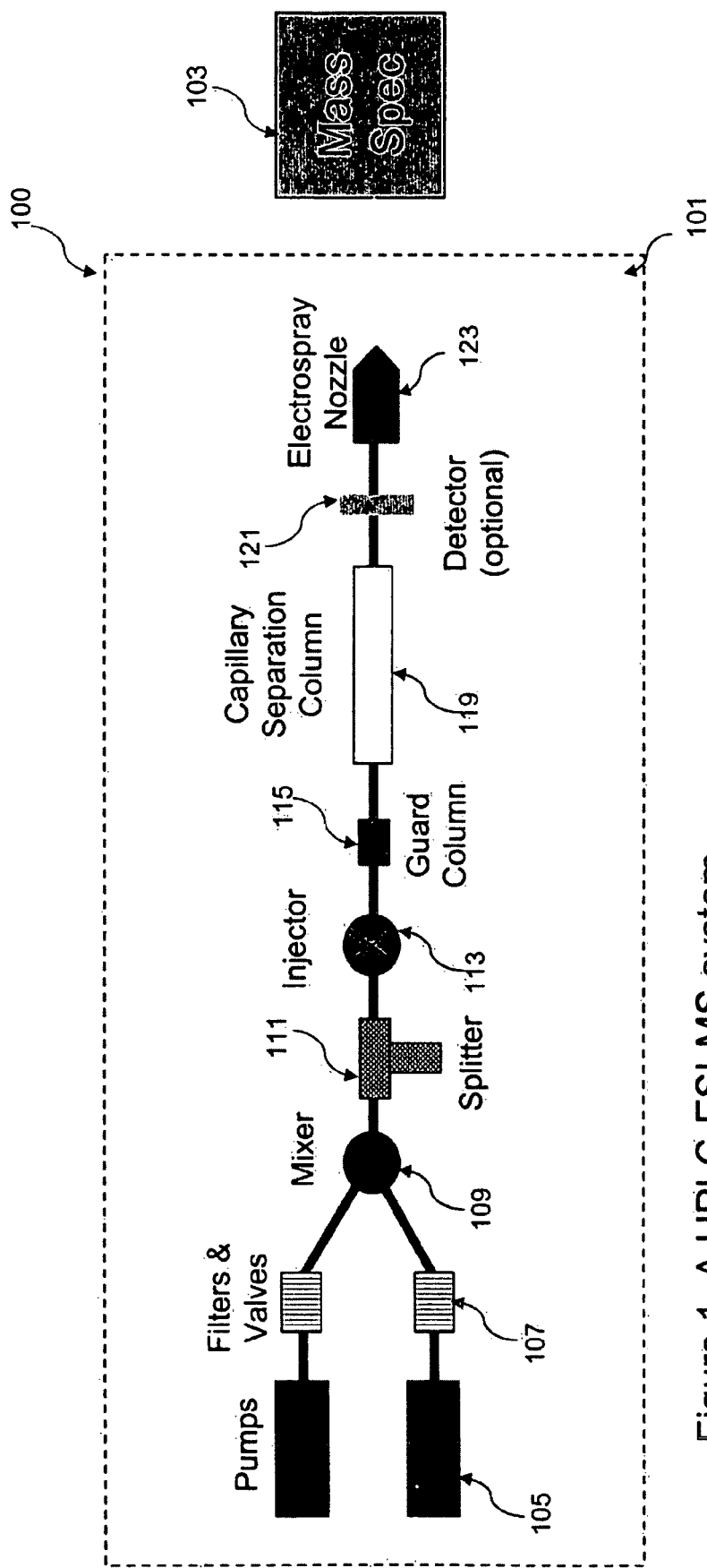
Figure 1. A HPLC-ESI-MS system

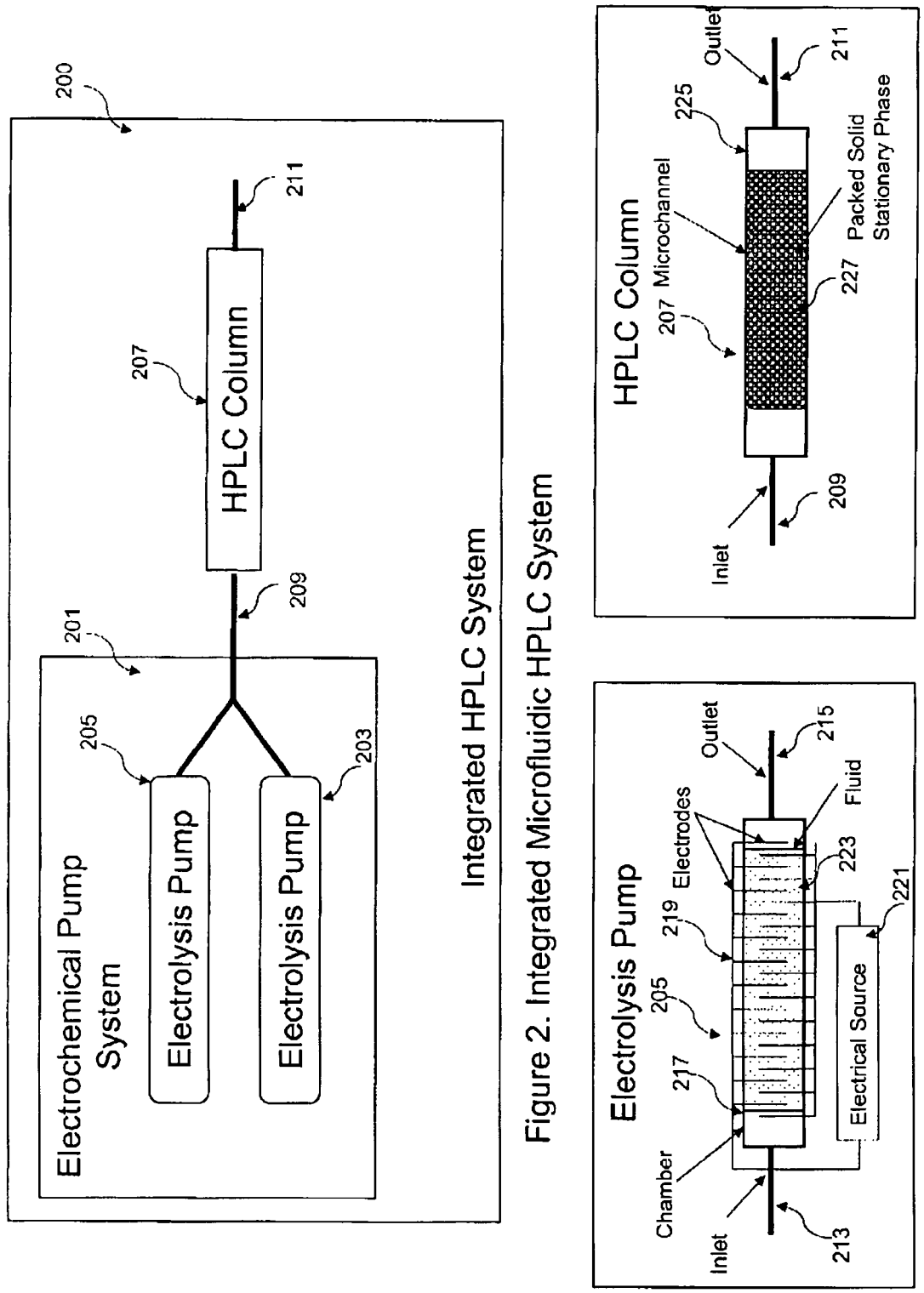
Figure 2. Integrated Microfluidic HPLC System

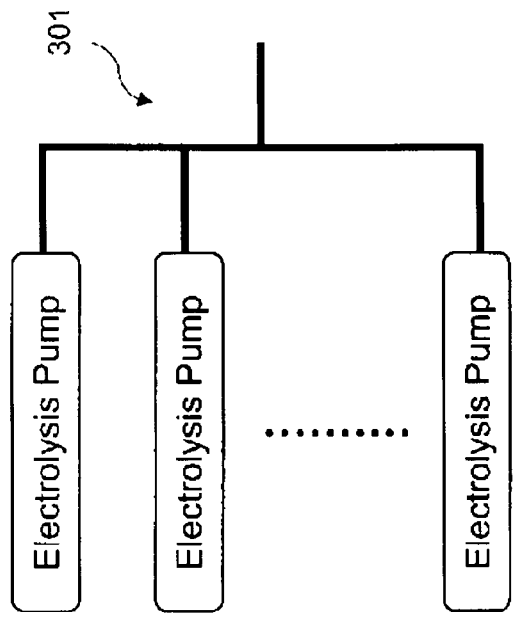
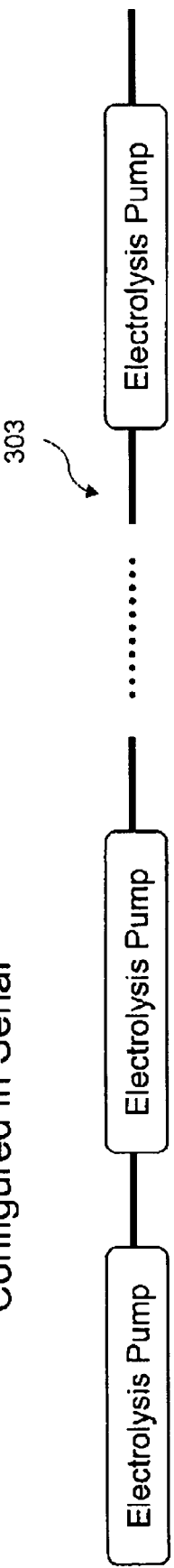
Figure 3a. Electrolysis Pumps Configured in Parallel
Figure 3b. Electrolysis Pumps Configured in Serial

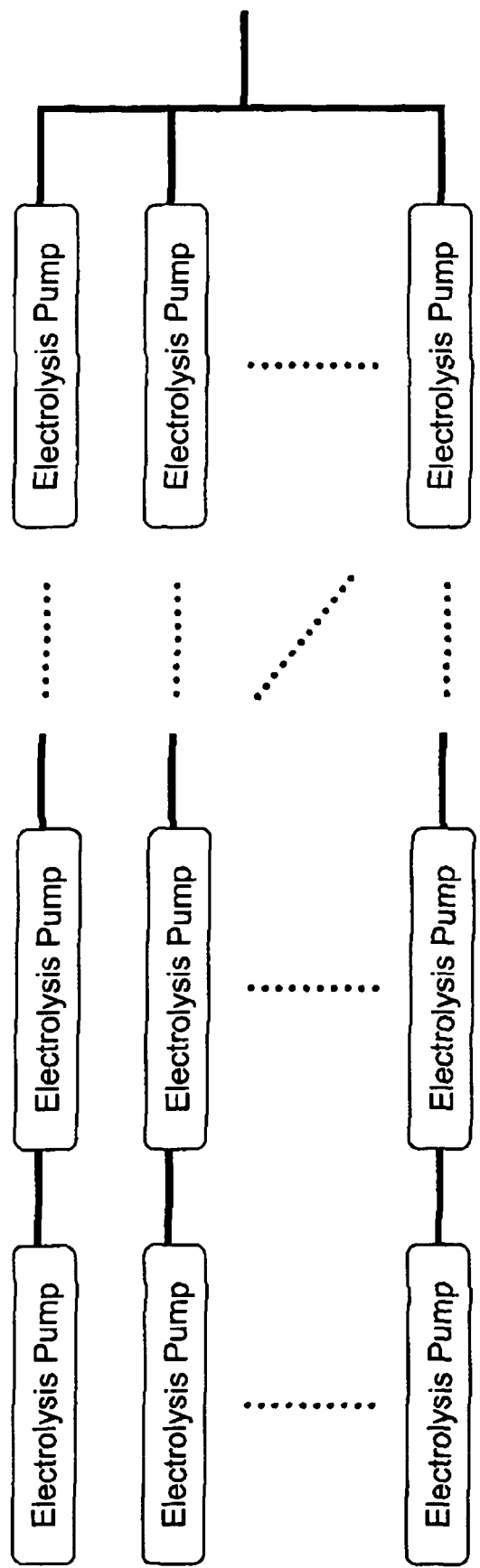
Figure 3c. Electrolysis Pumps Configured in Parallel and Serial

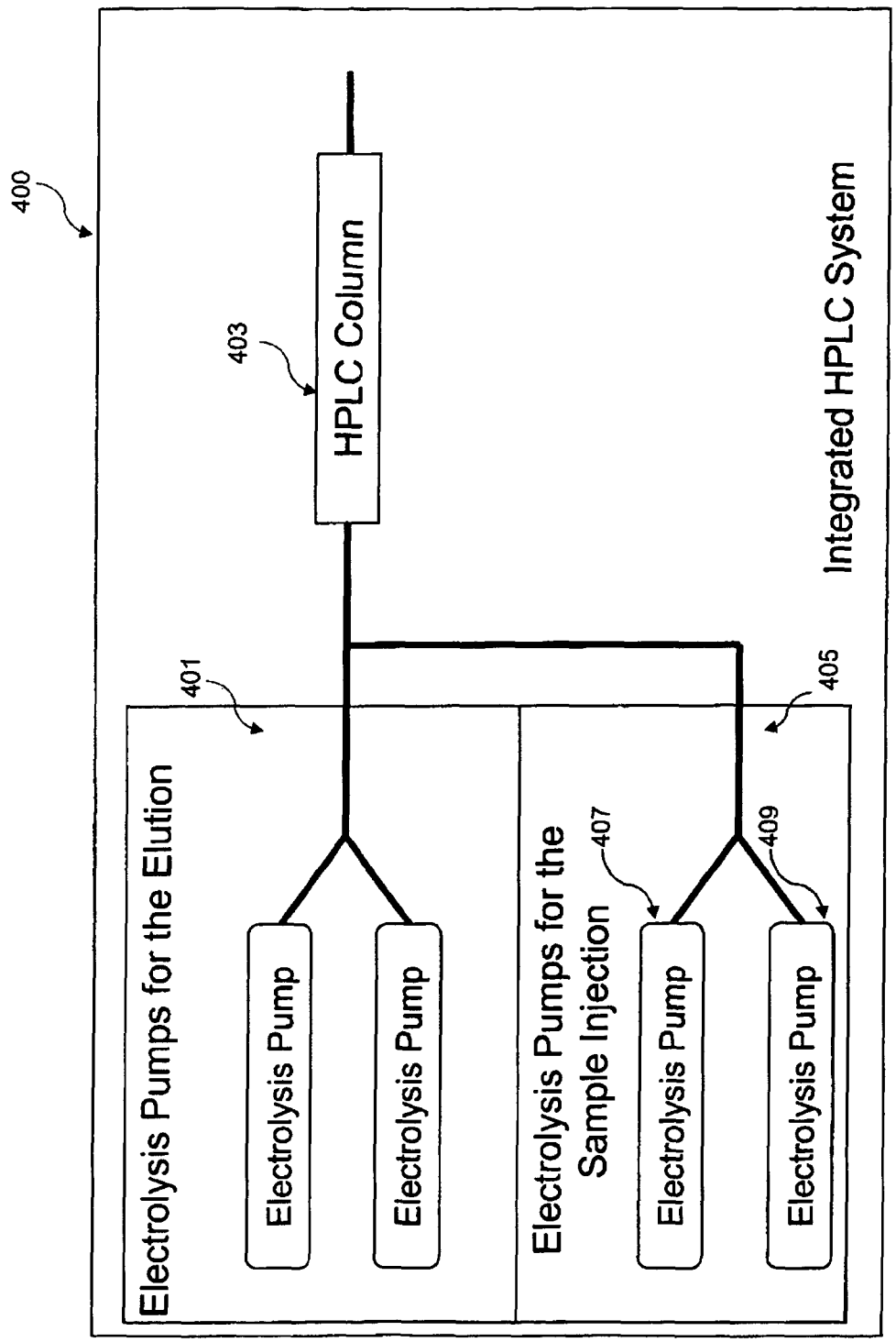
Figure 4. Integrated Microfluidic HPLC System With Sample Injection

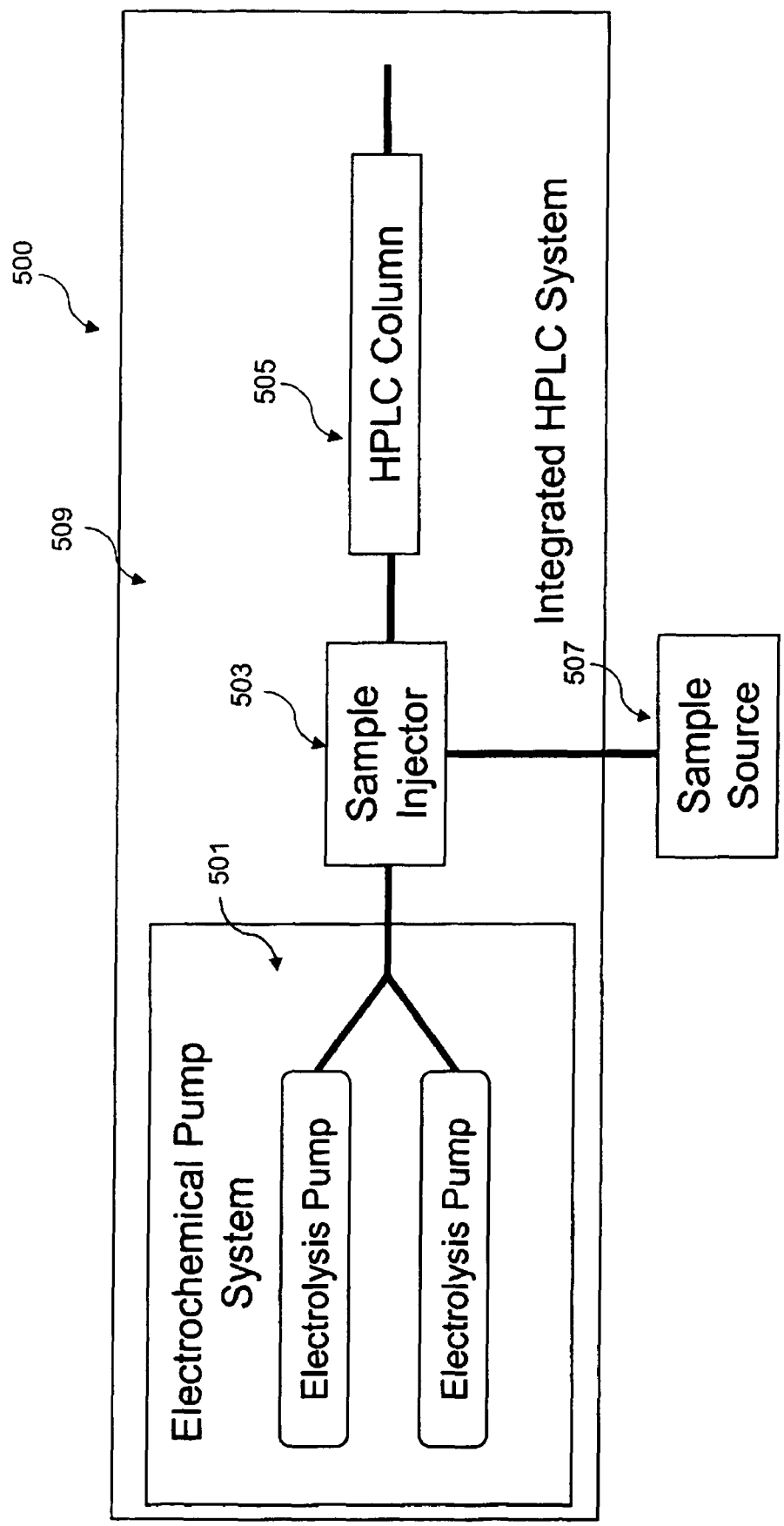
Figure 5. Integrated Microfluidic HPLC System With Sample Injection

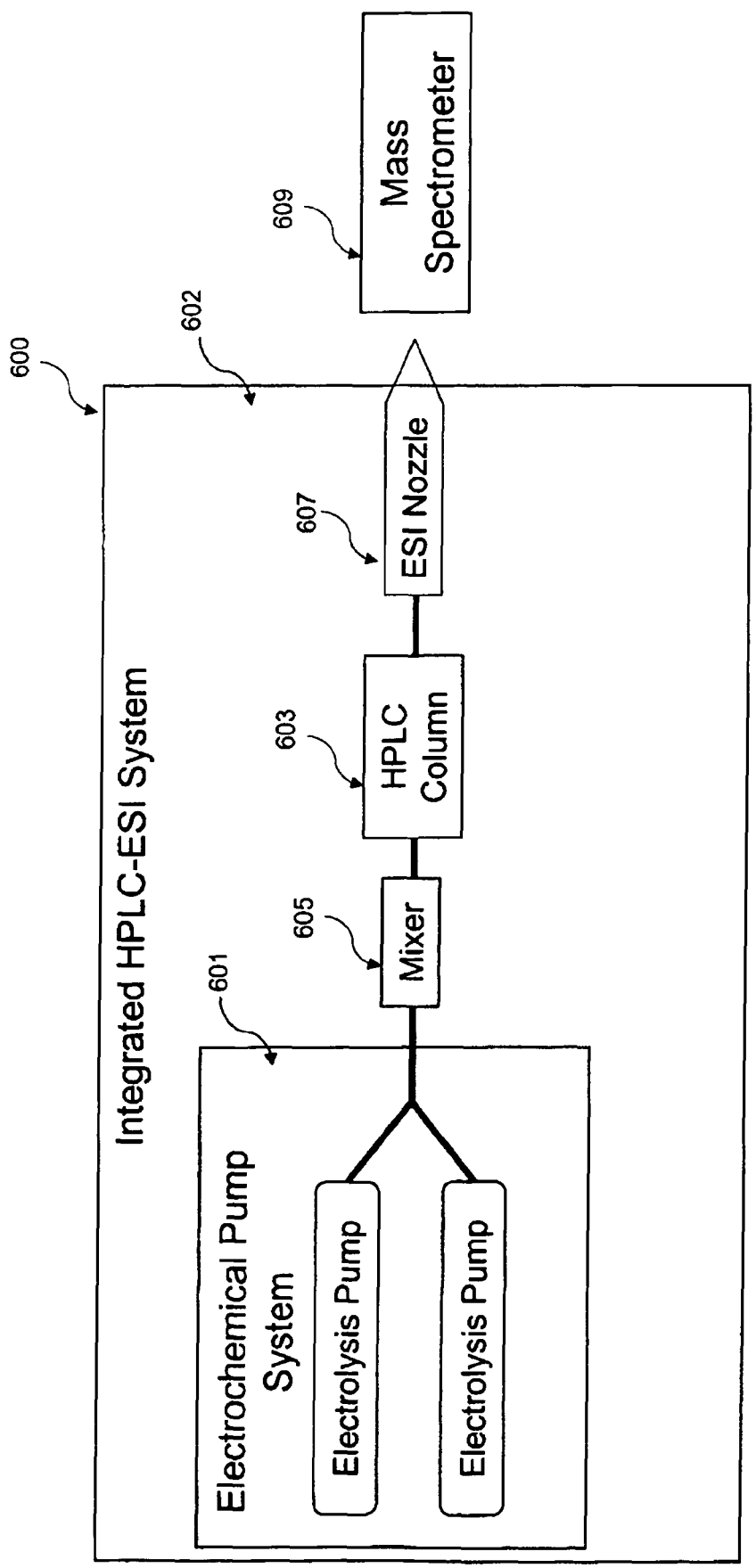
Figure 6. Integrated HPLC-ESI-MS System

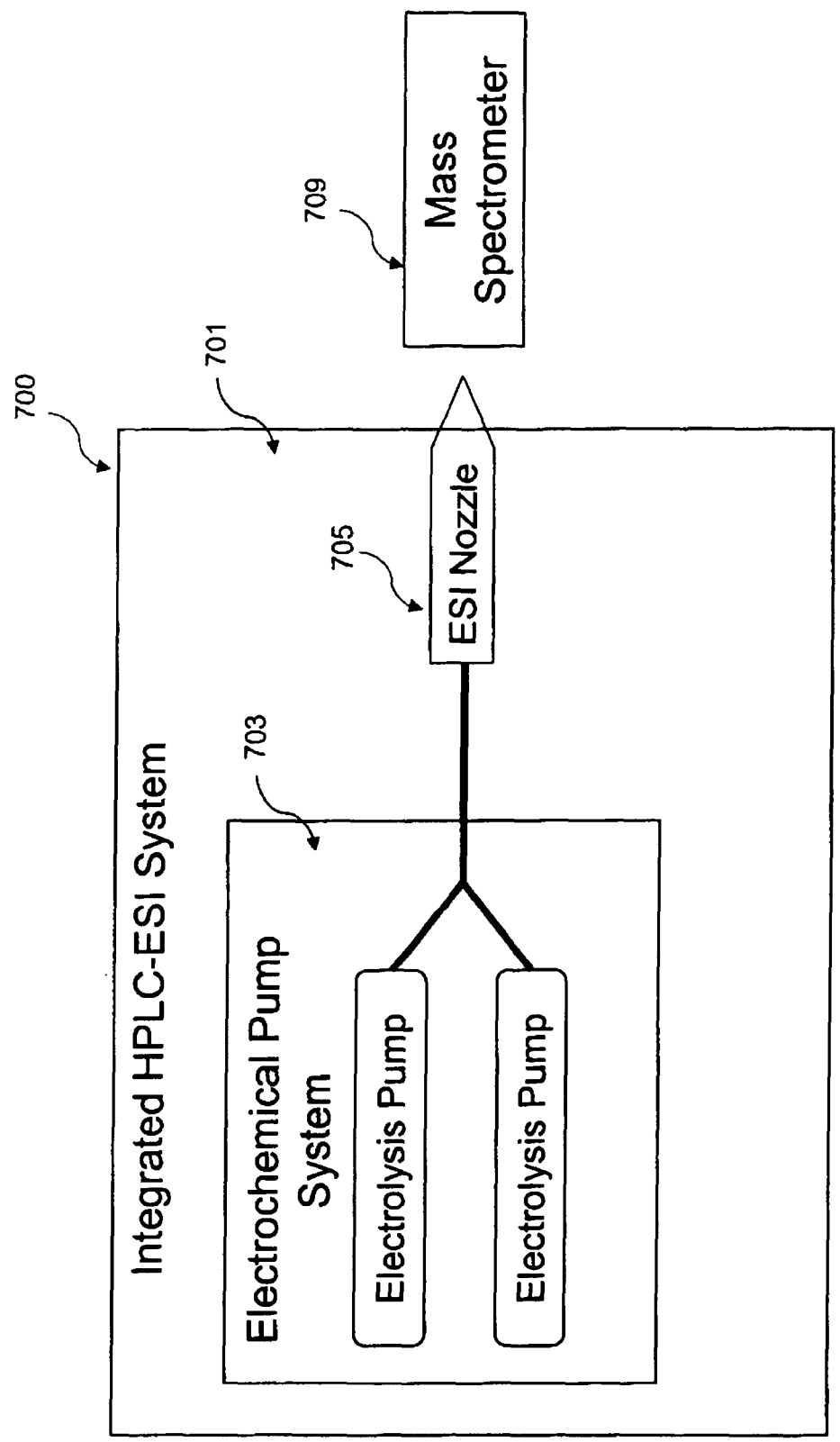
Figure 7. Integrated ESI-MS System

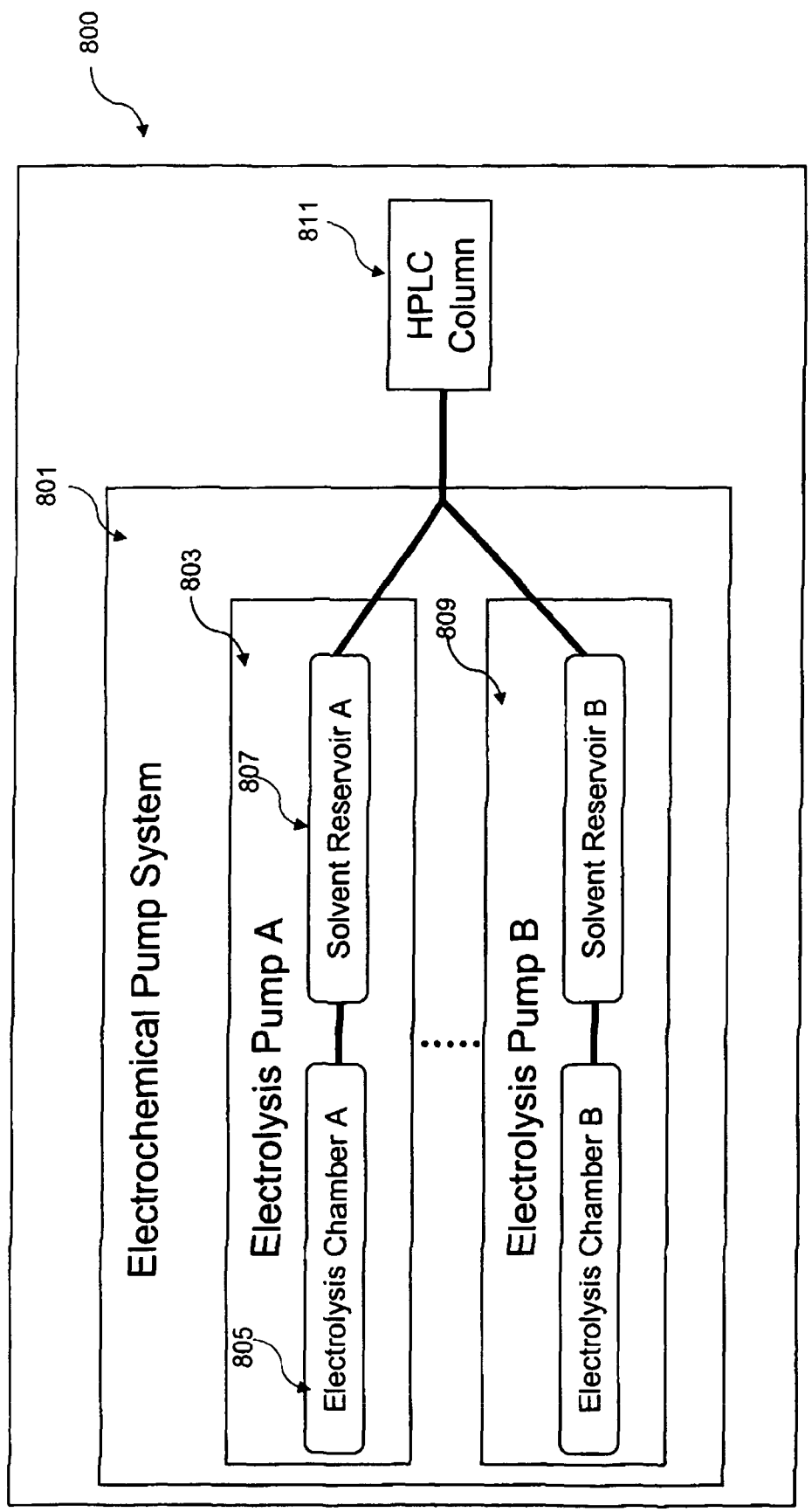
Figure 8. A HPLC system with a multi-chamber arrangement for electrolysis pump.

$H_2O\,(l) \Leftrightarrow H^+(aq) + OH^-(aq)$

Anode: $4OH^- \Leftrightarrow 2H_2O + O_2(g) + 4e^-$

Cathode: $2H^+(aq) + 2e^- \Leftrightarrow H_2(g)$

Figure 16
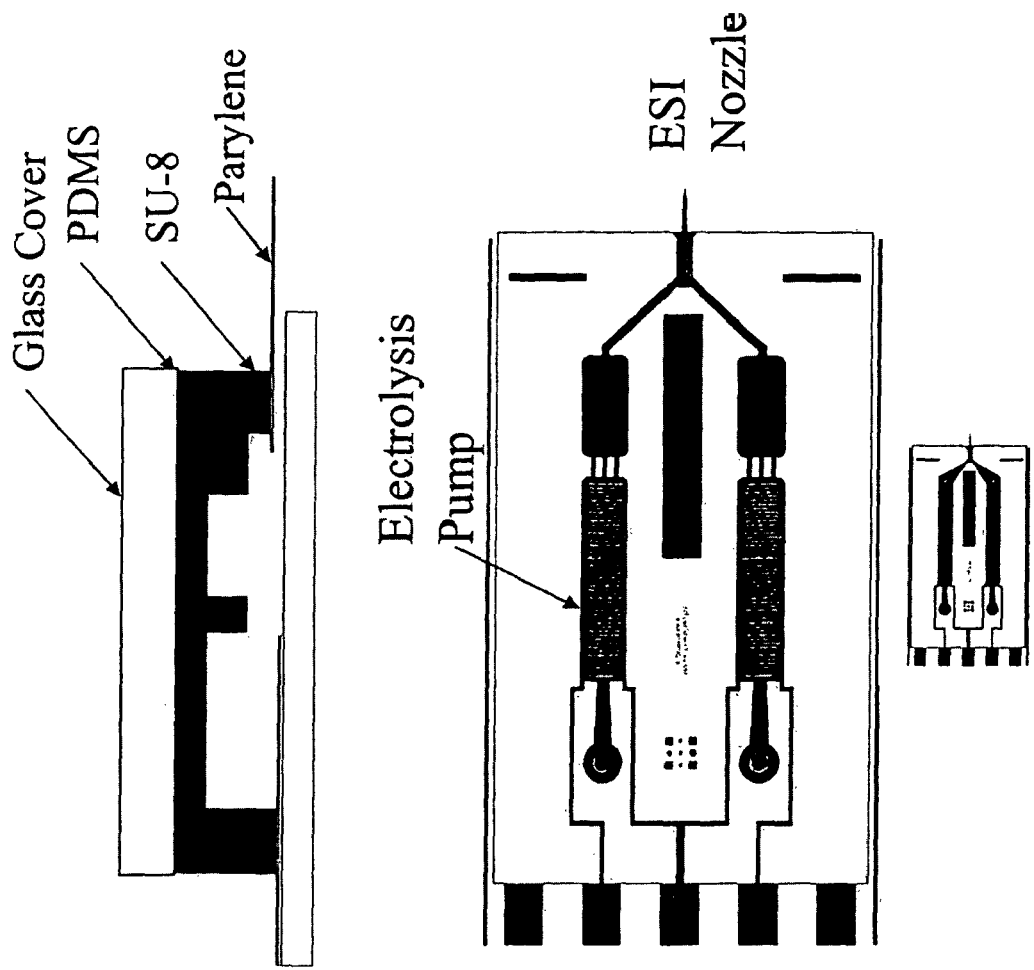
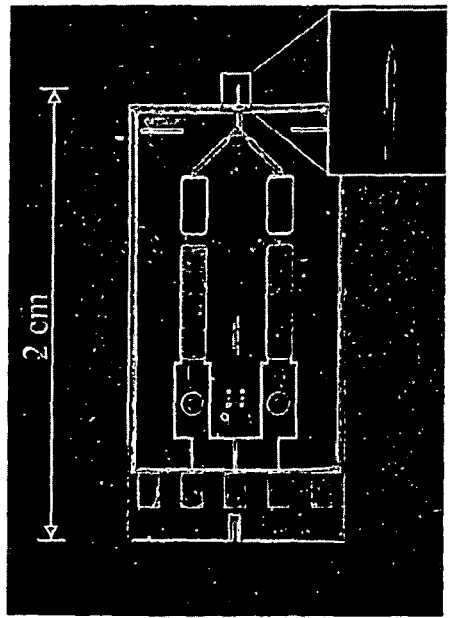
Fabricated Device Picture
Specifications:
Volume: 2+1=3 µL
Flow Rate: 100 nL/min
Pressure: 100 psi
Time: 20 min chip#4 Electrolysis chip test (chip#2 reused)
sample A: 10 pmol/µL TBAI in 90/10/0.1 water/acetonitrile/formic acid
sample B: 25 pmol/µL Angiotensin in 95/5/0.2 water/methanol/formic acid

INTEGRATED LC-ESI ON A CHIP

CROSS-REFERENCE TO RELATED PATENT APPLICATIONS

This application claims priority to U.S. Provisional Application No. 60/586,576 filed Jul. 9, 2004, "Integrated LC-ESI on a Chip", which is hereby incorporated by reference in its entirety. This application is also a continuation-in-part of U.S. patent application Ser. No. 10/603,573 filed Jun. 24, 2003, which claims priority to U.S. provisional application Ser. No. 60/391,822 filed Jun. 26, 2002, both applications of which are hereby incorporated by reference in their entirety.

FEDERALLY SPONSORED RESEARCH OR DEVELOPMENT

Work described herein has been supported, in part, by DARPA Grant No. N66001-00-C-8092NSF, Grant No. EEC-9402726, NIH Grant No. 5R01 RR06217-10 and CA33752. The United States Government may, therefore, have certain rights in the invention.

BACKGROUND

Over the years, chemical analysis techniques have progressed. In the early days, analysis procedures included liquid chromatography, which relates to a process for isolation had purification of compounds. In the early days, commercial liquid chromatographic methods were plagued with difficulties for a laboratory scientist. Later on, certain chemical separations used techniques such as open-column chromatography, paper chromatography, and thin-layer chromatography. Unfortunately, certain limitations existed with these techniques. For example, these chromatographic techniques were often inadequate for quantification of compounds and resolution between similar compounds. Accordingly, pressure liquid chromatography was developed. Such pressure chromatography improved flow through time, which often reduced purification times of certain compounds being isolated by the column approach. Unfortunately, flow rates were often inconsistent, See, Analytical Chem. Volume 62, Number 19, Oct. 1, 1990.

Accordingly, high pressure liquid chromatography ("HPLC") was developed to resolve some of these limitations of prior techniques. High pressure liquid chromatography improved development of column design and materials. Improvements to high pressure liquid chromatography improved separation between certain compounds, which were similar. More recently, computers and other automation have been added to HPLC for efficiency. Other techniques rely upon electro-osmotic forces for HPLC. An example of such HPLC has been described in U.S. Pat. No. 6,572,749, titled Electrokinetic High Pressure Hydraulic System (herein "the '749 patent"). The '749 patent generally claims an apparatus for fluid flow using electro-osmotic force applied to an electrolyte. The electro-osmotic force is used for an HPLC application. Unfortunately, numerous limitations exist with the electro-osmotic technique for HPLC. For example, electro-osmotic flow using electric fields to cause pressure for pumping and/or compressing liquids. In order to achieve a high pressure, a high voltage, such as 3000 volts, is usually needed. Additionally, the packing of porous materials inside the microchannel is also desired. Although HPLC has improved over the years, many limitations still exist.

From the above, it is desired to have an improved HPLC technique. A particularly important application is proteomics.

Proteomics, a study of protein structure and function, is a research focus for decades to come as it can allow one to elucidate the fundamentals of life and the molecular basis of health and disease. Analysis of complex protein mixtures usually involves two steps: separation and identification. A method of choice for protein identification is mass spectrometry carried out by electrospray ionization (ESI) or matrix-assisted laser desorption/ionization (MALDI). Two separation methods dominate proteomic landscape: 2D gel-electrophoresis (2D-GE) and multidimensional high-performance liquid chromatography (HPLC). An important advantage of HPLC compared to 2D-GE is a simple coupling to MS through ESI.

One of the demands of the fast growing proteomic research is a miniaturization of bioanalytical techniques, see e.g. T. Laurell and G. Marko-Varga, "Miniaturization is mandatory unraveling the human proteome", *Proteomics*, (2002), Vol. 2, pp. 345-351, incorporated hereby by reference in its entirety, Lion, N.; Rohner, T. C.; Dayon, L.; Arnaud, I. L.; Damoc, E.; Youhnovski, N.; Wu, Z. Y.; Roussel, C.; Josserand, J.; Jensen, H.; Rossier, J. S.; Przybylski, M.; Girault, H. H. *Electrophoresis* 2003, 24, 3533-3562, incorporated hereby by reference in its entirety. The miniaturization in liquid chromatography is evidenced by smaller beads, smaller diameter columns, and correspondingly smaller flow rates which have led to higher resolution, increased sensitivity, and faster separation.

An integration of LC-ESI on a single chip still has not been yet achieved. For example, a commercially available microfluidic chip by Agilent integrates a trapping column, separation column and electrospray source within a single structure, see e.g. Gottschlich, N.; Jacobson, S. C.; Culbertson, C. T.; Ramsey, J. M. *Anal Chem* 2001, 73, 2669-2674; Fortier, M. H.; Bonneil, E.; Goodley, P.; Thibault, P. *Anal Chem* 2005, 77, 1631-1640, both incorporated hereby by reference. However, the Agilent chip is still connected to a conventional LC system to deliver the gradient.

An integration of a complete LC-ESI system, including a pumping system, on a single chip is highly desirable for several reasons. First, an integration of a complete LC-ESI system on a single chip allows one to virtually eliminate a dead volume and, thus, improve an efficiency of LC analyses. Second, an integration of LC-ESI system on a single chip allows one to seamlessly integrate on-chip sensors which can improve the system's reliability and control. Third, miniaturization and integration of an entire LC-ESI system on a single chip can make the system portable. Fourth, miniaturization and integration of an entire LC-ESI system on a single chip can lead to a decrease in power consumption. Fifth, a full integration of a complete LC-ESI on a single chip can greatly reduce cost of the system. Additional advantages for integration are present.

SUMMARY

The present invention relates generally to microfluidic techniques. More particularly, the invention provides a method and system for performing a fluid transfer process using electrical energy through one of a plurality of microfluidic channels. Merely by way of example, the invention has been applied to a high pressure liquid chromatography process using an integrated microfluidic chip. But it would be recognized that the invention has a much broader range of applicability such as drug delivery, portable chemical analysis system, and the like.

More particularly, one embodiment provides a microfluidic system for liquid chromatography comprising: (A) a main chip comprising a front surface and a back surface, the main chip further comprising: a substrate having a front face and a back face; a chromatography column on the front face of said substrate, wherein said column has an inlet and an outlet; at least one pump system on the front face of said substrate comprising a pump chamber, at least one electrode, and an outlet microfluidically coupled to the inlet of said column; (B) a reservoir chip comprising a front surface and a back surface, wherein the reservoir chip has at least one cavity in the back surface which when disposed next to the front surface of the main chip extends the volume of the pump chamber. The microfluidic system can further comprise at least one electrospray ionization (ESI) nozzle on the front face of said substrate, wherein said nozzle has an inlet and an outlet, and wherein the inlet of the nozzle is microfluidically coupled to the outlet of the column. The microfluidic system also can further comprise a sealing element disposed between the back surface of the reservoir chip and the front surface of the main chip. The sealing element can be a gasket layer comprising a polymer material.

The microfluidic system can further comprise a cover disposed next to the front surface of the reservoir chip. A sealing element can be disposed between the front surface of the reservoir chip and the cover.

The microfluidic system can further comprise the combination: a first sealing element disposed between the back surface of the reservoir chip and the front surface of the main chip; a cover disposed next to the front surface of the reservoir chip; and a second sealing element disposed between the front surface of the reservoir chip and the cover.

The microfluidic system's reservoir chip can further comprise at least one inlet and at least one outlet which are in fluid communication with the cavity. In addition, the microfluidic system's main chip can further comprise a planarizing layer. The electrode can be part of a set of interdigitated electrodes. A spacing between the interdigitated electrodes can approximately equal a width of the interdigitated electrodes. The spacing between the interdigitated electrodes can be from about 5 microns to about 200 microns. The pump system can be fluidically coupled to the column through a fluidic network. The fluidic network can comprise at least one microfluidic channel. The microfluidic channel can have a cross-section smaller than $0.001$ $mm^2$. The microfluidic channel can be packed with microparticles, nanoparticles, or a combination thereof to increase flow resistance. The microparticles, nanoparticles, or combination thereof can be used as solid phase particles in a chromatography column. The microfluidic channel can comprise a restriction to increase flow resistance. The fluidic network further comprises a mixer for solvent mixing.

The microfluidic system can further comprise a flow sensor integrated with the mixer. The microfluidic system can further comprise at least one capacitive sensor integrated with the mixer, wherein said capacitive sensor measures a composition of a mobile phase. The microfluidic system also can further comprise a sensor integrated with the mixer, wherein said sensor comprises a plurality of interdigitated electrodes to measure a conductivity of the mobile phase. The microfluidic system's pump system can comprise a pump for sample injection. The chromatography column can be packed with microparticles, nanoparticles, or a combination thereof.

The chromatography column and the ESI nozzle can comprise a polymer material. The polymer material can be parylene. The ESI nozzle can comprise an electrode, and said electrode can be placed inside a channel defined between the inlet and the outlet of the ESI nozzle. The ESI nozzle can be engineered or adapted to have sufficient opening to allow sacrificial layer to escape during formation of the ESI nozzle and avoid plugging.

The electrode of the microfluidic system can comprise Ti, Au, Pt, Pd, Cr, Cu, Ag, carbon, graphite, pyrolyzed carbon, or a combination thereof. In addition, the microfluidic system can further comprise a jig to hold the assembled main chip and reservoir chip. The jig is adapted for use with a mass spectrometer.

Another embodiment provides a microfluidic system for liquid chromatography/electrospray ionization mass spectrometry comprising: (A) a main chip comprising a front surface and a back surface, the main chip further comprising: a substrate having a front face and a back face; at least one electrochemical pump system integrated on the front face of said substrate comprising a pump chamber, at least one electrode, and an outlet; a chromatography column integrated on the front face of said substrate, wherein said column has an inlet and an outlet, and the inlet of said column is microfluidically coupled to the pump outlet; a fluidic network integrated on the front face of the substrate to fluidically couple the pump and the column; at least one electrospray ionization (ESI) nozzle integrated on the front face of said substrate, wherein said nozzle has an inlet and an outlet, and wherein the inlet of the nozzle is microfluidically coupled to the outlet of the column; (B) a reservoir chip comprising a front surface and a back surface, wherein the reservoir chip has at least one cavity in the back surface which when disposed next to the front surface of the main chip extends the volume of the pump chamber, and wherein the reservoir chip further comprises at least one inlet and at least one outlet which are in fluid communication with the cavity; and further comprising: a first sealing element disposed between the back surface of the reservoir chip and the front surface of the main chip; a cover disposed next to the front surface of the reservoir chip; and a second sealing element disposed between the front surface of the reservoir chip and the cover.

Another embodiment is an integrated liquid chromatography-electrospray ionization chip comprising at least the following elements: solvent gradient pumps; a mixer; a sample injector; a column; and an electrospray ionization nozzle, wherein the elements are integrated onto a single chip. The chip can be further assembled with a separate reservoir chip which provides a total solvent volume of at least 10 microliters. The chip can be further assembled with a separate reservoir chip which provides at least two solvent reservoirs each having a solvent volume of at least 10 microliters. The chip can further provide a sample injector having a solvent volume of at least 3.5 microliters. The pumps can comprise interdigitated electrodes; the mixer can be a passive mixer, and the column can be a reverse-phase chromatography column.

The main chip can further comprise a planarization layer.

Another embodiment provides a microfluidic system comprising:

(A) a main chip comprising a front surface and a back surface, the main chip further comprising: a substrate having a front face and a back face; at least one pump system on the front face of said substrate comprising a pump chamber, at least one electrode, and an outlet; (B) a reservoir chip comprising a front surface and a back surface, wherein the reservoir chip has at least one cavity in the back surface which when disposed next to the front surface of the main chip extends the volume of the pump chamber.

Also provided is a method of making a microfluidic device with on-chip pumping, said method comprising: microfabricating a main chip, wherein said main chip has a front surface and a back surface, the main chip comprising at least one pump system on the front surface comprising a chamber providing a volume for storing a fluid; microfabricating a reservoir chip, wherein said reservoir chip has a front surface and a back surface and one or more cavities on the back surface; assembling the reservoir chip on the main chip so that the front surface of the main chip faces the back surface of the reservoir chip and so that at least one of the cavities of the reservoir chip extends the volume of the chamber.

Another embodiment provides a method of biomolecular separation comprising the step of chromatographically separating a mixture of biomolecules using a microfluidic system comprising: (A) a main chip comprising a front surface and a back surface, the main chip further comprising: a substrate having a front face and a back face; a chromatography column on the front face of said substrate, wherein said column has an inlet and an outlet; at least one pump system on the front face of said substrate comprising a pump chamber, at least one electrode, and an outlet microfluidically coupled to the inlet of said column; (B) a reservoir chip comprising a front surface and a back surface, wherein the reservoir chip has at least one cavity in the back surface which when disposed next to the front surface of the main chip extends the volume of the pump chamber. The biomolecules can comprise peptides or proteins. Alternatively, the biomolecules can comprise nucleic acid.

BRIEF DESCRIPTION OF THE DRAWINGS

FIG. 1 provides a simplified diagram of a microfluidic system integrating liquid chromatography and electrospray ionization FIG. 2 provides more detailed diagrams of an integrated HPLC system.

FIGS. 3a, 3b, and 3c provide simplified diagrams of various electrolysis pumps configurations according to embodiments of the present invention.

FIG. 4 provides a simplified diagram of an integrated HPLC system with a sample injection according to an embodiment of the present invention.

FIG. 5 provides a simplified diagram of an integrated HPLC system with a sample injection according to an alternative embodiment of the present invention.

FIG. 6 provides an integrated HPLC-ESI-MS system according to an embodiment of the present invention.

FIG. 7 provides an integrated ESI-MS system according to an alternative embodiment of the present invention.

FIG. 8 provides an HPLC system with a multi-chamber arrangement for electrolysis pump according to an embodiment of the present invention.

FIG. 16 shows a chip with two electrolysis chambers (as pumps) coupled to an ESI nozzle.

DETAILED DESCRIPTION

Figure 9:
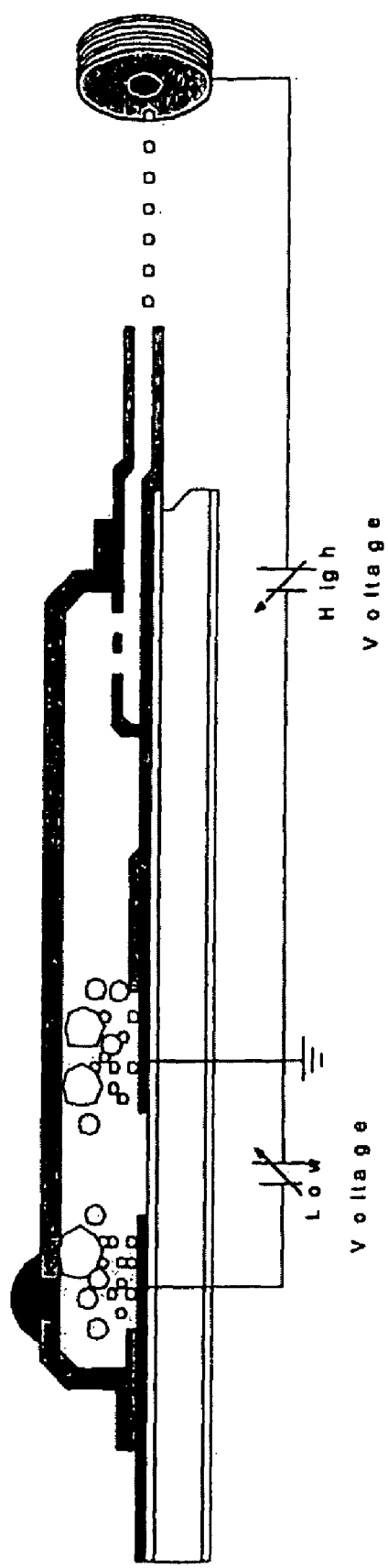
FIG. 9 illustrates a principle of operation of electrolysis pump.

The following patent documents, which generally relate to microfluidics and elements on a chip, can be useful for understanding and practicing the various embodiments of this invention, and are incorporated by reference in their entirety:

(i) US patent application publication No. 2005-0051489 to Tai et. al. published Mar. 10, 2005, incorporated hereby by reference in its entirety;

(ii) US patent application publication No. 2003-0228411 to Tai et. al. published Dec. 11, 2003, incorporated hereby by reference in its entirety;

(iii) U.S. patent application Ser. No. 09/442,843 to Tai et. al. filed Nov. 18, 1999, incorporated hereby by reference in its entirety;

(iv) US patent application publication No. 2004-0124085 to Tai et. al. published Jul. 1, 2004, incorporated hereby by reference in its entirety;
(v) US patent application publication No. 2004-0237657 "Integrated Capacitive Microfluidic Sensors Method and Apparatus" by Tai et. al. published Dec. 2, 2004, incorporated hereby by reference in their entirety;
(vi) US patent application publication No. 2004-0188648 "INTEGRATED SURFACE-MACHINED MICRO FLOW CONTROLLER METHOD AND APPARATUS" to Xie et. al. published Sep. 30, 2004, which is a publication of U.S. patent application Ser. No. 10/757,030 filed Jan. 13, 2004, and claiming priority to U.S. provisional patent application No. 60/440,107 filed Jan. 15, 2003, which are all incorporated hereby by reference in their entirety;
(vii) U.S. patent application Ser. No. 11/059,625 "On-Chip Temperature Controlled Liquid Chromatography Methods and Devices" by Tai et. al. filed Feb. 17, 2005, and claiming priority to U.S. provisional application No. 60/545,727 filed Feb. 17, 2004, which are both incorporated hereby by reference in their entirety;
(viii) U.S. Pat. No. 5,994,696 "MEMS electrospray nozzle for mass spectroscopy" to Tai et. al. issued Nov. 30, 1999, and incorporated hereby by reference in its entirety;
(ix) U.S. Pat. No. 6,436,229 "Gas phase silicon etching with bromine trifluoride" to Tai et. al. issued Aug. 20, 2002, and incorporated hereby by reference in its entirety;
(x) U.S. Pat. No. 6,162,367 "Gas phase silicon etching with bromine trifluoride" to Tai et. al. issued Dec. 19, 2002, and incorporated hereby by reference in its entirety;
(xi) U.S. provisional patent application No. 60/663,181, "Wafer Scale Solid Phase Packing" filed Mar. 18, 2005 to Xie, Young, and Tai, incorporated hereby by reference in its entirety;
(xii) U.S. provisional application No. 60/671,309, "Integrated Chromatography Devices and Systems for Monitoring Analytes in Real Time," filed Apr. 14, 2005, to Xie, Young, and Tai, incorporated hereby by reference in its entirety;
(xiii) U.S. provisional patent application No. 60/592,588 "Modular Microfluidic Packaging System" by Tai et. al. filed Jul. 28, 2004, incorporated hereby by reference in its entirety.

Also, the following technical literature can be useful for understanding and practicing the various embodiments of this invention:
(1) Xie, J.; Miao, Y.; Shih, J.; He, Q.; Liu, J.; Tai, Y. C.; Lee, T. D. *Anal. Chem.* 2004, 76, 3756-3763, incorporated hereby by reference in its entirety;
(2) Licklider, L.; Wang, X.-Q.; Desai, A.; Tai, Y.-C.; Lee, T. D. *Anal. Chem.* 2000, 72, 367-375, incorporated hereby by reference in its entirety;
(3) Jun Xie, Jason Shih, Qing He, Changlin Pang, Yu-Chong Tai, Yunan Miao, and Terry D. Lee, "*An Integrated LC-ESI Chip With Electrochemical-Based Gradient Generation*", The 17$^{th}$ IEEE International Conference on MicroElectro-Mechanical Systems (MEMS 2004), Maastricht, The Netherlands, January, 2004, pp. 334-337, incorporated hereby by reference in its entirety;
(4) Qing He, Jun Xie, Yu-Chong Tai, Yunan Miao, and Terry D. Lee, "*Integrated Silica-Bead Separation Column for On-Chip LC-ESI*", Solid-State Sensor, Actuator, and Microsystems Workshop (Hilton Head 2004), Hilton Head Island, S.C., USA, June, 2004, pp. 298-301, incorporated hereby by reference in its entirety.

U.S. Pat. Nos. 4,402,817 and 4,687,423 to Maget describe electrolysis pumping which can be used in practice of the various embodiments, and these patents are incorporated by reference in their entirety.

Priority U.S. patent application Ser. No. 10/603,573 filed Jun. 24, 2003 is hereby incorporated by reference in it entirety. This application in turn claims priority to U.S. provisional application Ser. No. 60/391,822 filed Jun. 26, 2002, which also is hereby incorporated by reference in its entirety. This incorporation includes the background, the brief summary of the invention, the brief description of the drawings, the 18 drawings, the detailed description of the invention, the experiments, and the claims.

According to the present invention, techniques for microfluidic applications are provided. More particularly, the invention provides a method and system for performing a fluid transfer process using electrical energy through one of a plurality of microfluidic channels. Merely be way of example, the invention has been applied to a high pressure liquid chromatography process using an integrated microfluidic chip. But it would be recognized that the invention has a much broader range of applicability such as drug delivery, portable chemical analysis system, and the like.

In a specific embodiment, the invention provides a microfluidic system for liquid chromatography. The system includes a substrate, which has various elements. An electrochemical pump system is disposed on the substrate, the pump system having a plurality of electrolysis pumps and at least one outlet. Each of the pumps has at least one outlet. Each electrolysis pump has a chamber and a plurality of electrodes, which are coupled to an electrical source. A fluid is inside the chamber and is contacted with the electrodes. The pump also has an inlet and an outlet. A separation column is disposed on the substrate. The column has an inlet and an outlet. An micro channel is defined between the inlet and outlet. A solid stationary phase material (e.g., silica and alumina) is packed inside the micro channel. Preferably, the inlet of the separation column is coupled to the at least one outlet of the electrochemical pump system. The electrochemical pump system and the separation column are configured such that the electrochemical pump system provides an elution for a separation process within the separation column.

In an alternative specific embodiment, the invention provides a microfluidic system for electrospray ionization (ESI) and mass spectrometry (MS). The system has a substrate and an electrochemical pump system is disposed on the substrate. The electrochemical pump system has a plurality of electrolysis pumps and at least one outlet. Each pump includes a chamber and a plurality of electrodes, which are coupled to an electrical source. A fluid is inside the chamber and is preferably contacted with the electrodes. The pump also has an inlet and an outlet.

Preferably, an electrospray ionization (ESI) nozzle is also disposed on the substrate. The ESI nozzle has an inlet, an outlet, a micro channel coupled between the inlet and the outlet, and an ESI electrode within the micro channel. The inlet of the ESI nozzle can be coupled to the outlet of the electrochemical pump system. The system also has a mass spectrometer including an inlet, which is coupled to the outlet of the ESI nozzle. The electrochemical pump system and the ESI nozzle are configured such that the electrochemical pump system provides a driving force to cause the fluid to flow through the micro channel of the ESI nozzle and flow out through the outlet of the ESI nozzle, and the fluid emitted from the outlet of the ESI nozzle is transferred to the mass spectrometer as a voltage source is applied between the ESI electrode and the mass spectrometer.

In yet an alternative embodiment, the invention provides a method for transferring fluid on a microfluidic chip based on an electrochemical actuation. The method includes transferring a fluid into a chamber through an inlet within the substrate and providing an electrical connection using a plurality of electrodes coupled to the chamber. The method includes transferring a portion of the fluid from the chamber through an outlet while applying an electrical energy to the plurality of electrodes using the electrical connection, whereupon the portion of the fluid is transferred free from any coupling to an external fluidic source. The transferring a portion of the fluid is performed in response to the electrical energy applied to the plurality of electrodes.

Still further, the invention provides a method for controlling fluid through a microfluidic system in a liquid chromatography application. The method applies an electrical source between the plurality of electrodes to cause an electrochemical reaction within a first fluid in a chamber coupled to the plurality of electrodes. The method generates a gaseous species from the electrochemical reaction in the first fluid to increase a pressure within the chamber. Preferably, the method transfers a second fluid through a separation column to separate one or more components in the second fluid using the pressure associated with the chamber for liquid chromatography.

Still further in yet an alternative embodiment, the invention provides a method for performing liquid chromatography using a multi-chamber arrangement. The method includes applying an electrical source between a plurality of electrodes to cause an electrochemical reaction within a first fluid in a first chamber. Preferably, the first chamber is among a plurality of chambers. Each of the chambers is numbered from 1 through N, where N is an integer greater than 1. The first fluid is among a plurality of fluids numbered from 1 through N, where each of the fluids is respectively associated with at least one of the chambers. The method includes generating a gaseous species from the electrochemical reaction in the first fluid to increase a first pressure within the first chamber, and transferring a first liquid chromatography fluid from a first reservoir to a separation column using the first pressure associated with the first chamber. The first liquid chromatography fluid is from a plurality of liquid chromatography fluids numbered from 1 through N. Each of the liquid chromatography fluids is associated with a respective reservoir chamber also numbered from 1 through N. Depending upon the embodiment, the method further includes applying, generating, and transferring for any of the other chambers including any of the other respective fluids and reservoirs.

In an alternative specific embodiment, the invention provides a method for controlling fluid through a microfluidic system for ESI-MS. The method includes transferring a first fluid from an inlet into a chamber, which is formed on a first portion of a substrate. The chamber has a plurality of electrodes, which are configured to apply electrical forces to the first fluid. The method includes applying an electrical source between the plurality of electrodes and causing an electrochemical reaction within the chamber based upon the application of the electrical source onto the electrodes, the electrodes being coupled to the first fluid. The method also includes generating a gaseous species from the electrochemical reaction to increase a pressure within the chamber. The pressure in the chamber is used to provide a driving force for injection of a second fluid for ESI-MS. Preferably, the injection is controlled by adjusting an electrical source coupled to the plurality of electrodes.

Numerous benefits are achieved using the present invention over conventional techniques. For example, the invention can be applied for Mass Spectrometry (MS) and other applications. Preferably, the invention provides a system that is integrated with various microfluidic components, such as electrolysis-based micro pump, micro mixer, and electro spray ionization (ESI) nozzle, among other elements. Depending upon the embodiment, multi-layered Parylene surface micromachining have been used, although other fabrication techniques can also be used. Additionally, application of the present system includes multisource precise dispensing for MS and gradient elution for HPLC. By using the present method, complex fluidic handling can be done on a single chip and the use of only electrical control also simplifies automation in certain embodiments. The system can also be mass produced at lower costs for commercialization. Depending upon the embodiment, one or more of these benefits may exist. These and other benefits have been described throughout the present specification and more particularly below.

FIG. 1 is a simplified diagram of an integrated system 100 according to an embodiment of the present invention. This diagram is merely an example, which should not unduly limit the scope of the claims herein. One of ordinary skill in the art would recognize many variations, alternatives, and modifications. As shown, the integrated microfluidic system 100 is for liquid chromatography and preferably for mass spectroscopy. The system includes a substrate 101. The substrate can be made of a variety of materials. Such materials include single materials, alloys, and multilayered structures, or any combination of these. The substrate can be made of silicon, glass, plastic, and various polymer materials. Of course, the substrate used will depend upon the application.

As shown, the system includes an electrochemical pump system 105 (e.g., plurality or single) on the substrate. Each of the pumps has at least one outlet. Each of the pumps includes elements such as a chamber, a plurality of electrodes, which are coupled to an electrical source, a fluid inside the chamber, and an inlet and an outlet. Fluid enters the inlet and exits the outlet. The system also includes a separation column 119 on the substrate having an inlet and an outlet. The separation column also has a micro-channel, a solid stationary phase material packed inside the micro-channel. The inlet of the separation column is coupled to the outlet of the electrochemical pump. The electrochemical pump system and the separation column are configured such that the electrochemical pump system provides the elution for the separation process inside the separation column.

Depending upon the embodiment, other elements can also be integrated onto the substrate. These elements include filters and valves 107, a mixer 109, a splitter 111, an injector 113, a guard column 115, a detector 121, and an electro-stray tip or nozzle 123. Each of these elements are fabricated on the substrate using the techniques described herein, but can also be other techniques. The mass spectrometer 103 is coupled to the nozzle but is often outside of the integrated elements on the substrate. Other systems can also be coupled to the separation column. These systems include, among others, a UV analyzer, a conductivity analyzer, a refractive index analyzer, a fluorescence analyzer, an electrochemical analyzer, a light scattering analyzer. These and other features of the system are described in more detail throughout the present specification and more particularly below.

FIG. 2 is a more detailed diagram of an integrated HPLC system 200 according to an embodiment of the present invention. This diagram is merely an example, which should not unduly limit the scope of the claims herein. One of ordinary skill in the art would recognize many variations, alternatives, and modifications. As shown, the system includes an electrochemical pump system 201 (e.g., plurality or single), which includes a plurality of electrolysis pumps 203, 205 on the substrate. Each of the electrolysis pumps has at least one outlet 215. Each of the electrolysis pumps include elements such as a chamber 217, a plurality of electrodes 219, which are coupled to an electrical source 221, a fluid 223 (e.g., an electrolyte that is selected from organic liquid, inorganic liquid, or the combination of inorganic or organic liquid (e.g., acetonitrile, methanol, ethanol)) inside the chamber, and an inlet 213 and the outlet 215. The chamber can be made of suitable materials, e.g., Parylene, SU-8, silicone, silicon, silicon oxide, glass, Teflon, PEEK, other polymer materials or any combination of these materials. The electrodes are made of a suitable material that is conductive. Such electrode material may include, among others, carbon, platinum, gold, aluminum, titanium, chromium, and other noble metals. Fluid enters the inlet and exits the outlet.

The system also includes an separation column 207 on the substrate having an inlet 209 and an outlet 211. The column also has a micro-channel 225, a solid stationary phase material 227 packed inside the micro-channel. The inlet of the separation column is coupled to the outlet of the electrochemical pump, as shown. Depending upon the embodiment, other elements may be disposed between the pump and separation column. The electrochemical pump system and the separation column are configured such that the electrochemical pump system provides the elution for the separation process inside the separation column. Further details of a method according to the present invention are provided in more detail below.

According to a specific embodiment, the system can perform a variety of methods. An example of such a method is for controlling fluid through the present microfluidic system in a liquid chromatography application. The method includes transferring fluid from the inlet into the chamber. An electrical source is applied between the plurality of electrodes. The electrical source can be a voltage source or a current source or a voltage/current source. Here, the electrolysis pump is adapted to maintain a pressure on the fluid in the chamber while the electrodes are biased using the electrical source. Electrical energy from the source causes an electrochemical reaction within the chamber based upon the application of the electrical source onto the electrodes. Preferably, the electrodes are directly coupled to the fluid. To cause a pumping action, a gaseous species is generated from the electrochemical reaction to increase a pressure within the chamber. The pressure is used to provide driving force for an elution in the separation column for liquid chromatography. In a specific embodiment, the pressure can be higher than 1000 psia or less than 1000 psia or less than 100 psia. Depending upon the embodiment, the method can also control the liquid chromatography process. Here, control can be achieved by adjusting the electrical source that applies the plurality of electrodes.

In a specific embodiment, the system and method provides for selected fluid flow. Here, fluid output from the chamber can be about 1 micro liter of fluid. Alternatively, the fluid output from the chamber can be greater than about 1 micrometer of fluid. Alternatively, the fluid output from the chamber can be less than about 1 micrometer of fluid. Alternatively, the electrochemical pump system is characterized to provide a flow rate of about 1 nanoliter per minute to about 1 micro liter per minute through the separation column. Alternatively, the electrochemical pump system is characterized to provide a flow rate of less than about 1 nanoliter per minute through the separation column or is characterized to provide a flow rate of greater than about 1 micro liter per minute through the separation column. Of course, the particular flow rate will depend upon the application. Depending upon the embodiment, each of the electrolysis pumps can be configured with respect to each other in alternative arrangements, including parallel, serial, and any combination of these.

FIGS. 3A, 3B, and 3C are simplified diagrams of electrolysis pumps according to embodiments of the present invention. These diagrams are merely an example, which should not unduly limit the scope of the claims herein. One of ordinary skill in the art would recognize many variations, alternatives, and modifications. As shown, the pumps can be configured in parallel 301, or serial 303, or parallel and serial 306. The pumps in parallel each include an outlet that connects to a common port, which interfaces to another element. Each of the pumps can apply fluid together or any one of the pumps can apply fluid independent of the other or any sequential order. The pumps in serial configuration can also be applied together or sequentially or any one of the pumps can be applied independently of the others. Alternatively, the pumps in serial and parallel configuration could be applied in a number of different processes, which would be appreciated by one of ordinary skill in the art. The pumps in serial and parallel form an array of pumps, including N pumps in serial and M pumps in parallel, where N and M are greater than 1, in a specific embodiment.

FIG. 4 is a simplified diagram of an integrated HPLC system 400 with a sample injection according to an embodiment of the present invention. This diagram is merely an example, which should not unduly limit the scope of the claims herein. One of ordinary skill in the art would recognize many variations, alternatives, and modifications. As shown, the system 400 includes a plurality of electrolysis pumps 401, which are configured in parallel. Each of these pumps is coupled to an inlet of an HPLC column 403. The HPLC column includes an outlet. Between the electrolysis pumps and column, sample injection source 405 is provided. The sample injection source includes a plurality of electrolysis pumps 407, which are configured in parallel, but may also be in serial, depending upon the embodiment. Each of the electrolysis pumps includes an outlet that is coupled to the inlet of the HPLC column. Depending upon the embodiment, various fluids can be provided within each of the electrolysis pumps in the sample injection source. Alternative embodiments of the sample injection source are provided throughout the present specification and more particularly below.

FIG. 5 is a simplified diagram of an integrated HPLC system 500 with a sample injection according to an alternative embodiment of the present invention. This diagram is merely an example, which should not unduly limit the scope of the claims herein. One of ordinary skill in the art would recognize many variations, alternatives, and modifications. As shown, the system 500 includes a plurality of electrolysis pumps 501, which are configured in parallel, on a substrate. Each of these electrolysis pumps is coupled to an inlet of an HPLC column 505. The HPLC column includes an outlet. Between the electrolysis pumps and column, sample injector 503 is provided. The sample injector is coupled to sample source 507, which may be outside of the substrate. Depending upon the embodiment, various fluids can be provided by the sample injector. Alternative embodiments of the system are provided throughout the present specification and more particularly below.

FIG. 6 is an integrated HPLC-ESI-MS system 600 according to an embodiment of the present invention. This diagram is merely an example, which should not unduly limit the scope of the claims herein. One of ordinary skill in the art would recognize many variations, alternatives, and modifications. As shown, the system 600 includes a plurality of electrolysis pumps 601, which are configured in parallel, on a substrate 602. Each of these electrolysis pumps is coupled to an inlet of an HPLC column 605. The HPLC column includes an outlet. Between the electrolysis pumps and column, mixer 605 is provided. Depending upon the embodiment, the mixer provides mixing of various fluids being pumped out of the electrolysis pumps. As noted HPLC column includes the outlet, which is connected to a nozzle 607. The nozzle is preferably an electrospray ionization (ESI) nozzle on the substrate having an inlet, an outlet, a micro-channel and an ESI electrode. The inlet of the ESI nozzle is coupled to the outlet of the HPLC column. The outlet of the ESI nozzle is coupled to a mass spectrometer 609, which is often outside of the substrate.

The electrochemical pump system and the ESI nozzle are configured such that the electrochemical pump system provides the driving force to push the fluid through the ESI nozzle. The fluid is emitted from the outlet of the ESI nozzle coupled to the mass spectrometer through ESI process while a high voltage source is applied between the ESI electrode and mass spectrometer according to a preferred embodiment. More preferably, the ESI electrode is contacted with the fluid pushed through the ESI nozzle. The nozzle can be made of a suitable material, e.g., Parylene, SU-8, silicone, silicon, silicon oxide, glass, Teflon, PEEK, and other polymer materials. The ESI electrode is made of a suitable material that is conductive. Such electrode material may include, among others, carbon, platinum, gold, aluminum, titanium, chromium, and other noble metals. Other embodiment of the system with the ESI nozzle is described below.

FIG. 7 is an integrated ESI-MS system 700 according to an alternative embodiment of the present invention. This diagram is merely an example, which should not unduly limit the scope of the claims herein. One of ordinary skill in the art would recognize many variations, alternatives, and modifications. As shown, the system 700 includes a plurality of electrolysis pumps 703, which are configured in parallel, on a substrate 701. Each of these electrolysis pumps is coupled to an ESI nozzle 705. The nozzle is preferably an electrospray ionization (ESI) nozzle on the substrate having an inlet, an outlet, a microchannel and an ESI electrode. The inlet of the ESI nozzle is coupled to the outlet of the electrolysis pumps. The outlet of the ESI nozzle is coupled to a mass spectrometer 709, which is often outside of the substrate.

The electrochemical pump system and the ESI nozzle are configured such that the electrochemical pump system provides the driving force to push the fluid through the ESI nozzle. The fluid is emitted from the outlet of the ESI nozzle coupled to the mass spectrometer through ESI process while a high voltage source is applied between the ESI electrode and mass spectrometer according to a preferred embodiment. More preferably, the ESI electrode is contacted with the fluid pushed through the ESI nozzle. The nozzle can be made of a suitable material, e.g., Parylene, SU-8, silicone, silicon, silicon oxide, glass, Teflon, PEEK, and other polymer materials. The ESI electrode is made of a suitable material that is conductive. Such electrode material may include, among others, carbon, platinum, gold, aluminum, titanium, chromium, and other noble metals. Other embodiment of the system with the ESI nozzle is described below.

FIG. 8 is a HPLC system with a multi-chamber arrangement for electrolysis pump. This diagram is merely an example, which should not unduly limit the scope of the claims herein. One of ordinary skill in the art would recognize many variations, alternatives, and modifications. The system 800 includes an electrochemical pump system 801 and an HPLC column 811. The HPLC column 811 is coupled to the electrochemical pump system 801 such that the electrochemical pump system 801 provides the elution or sample injection for a separation process in the HPLC column 811. The electrochemical pump system 801 includes a plurality of electrolysis pumps, such as a pump A 803 and a pump B 809. In this embodiment, the plurality of electrolysis pumps is configured in parallel. The pump A 807 includes an electrolysis chamber 805 and a solvent reservoir 807. The pump A 803 is configured such that when an electrical energy is applied to the electrolysis chamber A 805, an electrochemical reaction would increase a pressure inside the electrolysis chamber A 805, and that pressure would provide the driving force to transfer a solvent inside the solvent reservoir A 807 to the HPLC column 811. A plurality of fluids can be used in the pump A 803. The fluid inside the electrolysis chamber A 805 can be a working media for the electrochemical reaction and the fluid inside the solvent reservoir A 807 can be a solvent or sample solution for the separation process. Other electrolysis pumps can be configured in a way substantially similar to the pump A 803.

With the HPLC system as shown in FIG. 8, a method for performing liquid chromatography with a multi-chamber arrangement can be performed. The method includes applying an electrical source between a plurality of electrodes to cause an electrochemical reaction within a fluid within the electrolysis chamber A 805. The electrolysis chamber A 805 is one of a plurality of chambers. The plurality of chambers include the electrolysis chamber A 805, the electrolysis chamber B, and other electrolysis chambers. Each electrolysis chamber belongs to an electrolysis pump. As shown in FIG. 8, the electrochemical pump system 801 includes electrolysis pump A, electrolysis pump B, and other electrolysis pumps.

The method also includes generating a gaseous species from the electrochemical reaction in the fluid to increase a pressure within the electrolysis chamber A 805, and transferring a liquid chromatography fluid from the solvent reservoir A 807 to the HPLC column 811 for liquid chromatography using the first pressure associated with the electrolysis chamber A 805. Additionally, the method applies the similar processes of applying, generating, and transferring to any of the other chambers and reservoirs. Each electrolysis chamber contains a fluid, and each solvent reservoir contains a liquid chromatography fluid. As further emphasized here, the method is merely an example, which should not unduly limit the scope of the claims herein. One of ordinary skill in the art would recognize many variations, alternatives, and modifications.

It is also understood that the examples and embodiments described herein are for illustrative purposes only and that various modifications or changes in light thereof will be suggested to persons skilled in the art and are to be included within the spirit and purview of this application and scope of the appended claims. Further details of specific applications of the present invention have been described throughout the present specification and more particularly below.

Experiments:

To prove the operation of the present invention, certain experiments have been performed. These experiments are merely examples and should not unduly limit the scope of the claims herein. One of ordinary skill in the art would recognize many alternatives, variations, and modifications. These experiments were provided in reference to FIGS. 9-18 are simplified diagrams of experimental results according to embodiments of the present invention. These diagrams are merely an example, which should not unduly limit the scope of the claims herein. One of ordinary skill in the art would recognize many variations, alternatives, and modifications.

Figure 10:
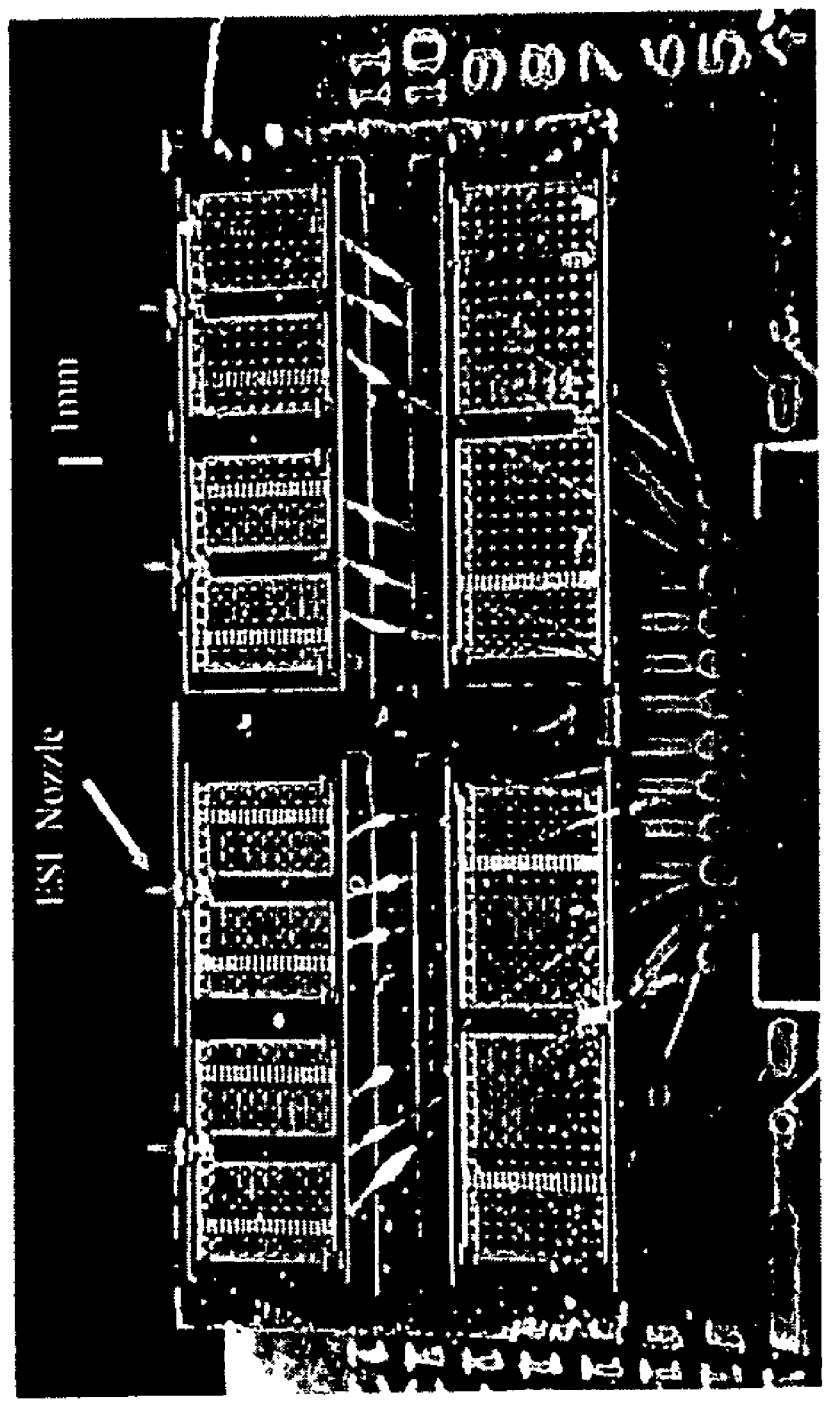
FIG. 10 illustrates a fabricated ESI device with integrated electrochemical pumping.

The technique of HPLC-ESI-MS, which is a combination of two powerful standalone analytical techniques, is an exciting development of recent times in analytical methodology. Although certain analytical applications of High-Performance Liquid Chromatography (HPLC) and MS have established, we have successfully made a polymer-based electro spray chips for mass spectrometry. Electrochemical micro actuation based on electrolysis has been demonstrated as a successful technique for microfluidic application. But usually the device involves relatively complicated packaging, such as wafer bonding. Here, we made an electrolysis-based micro pump using the Parylene surface micromachining technology we developed. With this technology, an electrolysis micro pump, a passive micro mixer, and an ESI nozzle have all been integrated on a single chip. No external fluidic coupling is needed. Samples are stored and sealed in reservoir, then are pumped out by bubble pressure generated by electrolysis. After mixing at micro mixer, samples are fed to MS inlet through an integrated ESI nozzle. This stand-alone system does not need complicated packaging and only electrical wire is connected to the chip. That simplifies the operation of this system. Operation principle and fabricated device are shown in FIGS. 9 and 10.

An important application for this integrated system is on-chip gradient elution. For most complex analyses in HPLC, gradient elution is required. In most cases, the gradient systems involve multiple solvent reservoirs, pumps and mixers. Certain components have already been integrated using the proposed method. The gradient flow rate, concentration ratio or gradient slope, and duration can all be controlled electrically by adjust the voltage or current applied to the electrolysis pumps whose chambers contain different fluids. There are other approaches to achieve the same functions. For example, the pumping can use, but not limit to, electrostatic pump, thermo pneumatic pump, electro hydrodynamic pump, electro osmotic or electrophoretic pump. Electrostatic actuation based pump has already under the study in our group. The mixer can be an active mixer using the similar actuation methods as the pump, such as electrostatic, acoustic or dielectrophoretic actuation. Other applicable materials can also be used. For example other polymers, such as PDMS, etc., or more traditional MEMS materials, such as polysilicon or metal. Fabrication methods are described in more detail below.

Figure 11:
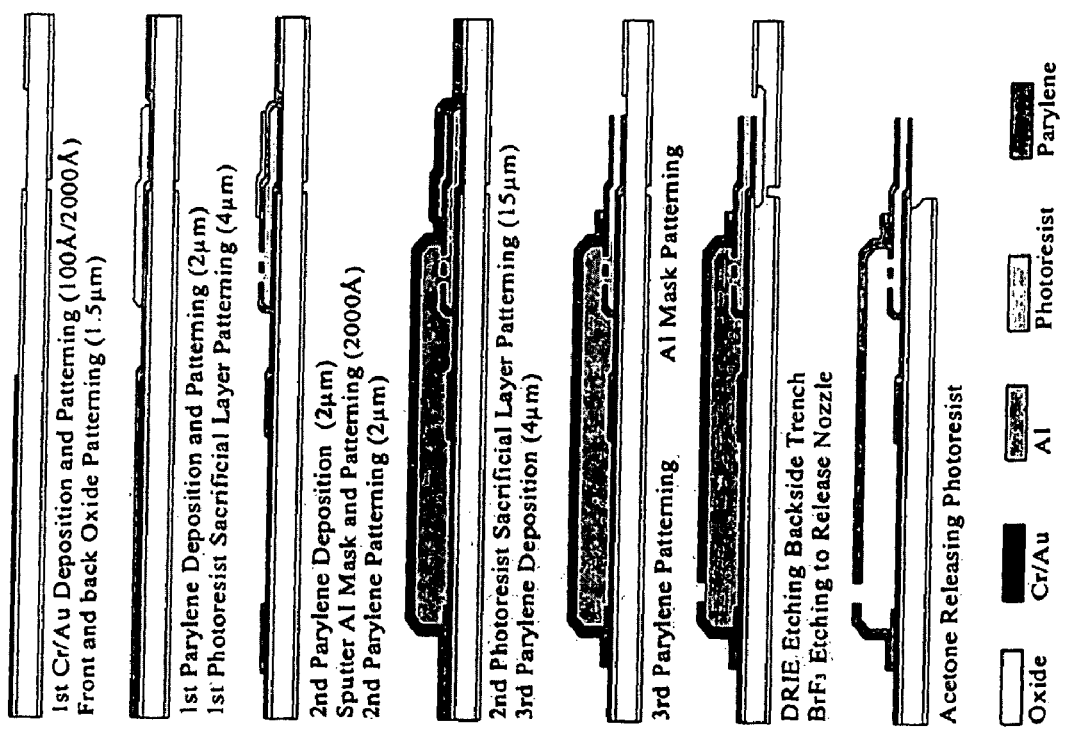
FIG. 11 presents a process flow for making of the ESI device with integrated electrochemical pumping.
Figure 12:
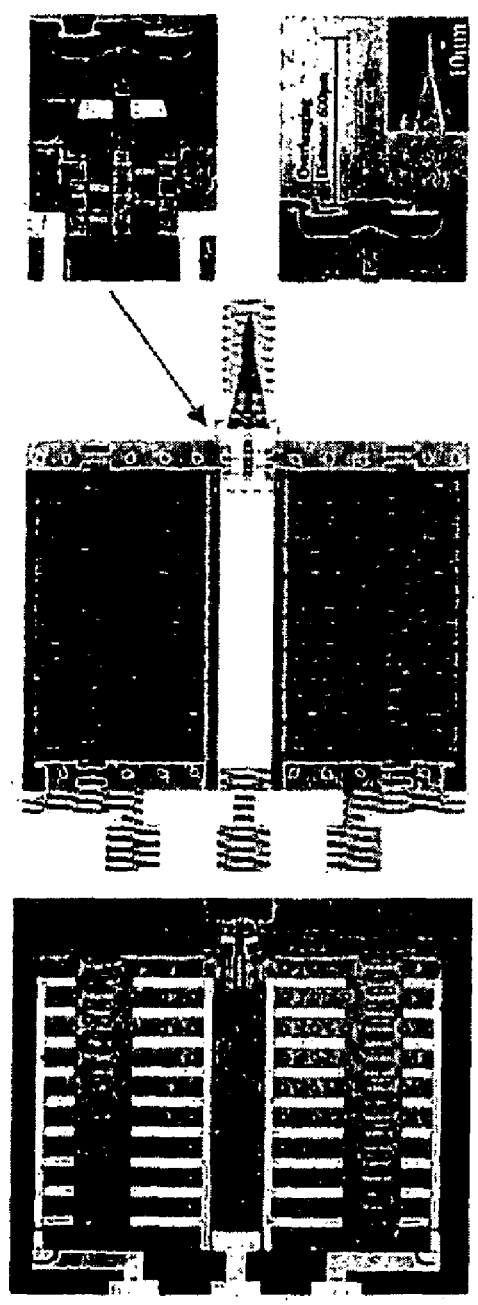
FIG. 12 shows details of pump, mixer and ESI nozzle in fabricated ESI device with integrated electrochemical pumping.

The device is fabricated by multi-layer Parylene surface micromachining technology. Process starts with oxide-coated silicon substrate. Electrodes for electrolysis are formed by Cr/Au (100 Å/2000 Å) layers. Then oxide on both sides is patterned to form $BrF_3$ and DRIE masks. The micro nozzle and mixer are constructed by one 4 micron photoresist sacrificial layer sandwiched by two 2 micron Parylene layers. A 2000 Å Al is patterned as Parylene mask to create sharp ESI nozzle. The reservoir is formed by a 15 micron photoresist sacrificial layer and 4 micron Parylene layer. Freestanding nozzle is created by etching away the silicon underneath using $BrF_3$. A trench by DRIE etching makes it easy to break the chip, so the nozzle overhangs out 600 microns. Finally, sacrificial layer is released by Acetone with ultrasonic stirring and followed by Methanol and DI water cleaning. FIG. 11 shows the detailed process flow. FIG. 12 gives simplified pictures about the micro pump, mixer and nozzle.

Figure 13:
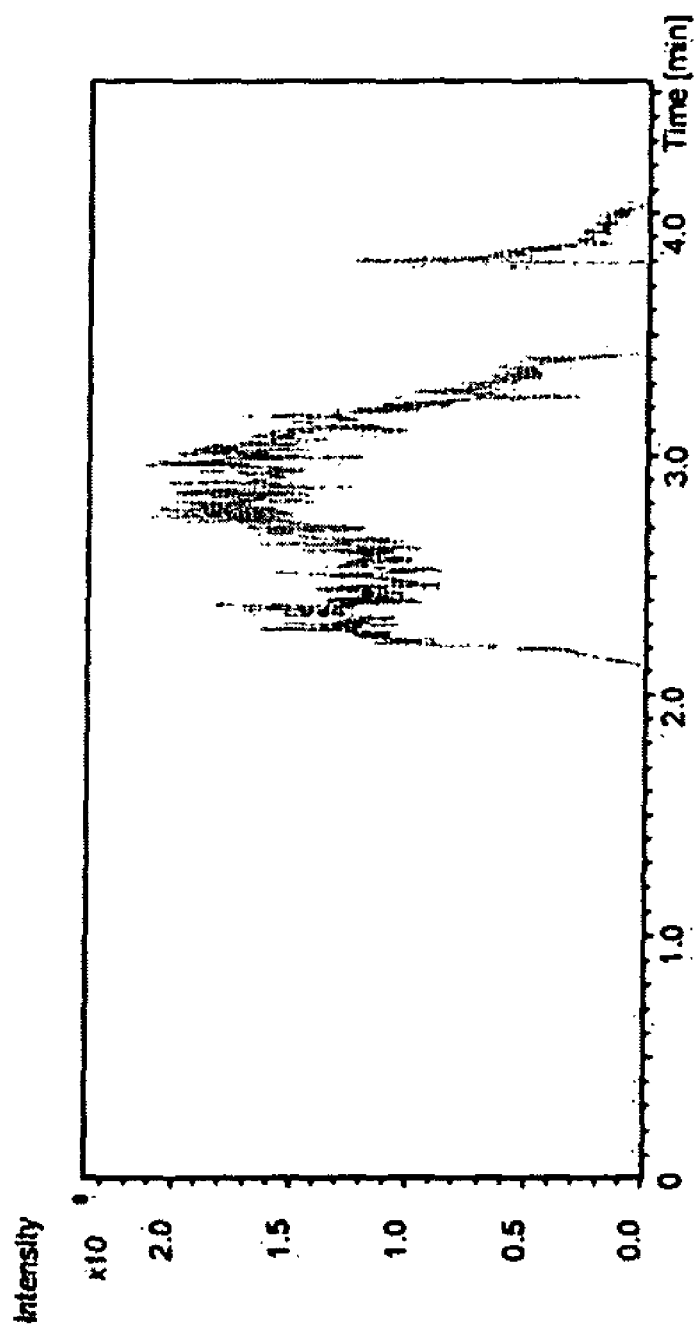
FIG. 13 shows ion intensity as a function of time.
Figure 14:
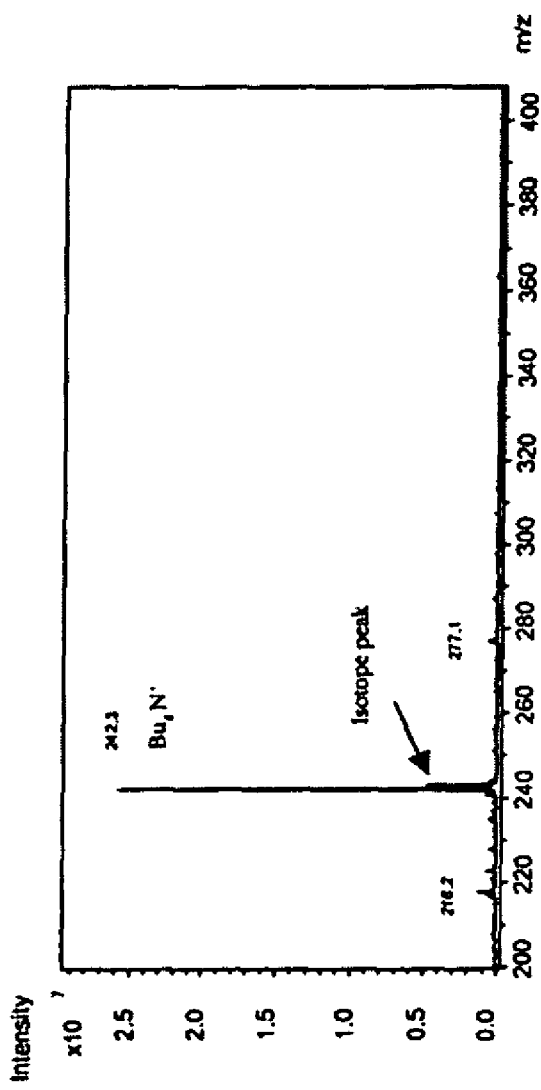
FIG. 14 shows ion intensity as a function of m/z.
Figure 15:
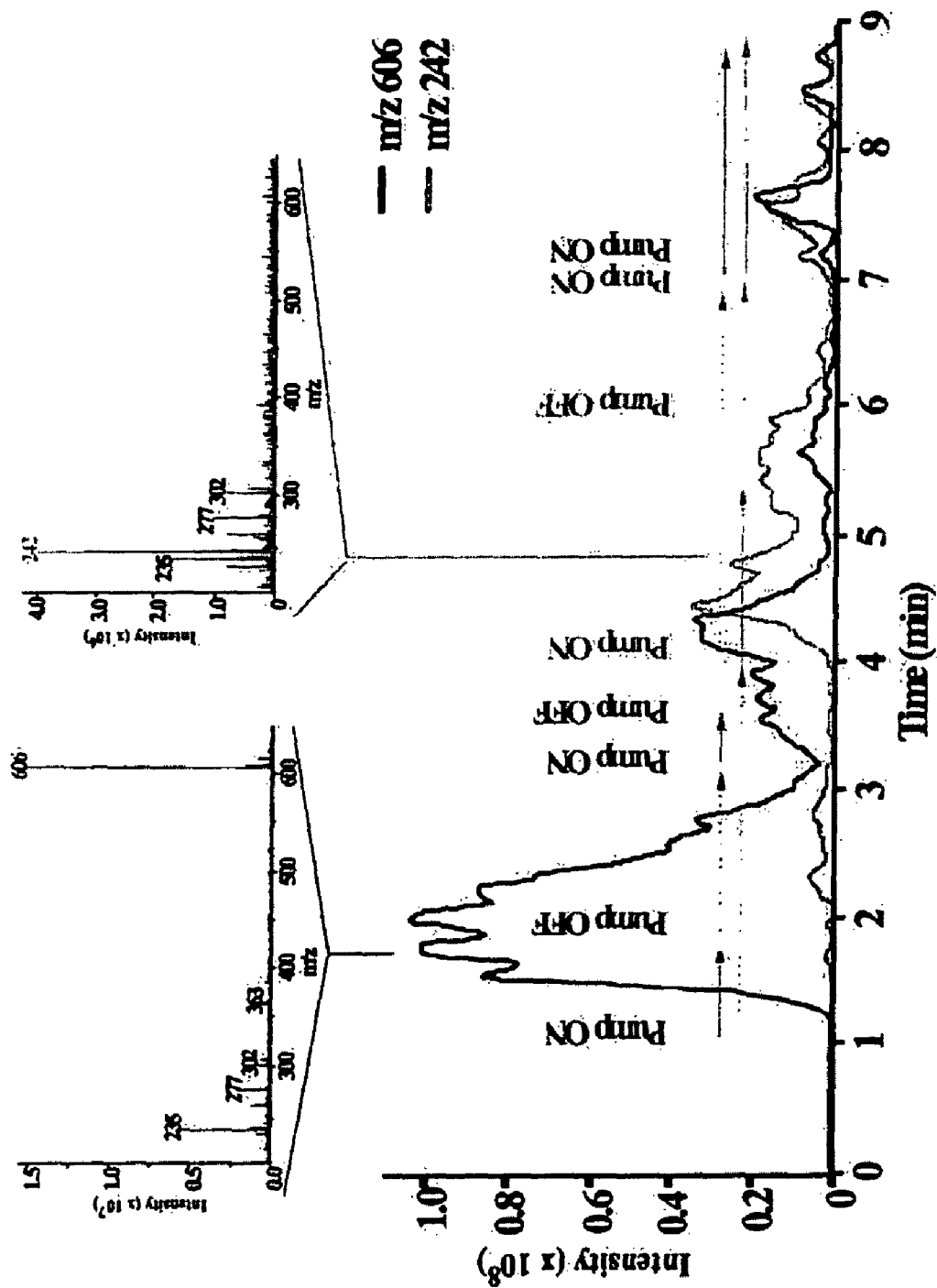
FIG. 15 shows results of multisample analysis.

During testing, water-based solution containing 5% Methanol, 5% Acetic Acid and target sample (50 pmol/µL tetrabutyl ammonium iodide) was used. Sample solution was dropped onto inlet and photoresist was used to seal the inlet after the surface tension filled the reservoir (about 100 nL) with the solution. Then the chip was placed in front of MS inlet. An electrolysis voltage was applied along with a high voltage for ESI. FIGS. 13 and 14 present the result from the actual MS data using this integrated fluid dispensing system. Before the electrolysis voltage was applied there was no electro spray which means no signal. After electrolysis happened, the expected isotope peak of $Bu_4N^+$ was observed in the mass spectrum. The flow rate is estimated to be around 80 nL/min. To further demonstrate the capability of this system, a multi-sample analysis has been done as shown in FIG. 15. Two different target samples were stored in the two reservoirs that are connected by mixer. Then by controlling the electrolysis voltage applied to each reservoir, we could control which sample solutions was fed into the nozzle and then finally got electro sprayed into MS. One chamber was filled with Tetrabutyl ammonium iodide (25 pmol/µl, m/z 242 marked as green line) and the other chamber with a peptide called leuprolide (30-50 pmolmu.l, m/z 606 marked as red line). Both samples were dissolved in 5% methanol and 5% acetic acid. FIG. 15 shows the ion chromatograms for each sample and representative mass spectra at the times indicated. The experiments demonstrated the effectiveness of electrolysis micro pump, performance of the whole system and the essential idea of on-chip gradient elution.

An on-chip integrated microfluidic system for Mass Spectrometry (MS) is proposed and developed. The basic concept and design is discussed. One method of realization has been demonstrated which used multi-layer Parylene surface micromachining to achieve total integration of various microfluidic components, such as electrolysis-based micro pump, micro mixer and electro spray ionization (ESI). The application of proposed system includes multi-source precise dispensing and gradient elution for HPLC-ESI-MS system.

Figure 17:
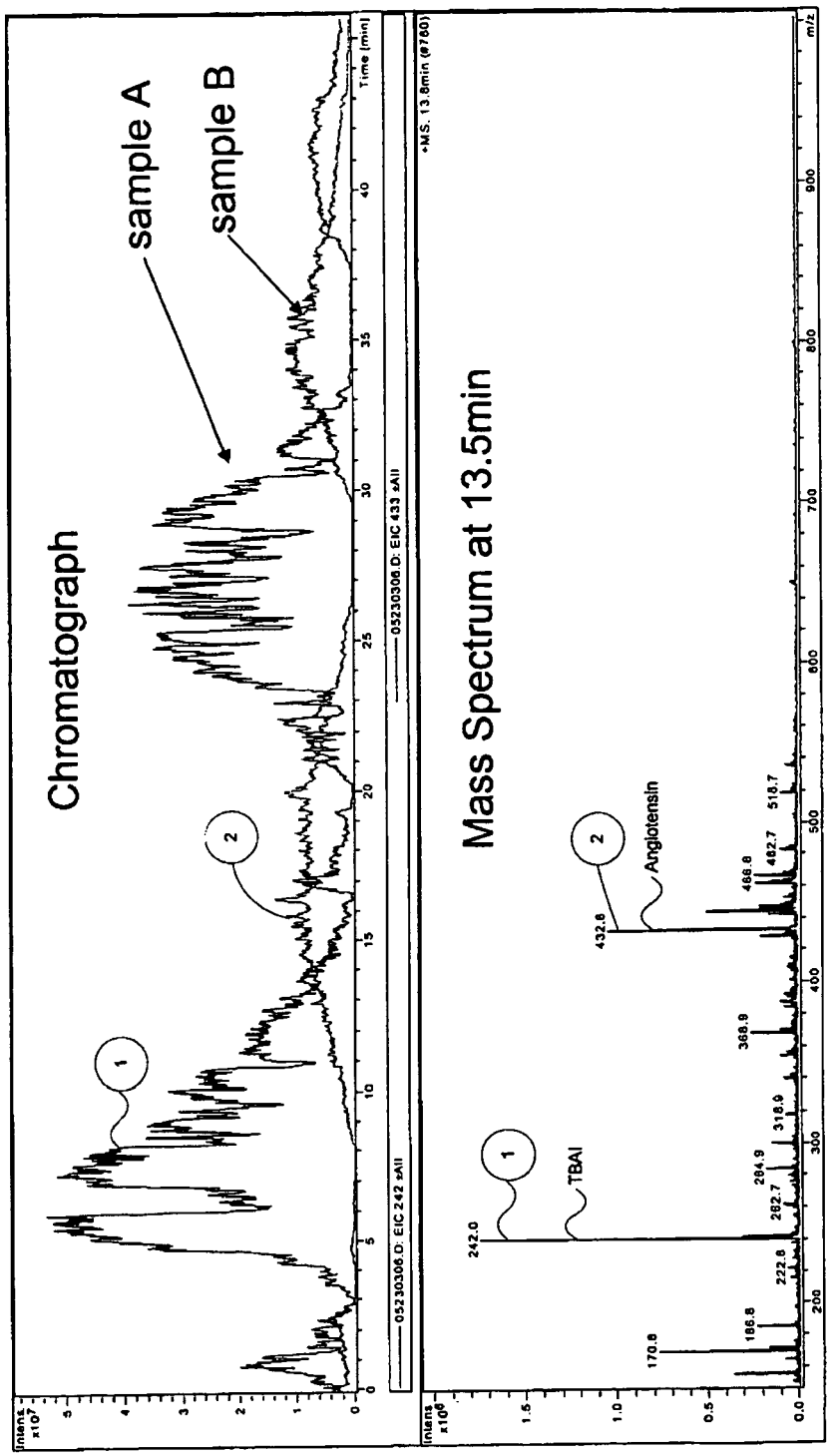
FIG. 17 presents data obtained for a chip with two electrolysis pumps coupled to an ESI nozzle.
Figure 18:
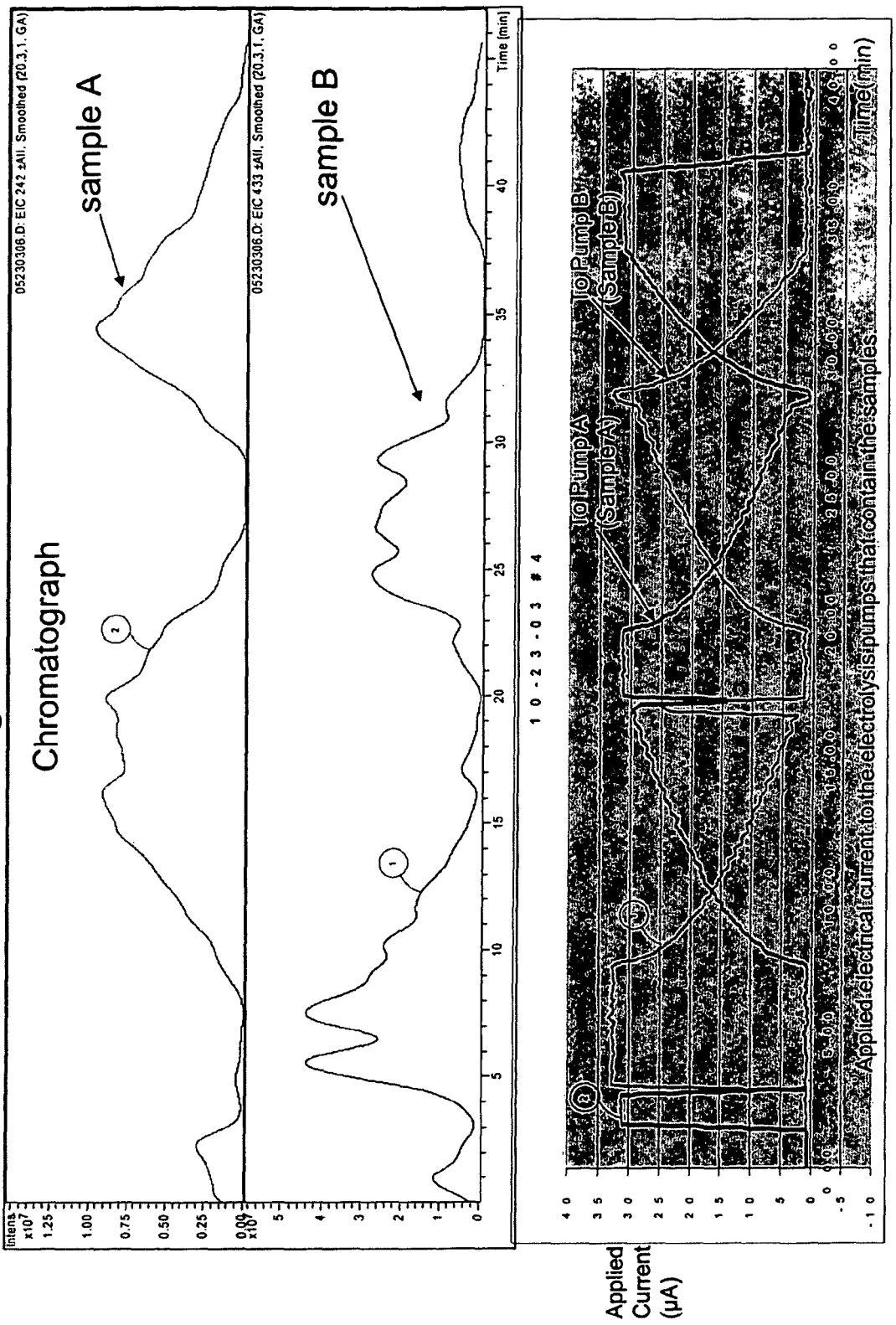
FIG. 18 illustrates a gradient formation using a chip with two electrolysis pumps interfaced with a ion trap mass spectrometer.

The present invention has also been demonstrated using a multiple pump configuration as illustrated by way of FIGS. 16 through 18. Referring to FIG. 16, a single chip design including two electrolysis chambers (as pumps) coupled to an ESI nozzle were disposed on the substrate. Each of the chambers included a plurality of electrodes that were coupled to external power sources. Each of the power sources were operated independently to demonstrate the present system and method. As merely an example, one of the chambers is provided with 10 pmol/µL TBAI in 90/10/0.1 water/acetonitrile/formic acid. The other chamber is provided with 25 pmol/µL Angiotensin in 95/5/0.2 water/methanol/formic acid. As can be seen, each of the pumps is actuated with its selected fluid and the fluid has been outputted. The mass spectrophotometer reads the fluid outputted from the nozzle. TBAI was illustrated by a first peak and Angiotensin was illustrated by a second peak, which has been plotted against intensity in FIG. 17. Fluid flow can be individually controlled in response to the electrical current applied to the corresponding pumps and independent from each other, as also illustrated in FIG. 18 by the blue (reference numeral 1) and red (reference numeral 2) plots. Accordingly, we demonstrated accurate control over the output and distribution of the fluid from each of the chambers.

Referring to FIG. 18, we plotted current in micro amperes along a vertical axis, which intersects with a time axis. Current has been applied to one of the chambers to pump fluid there from, as represented by the red line (reference numeral 2), and then shut off, and on again. A counter current was provided on the other chamber, while the first chamber is turned off, as also illustrated. The mass spectrometer detects each of the fluids, which correspond also to the red line and blue line. Remarkably, control over output of the fluid is highly predictable and controllable by way of the present system and method. Of course, one of ordinary skill in the art would recognize other variations, modifications, and alternatives.

It is also understood that the examples and embodiments described herein are for illustrative purposes only and that various modifications or changes in light thereof will be suggested to persons skilled in the art and are to be included within the spirit and purview of this application and scope of the appended claims.

Other embodiments include embodiments 1-88 summarized below (and claimed in priority patent publication 2004/0124085):

Embodiment 1. A microfluidic system for liquid chromatography, the system comprising: a substrate; an electrochemical pump system on the substrate, the electrochemical pump system comprising a plurality of electrolysis pumps and having at least one outlet; each of the electrolysis pumps comprising: a chamber; a plurality of electrodes, the electrodes being coupled to an electrical source; a fluid inside the chamber, and the fluid being contacted with the electrodes; and an inlet and an outlet; an separation column on the substrate having an inlet and an outlet, an micro channel, a solid stationary phase material packed inside the micro channel, the inlet of the separation column being coupled to the at least one outlet of the electrochemical pump system; and wherein the electrochemical pump system and the separation column are configured such that the electrochemical pump system provides an elution for a separation process inside the separation column.

Embodiment 2. The system of embodiment 1 wherein the plurality of electrolysis pumps are configured in parallel.

Embodiment 3. The system of embodiment 1 wherein the plurality of electrolysis pumps are configured in serial.

Embodiment 4. The system of embodiment 1 wherein the plurality of electrolysis pumps are configured in parallel and serial.

Embodiment 5. The system of embodiment 1 wherein the elution provided by the electrochemical pump system is isocratic elution.

Embodiment 6. The system of embodiment 1 wherein the elution provided by the electrochemical pump system is gradient elution.

Embodiment 7. The system of embodiment 1 wherein one of the electrolysis pumps is a sample injector and wherein the separation column is configured to perform a separation of one or more components of the sample dispensed from the sample injector as the rest of electrolysis pumps provide the elution for the separation column.

Embodiment 8. The system of embodiment 1 further comprising: a sample source, the sample source comprising a sample; an sample injector on the same substrate coupled between the electrochemical pump and the separation column, the sample injector being coupled to the sample source; and wherein the separation column is configured to perform a separation of one or more components of the sample dispensed from the sample injector as the electrochemical pump system provides the elution for the separation column.

Embodiment 9. The system of embodiment 1 wherein the electrical source is selected from a group consisting of a voltage source, a current source, and a voltage/current source.

Embodiment 10. The system of embodiment 1 wherein the electrolysis pump is adapted to maintain a pressure on the fluid in the chamber while the electrodes are biased using the electrical source.

Embodiment 11. The system of embodiment 10 wherein the pressure is greater than 1000 psia.

Embodiment 12. The system of embodiment 10 wherein the pressure is less than 1000 psia.

Embodiment 13. The system of embodiment 10 wherein the pressure is less than 100 psia.

Embodiment 14. The system of embodiment 1 wherein the chamber comprises about 1 micro liter of fluid.

Embodiment 15. The system of embodiment 1 wherein the chamber comprises greater than about 1 micrometer of fluid.

Embodiment 16. The system of embodiment 1 wherein the chamber comprises less than about 1 micrometer of fluid.

Embodiment 17. The system of embodiment 1 wherein the electrochemical pump system is characterized to provide a flow rate of about 1 nanoliter per minute to about 1 micro liter per minute through the separation column.

Embodiment 18. The system of embodiment 1 wherein the electrochemical pump system is characterized to provide a flow rate of less than about 1 nanoliter per minute through the separation column.

Embodiment 19. The system of embodiment 1 wherein the electrochemical pump system is characterized to provide a flow rate of greater than about 1 micro liter per minute through the separation column.

Embodiment 20. The system of embodiment 1 wherein the chamber and the separation column are made of materials including Parylene.

Embodiment 21. The system of embodiment 1 wherein the chamber and the separation column are made of materials selected from a group consisting of SU-8, silicone, silicon, silicon oxide, glass, Teflon, PEEK, and other polymer materials.

Embodiment 22. The system of embodiment 1 wherein the electrodes are made of at least a material selected from a group consisting of carbon, platinum, gold, aluminum, titanium, chromium, and other noble metals.

Embodiment 23. The system of embodiment 1 wherein the fluid being an electrolyte that is selected from a group consisting of organic liquid, inorganic liquid, or a combination of inorganic liquid and organic liquid.

Embodiment 24. The system of embodiment 23 wherein the organic liquid is selected from a group consisting of acetonitrile, methanol, ethanol, tetrahydrofuran, isopropanol, and toluene.

Embodiment 25. The system of embodiment 1 wherein the electrolysis pump further comprising a plurality of chambers configured in series and containing same or different fluid inside each chamber.

Embodiment 26. The system of embodiment 1 further comprising a mixer on the same substrate coupled between the electrochemical pump system and the separation column, the mixer is configured such that different components of the elution provided by the electrochemical pump system are mixed with each other before entering the separation column.

Embodiment 27. The system of embodiment 1 wherein the electrochemical pump system and the separation column are disposed on the separated substrate with a fluidic connection between the electrochemical pump system and the separation column and are configured such that the electrochemical pump system provides the elution for the separation process inside the separation column.

Embodiment 28. The system of embodiment 1 further comprising a nozzle coupled to the separation column through the outlet of the separation column, the nozzle being adapted to output one or more separated components in a sequential order.

Embodiment 29. The system of embodiment 28 wherein the nozzle being coupled to transfer the one or more separated components to a mass spectrometry process using an electrospray ionization process.

Embodiment 30. The system of embodiment 1 further comprising a detection device coupled to separation column through the outlet of the separation column.

Embodiment 31. The system of embodiment 30 wherein the detection device being disposed on the same substrate with the separation column.

Embodiment 32. The system of embodiment 30 wherein the detection device is selected from a group consisting of a UV analyzer, a conductivity analyzer, a refractive index analyzer, a fluorescence analyzer, an electrochemical analyzer, a light scattering analyzer, and a mass spectrometer.

Embodiment 33. The system of embodiment 1 wherein the electrochemical pump system and the separation column are constructed from at least one selected from a group consisting of multi-chip packaging, injection molding, photolithography, dry etching, wet etching, evaporation, sputtering, and chemical vapor deposition.

Embodiment 34. A microfluidic system for electrospray ionization (ESI) and mass spectrometry (MS), the system comprising: a substrate; an electrochemical pump system disposed on the substrate, the electrochemical pump system comprising a plurality of electrolysis pumps and having at least one outlet; each of the electrolysis pumps comprising: a chamber; a plurality of electrodes, the electrodes being coupled to an electrical source; a fluid inside the chamber, and the fluid being contacted with the electrodes; and an inlet and an outlet; an electrospray ionization (ESI) nozzle disposed on the substrate, the ESI nozzle having an inlet, an outlet, a micro channel coupled between the inlet and the outlet, and an ESI electrode within the micro channel; the inlet of the ESI nozzle being coupled to the outlet of the electrochemical pump system; a mass spectrometer, the mass spectrometer including an inlet, the inlet being coupled to the outlet of the ESI nozzle; wherein the electrochemical pump system and the ESI nozzle are configured such that the electrochemical pump system provides a driving force to cause the fluid to flow through the micro channel of the ESI nozzle and flow out through the outlet of the ESI nozzle; and the fluid emitted from the outlet of the ESI nozzle is transferred to the mass spectrometer as a voltage source is applied between the ESI electrode and the mass spectrometer.

Embodiment 35. The system of embodiment 34 wherein the plurality of electrolysis pumps are configured in parallel.

Embodiment 36. The system of embodiment 34 wherein the plurality of electrolysis pumps are configured in serial.

Embodiment 37. The system of embodiment 34 wherein the plurality of electrolysis pumps are configured in parallel and serial.

Embodiment 38. The system of embodiment 34 wherein the electrical source is selected from a group consisting of a voltage source, a current source, and a voltage/current source.

Embodiment 39. The system of embodiment 34 wherein the electrolysis pump is adapted to maintain a pressure on the fluid in the chamber while the electrodes are biased using the electrical source.

Embodiment 40. The system of embodiment 39 wherein the pressure is less than 1000 psia.

Embodiment 41. The system of embodiment 39 wherein the pressure is less than 100 psia.

Embodiment 42. The system of embodiment 34 wherein the chamber comprises about 1 micro liter of fluid.

Embodiment 43. The system of embodiment 34 wherein the chamber comprises greater than about 1 micrometer of fluid.

Embodiment 44. The system of embodiment 34 wherein the chamber comprises less than about 1 micrometer of fluid.

Embodiment 45. The system of embodiment 34 wherein the electrochemical pump system is characterized to provide a flow rate of about 1 nanoliter per minute to about 1 micro liter per minute through the separation column.

Embodiment 46. The system of embodiment 34 wherein the electrochemical pump system is characterized to provide a flow rate of less than about 1 nanoliter per minute through the separation column.

Embodiment 47. The system of embodiment 34 wherein the electrochemical pump system is characterized to provide a flow rate of greater than about 1 micro liter per minute through the separation column.

Embodiment 48. The system of embodiment 34 wherein the chamber and the ESI nozzle are made of materials including Parylene.

Embodiment 49. The system of embodiment 34 wherein the chamber and the ESI nozzle are made of materials selected from a group consisting of SU-8, silicone, silicon, silicon oxide, glass, Teflon, PEEK, and other polymer materials.

Embodiment 50. The system of embodiment 34 wherein the electrodes of the electrolysis pumps and the ESI electrode are made of at least a material selected from a group consisting of carbon, platinum, gold, aluminum, titanium, chromium, and other noble metals.

Embodiment 51. The system of embodiment 34 wherein the fluid being an electrolyte that is selected from a group consisting of organic liquid, inorganic liquid, or a combination of inorganic liquid and organic liquid.

Embodiment 52. The system of embodiment 51 wherein the organic liquid is selected from a group consisting of acetonitrile, methanol, ethanol, tetrahyrdrofuran, isopropanol, and toluene.

Embodiment 53. The system of embodiment 34 wherein the electrolysis pump further comprising a plurality of chambers configured in series and containing same or different fluid inside each chamber.

Embodiment 54. The system of embodiment 34 further comprising a mixer on the same substrate coupled between the electrochemical pump system and the ESI nozzle, the mixer is configured such that different fluids injected from the electrochemical pump system are mixed with each other before entering the ESI nozzle.

Embodiment 55. The system of embodiment 34 wherein the electrochemical pump system and the ESI nozzle are disposed on the separated substrate with a fluidic connection between the electrochemical pump system and the ESI nozzle and are configured such that the electrochemical pump system provides the driving force to push the fluid through the ESI nozzle, and the fluid emitted from the outlet of the ESI nozzle is transferred to the mass spectrometer as a voltage source is applied between the ESI electrode and the mass spectrometer.

Embodiment 56. The system of embodiment 34 wherein the electrochemical pump system and the ESI nozzle are constructed from at least one selected from a group consisting of multi-chip packaging, injection molding, photolithography, dry etching, wet etching, evaporation, sputtering, and chemical vapor deposition.

Embodiment 57. A method for transferring fluid on a microfluidic chip based on an electrochemical actuation, the method comprising: transferring a fluid into a chamber through an inlet within a substrate; providing an electrical connection using a plurality of electrodes coupled to the chamber; transferring a portion of the fluid from the chamber through an outlet while applying an electrical energy to the plurality of electrodes using the electrical connection, whereupon the portion of the fluid is transferred free from any coupling to an external fluidic source; wherein the transferring a portion of the fluid is performed in response to the electrical energy applied to the plurality of electrodes.

Embodiment 58. The method of embodiment 57 further comprising using the portion of the fluid for a separation process.

Embodiment 59. The method of embodiment 57 further comprising transferring the portion of the fluid through a nozzle.

Embodiment 60. The method of embodiment 57 further comprising sealing the fluid in the chamber.

Embodiment 61. The method of embodiment 57 further comprising isolating the fluid in the chamber.

Embodiment 62. The method of embodiment 57 wherein the transferring of the portion of the fluid is provided only by applying the electrical energy to the microfluidic chip.

Embodiment 63. A method for controlling fluid through a microfluidic system in a liquid chromatography application, the method comprising: transferring fluid from an inlet into a chamber, the chamber being formed on a first portion of a substrate, the chamber comprising a plurality of electrodes, the plurality of electrodes being configured to apply electrical forces to the fluid; applying an electrical source between the plurality of electrodes; causing an electrochemical reaction within the chamber based upon the application of the electrical source onto the electrodes, the electrodes being coupled to the fluid; and generating a gaseous species from the electrochemical reaction to increase a pressure within the chamber; coupling a separation column to the chamber; using the pressure in the chamber to provide driving force for the elution in the separation column for liquid chromatography; and controlling the elution by adjusting the electrical source that applied the plurality of electrodes.

Embodiment 64. The method of embodiment 63 wherein the electrical forces comprise an electrical current.

Embodiment 65. The method of embodiment 63 wherein the electrical forces comprise a voltage.

Embodiment 66. The method of embodiment 63 wherein the elution being isocratic.

Embodiment 67. The method of embodiment 63 wherein the elution being gradient.

Embodiment 68. The method of embodiment 63 wherein the pressure in the chamber also provide driving force for a sample injection in the separation process.

Embodiment 69. The method of embodiment 63 further comprising capturing a signal associated with a parameter of the fluid in the chamber; and using the captured signal to adjust a level of the electrical source between the plurality of electrodes.

Embodiment 70. The method of embodiment 63 wherein the fluid in the chamber is a first fluid and the separation column comprises a second fluid, the first fluid being different from the second fluid, whereupon the second fluid being separated into one or more components as the second fluid passes through the separation column.

Embodiment 71. The method of embodiment 63 further comprising transferring the one or more components in a sequential manner from the separation column through a nozzle, the nozzle being coupled to the separation column.

Embodiment 72. A method for controlling fluid through a microfluidic system in a liquid chromatography application, the method comprising: applying an electrical source between a plurality of electrodes to cause an electrochemical reaction within a first fluid in a chamber coupled to the plurality of electrodes; generating a gaseous species from the electrochemical reaction in the first fluid to increase a pressure within the chamber; and transferring a second fluid through a separation column using the pressure associated with the chamber for liquid chromatography.

Embodiment 73. The method of embodiment 72 wherein the first fluid is a working media for the electrochemical reaction and the second fluid is a solvent for liquid chromatography.

Embodiment 74. The method of embodiment 72 further comprising transferring the one or more components in a sequential manner from the separation column through a nozzle, the nozzle being coupled to the separation column.

Embodiment 75. A method for performing liquid chromatography using a multichamber arrangement, the method comprising: applying an electrical source between a plurality of electrodes to cause an electrochemical reaction within a first fluid in a first chamber, the first chamber being among a plurality of chambers, each of the chambers being numbered from 1 through N, where N is an integer greater than 1, the first fluid being from a plurality of fluids numbered from 1 through N, each of the fluids being respectively associated with each of the chambers; generating a gaseous species from the electrochemical reaction in the first fluid to increase a first pressure within the first chamber; transferring a first liquid chromatography fluid from a first reservoir to a separation column for liquid chromatography using the first pressure associated with the first chamber, the first liquid chromatography fluid being from a plurality of liquid chromatography fluids numbered from 1 through N, each of the liquid chromatography fluids being associated with a respective reservoir also numbered from 1 through N; and applying, generating, and transferring for any of the other chambers including any of the other respective fluids and reservoirs.

Embodiment 76. The method of embodiment 75 wherein the first fluid is a working media for the electrochemical reaction and the first liquid chromatography fluid is for liquid chromatography.

Embodiment 77. The method of embodiment 75 wherein the applying, generating, and transferring for the first chamber is performed simultaneously with steps of applying, generating, and transferring for any of the other chambers.

Embodiment 78. The method of embodiment 75 wherein the applying, generating, and transferring for the first chamber is performed sequentially with steps of applying, generating, and transferring for any of the other chambers.

Embodiment 79. The method of embodiment 75 wherein each of the fluids numbered from 1 through N is a similar substance.

Embodiment 80. The method of embodiment 75 wherein each of the liquid chromatography fluids numbered from 1 through N is a similar substance.

Embodiment 81. A method for controlling fluid through a microfluidic system for ESIMS, the method comprising: transferring a first fluid from an inlet into a chamber, the chamber being formed on a first portion of a substrate, the chamber comprising a plurality of electrodes, the plurality of electrodes being configured to apply electrical forces to the first fluid; applying an electrical source between the plurality of electrodes; causing an electrochemical reaction within the chamber based upon the application of the electrical source onto the electrodes, the electrodes being coupled to the first fluid; and generating a gaseous species from the electrochemical reaction to increase a pressure within the chamber, the chamber being coupled to an ESI nozzle; using the pressure in the chamber to provide a driving force to cause an injection at a certain rate of a second fluid through the ESI nozzle for use in a mass spectrometer; controlling the rate of the injection by adjusting an electrical source coupled to the plurality of electrodes.

Embodiment 82. The method of embodiment 81 wherein the electrical forces comprise an electrical current.

Embodiment 83. The method of embodiment 81 wherein the electrical forces comprise a voltage.

Embodiment 84. The method of embodiment 81 further comprising capturing a signal associated with a parameter of the first fluid in the chamber; and using the captured signal to adjust a level of the electrical source between the plurality of electrodes.

Embodiment 85. The method of embodiment 81 wherein the first fluid from the inlet into the chamber is different from the second fluid through the ESI nozzle, whereupon the second fluid being coupled to a MS through ESI process as the second fluid being injected from the ESI nozzle and a voltage source being applied between the ESI nozzle and the MS.

Embodiment 86. The method of embodiment 81 wherein the first fluid from the inlet into the chamber is the same as the second fluid through the ESI nozzle, whereupon the second fluid being coupled to a MS through ESI process as the second fluid being injected from the ESI nozzle and a voltage source being applied between the ESI nozzle and the MS.

Additional Description

Priority U.S. Provisional Application No. 60/586,576 filed Jul. 9, 2004, "Integrated LC-ESI on a Chip", is incorporated hereby by reference in its entirety including the nine figures, working examples, and sections on design and analysis, gradient pump and sample injector, passive mixer, reversed phase column, ESI nozzle, fabrication, chip design and packaging, fabrication process, experimental results, testing set up, commercial LC-MS system, chip performance, comparison, other chip testing, and conclusions.

In addition, the following publication is hereby incorporated by reference in its entirety, including Figures and sections on Introduction, Design, Fabrication, Results, Conclusions, and References: J. Xie et al., "Complete Gradient-LC-ESI System on a Chip for Protein Analysis," Proceedings/Technical Digest from the $18^{th}$ IEEE International Conference on MicroElectroMechanical Systems (MEMS 2005), Miami, Fla., USA, January, 2005.

Additional embodiments are provided which generally relate to microfluidics. In particular, additional embodiments provide a microfluidic liquid chromatography (LC)—electrospray ionization (ESI) system which has important components integrated on a chip. The additional embodiments also provide methods of using and methods of making of the microfluidic LC-ESI system.

One embodiment of the present invention (see FIG. 19; see also FIG. 1) is a microfluidic system for liquid chromatography (LC)/electrospray ionization (ESI) mass spectrometry (MS) comprising a main chip, said main chip comprises a substrate having a front surface and a back face, a chromatography column having an inlet and an outlet and an electrospray ionization nozzle having an inlet and an outlet. The chromatography column and the ESI nozzle can be both fabricated on the front surface of the substrate. The outlet of the chromatography column can be microfluidically coupled to the inlet of the ESI nozzle.

The microfluidic device can further comprise one or more pump systems microfabricated on the front surface of the substrate. Each of the pump systems can have at least one outlet microfluidically coupled to the inlet of said column.

Each of the pump systems can include elements such as a chamber, a plurality of electrodes, which are coupled to an electrical source, a fluid inside the chamber, and an inlet and an outlet. The pump systems can comprise gradient pump systems used for creating a gradient elution of a mobile phase pumped through the chromatography column. The pump systems can also comprise an injection pump systems used for a sample injection. The gradient pump systems can include a aqueous pump system for pumping aqueous solvent for gradient elution and an organic pump system for pumping organic solvent for gradient elution.

Figure 33:
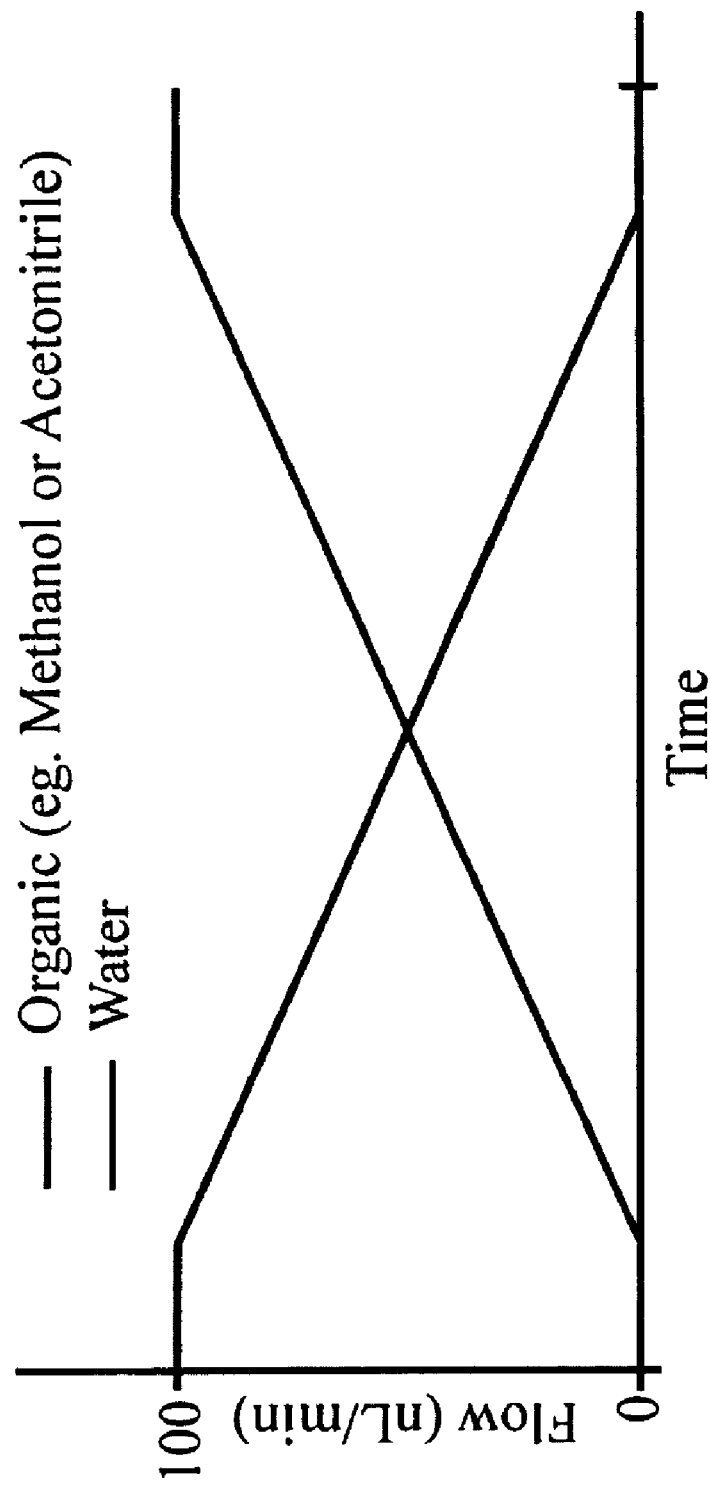
FIG. 33 shows a constant flow rate linear gradient going from 0% organic to 100% organic.

The gradient elution can be carried out as part of a reverse phase (RP) liquid chromatography. The gradient elution can be created in a mixture of polar, e.g. aqueous, and non-polar, e.g. organic such as acetonitrile, methanol or propanol, solvents. The elution can usually start at a high aqueous concentration and gradually change to high organic concentration. For example, FIG. 33 illustrates a constant flow linear gradient going from 0% to 100% organic. Typical applications can, if desired, only employ swings from 0% to 50-70% depending on the type of sample and organic solvent being used. The gradient elution can allow one to separate analytes based on their hydrophobicity. The gradient elution can be particularly useful when components of a sample exhibit a very large range of hydrophobicity, which can be often a case in proteomics.

Figure 25:
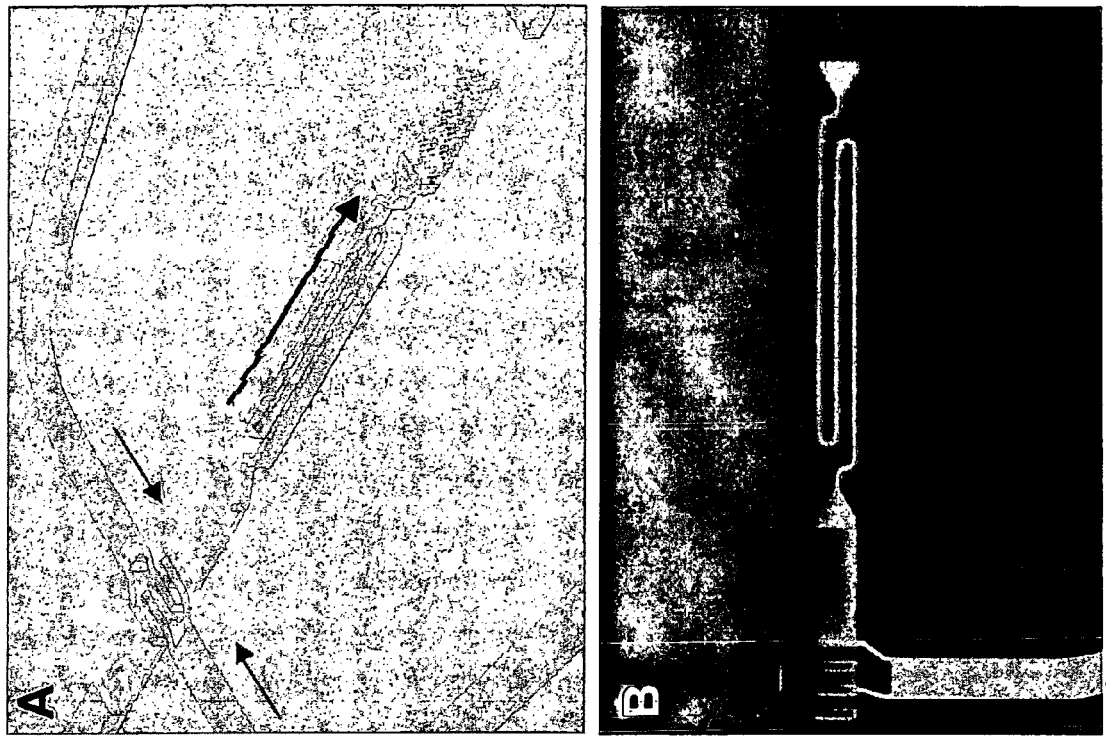
FIG. 25 illustrates a design of the static mixer of the microfluidic device for on-chip LC-ESI.

In some embodiments, the gradient pumps can be connected to the inlet of the chromatography column through a mixer. Mixers can be active or passive. In the mixer, solvents in the gradient elution can be well mixed before entering the chromatography column. The mixer can comprise a junction where flows of solvents from the gradient pumps can come together. The mixer can further comprise a mixing channel as illustrated in FIG. 25A. Mixing in the mixing channel can be mostly done by diffusion. The following calculation illustrates considerations which can be used in designing of the mixing channel. The particular numbers used in this calculation are used only for illustration and are not limiting this invention.

The mixing channel should provide a uniform mixing and also a time delay due to the mixing channel should be much smaller than separation time. Due to a laminar flow typical for microfluidic devices, mixing in the mixing channel is mostly done by diffusion. To achieve a uniform mixing, $t_1$, the time for a molecule of a solvent to diffuse across the mixing channel, should be much smaller than $t_2$, the time for the mixture of solvents to flow through the mixing channel. $t_1$ can be estimated as $t_1=L_{diff}^2/D$, while $t_2$ can be estimated as $t_2=LWH/Q$, where L, W, and H are the length, width and height of the microchannel; Q is a volumetric flow rate of the mixture; D is the diffusion coefficient; and $L_{diff}$ is a distance that a molecule has to diffuse. $L_{diff}$ can be approximated as W, as the solvents of the mixture are provided in plane of the substrate. Taking this into account, the condition for uniform mixing can be rewritten as $L>>(QW)/(DH)$. For small molecules, D for small molecules in water is of the order $10^{-9}$ m$^2$/s. Based on the desired flow rates, the parameters of the mixing channel can be adjusted. For example, for a mixing channel with 20 μm×20 μm cross section and for a flow rate of 120 nL/min, the length of the channel should be at least 2 mm. For these parameters of the mixing channel, the swept volume is 0.8 nL and the time delay due to the mixing channel is 0.4 s, much smaller than separation times in the gradient elution chromatography.

FIG. 25B illustrates the importance of using a proper geometry in the design of the mixing channel. In FIG. 25B, a 5 micron high by 100 micron wide channel and 20 μm (width)×20 µm (height) channel were used as the mixing channel and a colored solution was used in one of the gradient pump chambers. FIG. 25B shows that the colored component is not distributed evenly across the width of the channel before mixing. After the mixer, the colored component is evenly distributed across the width of the channel which indicates that mixing is done well.

Figure 21A:
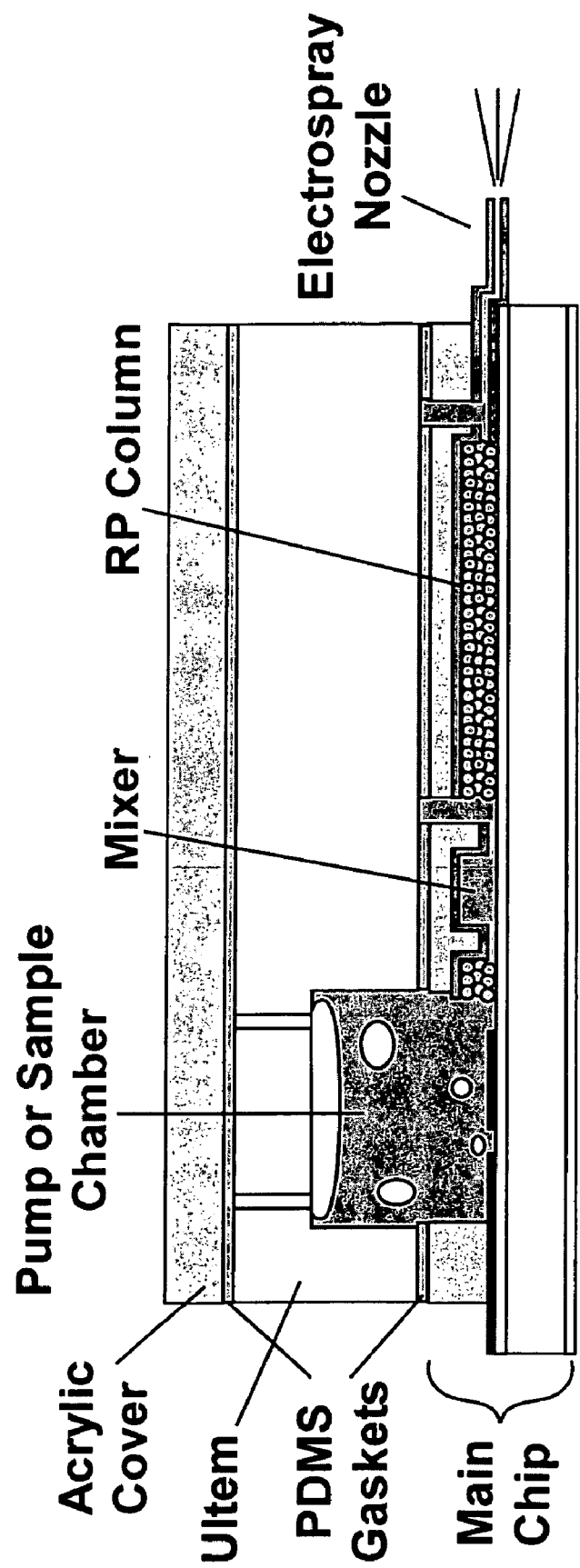
FIG. 21 illustrates chip packaging of a main chip and a reservoir chip as a single LC-ESI device.

In some embodiments, channels on the substrate connecting the gradient pump systems to the mixer can be packed with particles such as microparticles or nanoparticles as illustrated in FIG. 21A. These particles can be, for example, beads used to pack the chromatography column. Packing the channels between the gradient pump systems and the mixer with particles can buffer pressure fluctuations from the pump systems. Packing the channels between the gradient pump systems and the mixer with particles can be carried out, for example, using methods for packing chromatography columns disclosed in US patent application publication No. 2003-0228411 "A Method for Integrating Micro- and Nanoparticles Into MEMS and Apparatus Including the Same" by Tai et. al. published Dec. 11, 2003, and U.S. provisional patent application No. 60/663,181 "Wafer Scale Solid Phase Packing" filed Mar. 18, 2005, both incorporated hereby by reference in their entirety.

The microfluidic device can comprise a reservoir chip placed on the top of the main chip.

Figure 21:
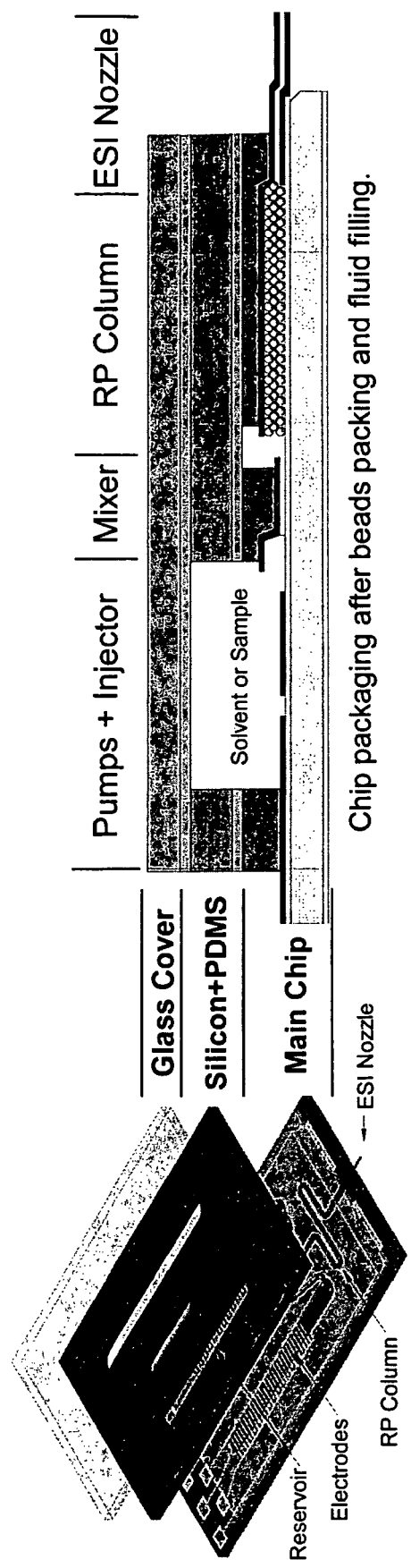

The reservoir chip can contain one or more reservoirs or cavities. The reservoir chip can be aligned with the substrate so that each reservoir can be placed over the chamber of one of the pump systems to increase the volume available for the fluid in the chamber, as illustrated, for example, in FIG. 21 (showing an Ultem reservoir chip). Larger volumes of the pump chambers can be necessary in order for pumps to perform functions other than gradient elution such as rinsing. The reservoir chip can include, for example, reservoirs for aqueous and organic solvents used for the gradient elution. The reservoir chip can also include, reservoir for a sample to be analyzed. The volume of each of the solvent reservoirs can be, for example, at least about 5 microliters, more preferably at least about 10 microliters. The volume of the sample reservoir, can be at least about 2 microliters, more preferably at least about 4 microliters. The reservoir chip can comprise silicon, glass, or polymer material such as a polyetherimide (ULTEM, GE Plastics). The microfluidic system can further comprise a sealing element, or a first sealing element, disposed or placed between the front surface of the substrate and the back surface of the reservoir chip. This sealing element can be a gasket comprising a polymer material such as an elastomer, including for example a polysiloxane such as for example polydimethylsiloxane (PDMS). The polymer material comprises silicone rubber, perfluoroelastomer, polytetrafluoroethylene, or parylene. Before its use as the sealing element, PDMS or other polymer material used in the sealing element can be presoaked in an organic solvent to remove impurities that could contribute to background noise. The organic solvent for this presoaking can be, for example, ethanol, methanol, propanol, or a combination thereof. Preferably, the gasket can have a shape of the reservoir piece, or at least substantially so. In some embodiments, the main chip, i.e. the substrate with the chromatography column, the ESI nozzle and the pump systems, can be planarized to improve adhesion with the sealing element. Planarizing of the main chip can be carried out, for example, by depositing a layer of epoxy-based photoresist, such as a photoresist of SU-8 series.

In some embodiments, a second sealing element, such as PDMS gasket, can be placed on the front surface of the reservoir chip. The second sealing element can be used, for example, to provide a seal between a cover, including a top cover, and the reservoir chip. The top cover can comprise a transparent material, such as acrylic.

A microfluidic device using a main chip, two gasket layers, an ULTEM reservoir chip, and cover is illustrated in FIG. 21A. A microfluidic device using silicon reservoir chip is illustrated in FIG. 21B.

In some embodiments of the microfluidic device, the electrodes in each of the pump systems can have an interdigitated configuration. The following calculation illustrates advantages of this particular configuration. The particular numbers used in this calculation are used only for illustration and are not limiting this invention.

The interdigitated electrode configuration can one allow to reduce the bulk resistance, $R_{cell}$, thereby reducing voltages necessary for electrolysis. Decreasing the bulk resistance can also allow one to reduce joule heating of the fluid in the pump chamber, which decreases pumping efficiency. $R_{cell}$, the resistance of the bulk electrolyte in the cell, can be estimated as $R_{cell}=\rho\kappa$, where $\rho$ is the specific resistivity of the electrolyte and $\kappa$ is the cell constant. In some embodiments, the interdigitated electrodes can have equal spacing s and equal width w and the number of electrodes can be much greater that 1. In this case, the cell constant can be estimated as $\kappa=2(s+w)/w_c l_c$, where $l_c$ is the total length of the interdigitated electrodes, and $w_c$ is the length of the individual electrode. Using values s=w=50 µm, $l_c$=5 mm and $w_c$=1 mm, s can be estimated to be 0.4 cm$^{-1}$.

In HPLC, the mobile phase can usually comprise water, organic solvent and an electrolyte such as formic acid, trifluoroacetic acid or acetic acid. For the same concentration of electrolyte, the specific resistivity is usually higher for a mixed aqueous/organic solution than for aqueous solution. For example, the specific resistivity of water/acetonitrile/formic acid (50:50:0.1 by volume) solution, commonly used in RP-HPLC, is about 8 kΩ·cm. Accordingly, $R_{cell}$=3.2 kΩ and $IR_{cell}$=3.2 V for 1 mA current. These current and voltage values can be easily handled by common IC circuit with a power supply lees than 15 V.

For the gradient elution, one can increase a pumping rate of one of the solvents, while decreasing a pumping rate of the other. One way to achieve decreasing of the pumping rate can be placing the interdigitated electrodes with spacing close to the thickness of the Nernst diffusion layer which is typically of the order of 0.1 mm. This sort of placing can greatly enhance mass transport leading to the reduction of the concentration potential. This placing can also enhance the recombination since $H_2$ and $O_2$ are not separated. The enhanced recombination can speed up the pressure release from the pump chamber which is otherwise limited to gas permeation and the pumping of the fluid itself.

The chromatography column can be similar to a chromatography column disclosed in US patent application publication No. 2005-0051489 "IC-processed Polymer Nano-liquid Chromatography System" by Tai et. al. published Mar. 10, 2005, incorporated hereby by reference in its entirety. The chromatography column can comprise polymer material such as parylene or polyimide.

The ESI nozzle can be similar to the ESI nozzle disclosed in the U.S. patent application Ser. No. 09/442,843 "Polymer Based Electrospray Nozzle for Mass Spectrometry" by Tai et. al. filed Nov. 18, 1999, incorporated hereby by reference in its entirety. The ESI nozzle can comprise two polymer layers. The polymer layers can be, for example, parylene layers. The ESI nozzle can comprise a channel between the inlet and the outlet. An electrode can be located inside the channel of the ESI nozzle. The electrode can comprise, for example, Ti, Pt, Au, Pd, Cr, Cu, Ag, carbon, graphite, pyrolyzed carbon or a combination thereof. The electrode can be used to provide a contact for electrospray ionization. Preferably, the ESI nozzle can be an overhanging ESI nozzle, such as a nozzle that extends beyond the edge of the substrate. The length on which the overhanging nozzle extends beyond the edge of the substrate can vary from a few microns to several millimeters (e.g., one micron to 3 mm; or two microns to 2 mm, or 3 microns to 1 mm). The overhanging length can be adjusted to make the ESI nozzle compatible with a particular mass spectrometer.

In some embodiments of the invention, the microfluidic device can further comprise one or more sensors. For example, one or more thermal flow sensors can be microfabricated inside the mixing channel to measure a flow rate of the mixture of solvents used for gradient elution. The thermal flow sensors can be similar, for example, to thermal flow sensors disclosed in US patent application publication No. 2004-0188648 "INTEGRATED SURFACE-MACHINED MICRO FLOW CONTROLLER METHOD AND APPARATUS" to Xie et. al. published Sep. 30, 2004, incorporated hereby reference in its entirety. In some embodiments, the microfluidic system can comprise one or more pressure sensors. The pressure sensors can be placed, for example, inside the pump systems, including the gradient pump systems and the sample injecting pump systems, or any other suitable location to provide in-situ pressure measurement. The pressure sensors can be similar to pressure sensors disclosed in US patent application publication No. 2004-0237657 "Integrated Capacitive Microfluidic Sensors Method and Apparatus" by Tai et. al. published Dec. 2, 2004, incorporated hereby by reference in its entirety. In some embodiments, the microfluidic system can comprise one or more capacitive sensors integrated inside the mixing channel to measure a composition of the mixture of solvents used for gradient elution. These capacitive sensors can be similar to those in US patent application publication No. 2004-0237657 ("Integrated Capacitive Microfluidic Sensors Method and Apparatus" by Tai et. al. published Dec. 2, 2004, incorporated hereby by reference in its entirety. In some embodiments, the microfluidic system can include one or more sensors for measuring a conductivity of fluid, each comprising a plurality of interdigitated electrodes. These sensors can integrated inside the mixing channel and measure a conductivity of the mixture of solvents for gradient elution. These sensors can be also integrated inside the chromatography column. The sensors for measuring a fluid conductivity comprising interdigitated electrodes can be similar to sensors disclosed in US patent application publication No. 2005-0051489 "IC-processed Polymer Nano-liquid Chromatography System" by Tai et. al. published Mar. 10, 2005, incorporated hereby by reference in its entirety.

Fabrication and Packaging

One embodiment of the present invention is a method of making of a microfluidic device with on-chip pumping, said method comprising microfabricating a main chip, said main chip has a front surface and the back surface and comprising one or more pump systems on the front surface, each of the pump systems comprises a chamber providing a volume for storing a fluid; and microfabricating a reservoir chip, said reservoir chip has a front surface and a back surface and one or more cavities on the back surface; aligning the reservoir chip on the top of the main chip so that the front surface of the main chip faces the back surface of the reservoir chip and so that at least one of the cavities extends the volume for storing a fluid in one of the pumps.

Microfabrication is known in the art and can comprise combinations of steps including deposition, coating, etching, roughening, and patterning. For example, microfabricating is illustrated on FIG. 20 of the main chip can comprise one or more of the following process steps:

providing a substrate having a front surface and a back surface;

thermally growing oxide on the front surface of the substrate;

depositing a thin conducting layer on the front surface of the substrate using, for example, E-beam or thermal evaporation;

patterning the thin conducting layer to form a plurality of electrode using, for example, wet etching;

patterning the oxide on the front surface using, for example, wet etching such as HF etching;

applying an adhesion promoter on the substrate;

depositing a first layer of polymer such as parylene;

depositing a layer of sacrificial photoresist to define fluid channels on the substrate by, for example, spinning;

patterning the layer of sacrificial photoresist to define, for example, channels of the mixer and nozzle regions;

depositing a second layer of polymer such as parylene;

roughening the exposed surface, e.g. silicon surface, by dry etching such as $XeF_2$ etching;

sputtering or thermally evaporating a mask for etching the second layer of polymer in order to define the shape of the nozzle;

removing the mask by wet etching;

cleaning the substrate in, for example, HF solution or oxygen plasma cleaner;

planarizing the substrate by spin coating SU-8 layer;

etching the substrate with, for example, $XeF_2$ etching to make the nozzle freestanding and overhanging.

The openings of the channels, including the channel of the nozzle, must be sufficient large so that sacrificial material can fully escape so that plugging does not occur.

Microfabricating the reservoir chip can be carried out by, for example, etching including for example deep reactive ion etching of a substrate such as silicon wafer or a glass.

The method of making a microfluidic device with on-chip pumping can further comprise placing a sealing element between the reservoir chip and the main chip. This can be called a first sealing element.

The method of making a microfluidic device with on-chip pumping can further comprise placing a second sealing element on the front surface of the reservoir chip.

The sealing elements can be, for example, gasket layers made of polymer or elastomer such as for example silicone rubber, polysiloxane such as for example polydimethylsiloxane.

The volumes for storing a fluid can be filled with a fluid using a syringe.

The method of making a microfluidic device with on-chip pumping can further comprise clamping the main chip and the reservoir chip to ensure that the fluid storing volumes are tightly sealed. A cover can be used to ensure a tight seal.

The assembled device can be inserted into a testing jig for use with a mass spectrometer.

The microfluidic device can be used for separation of low molecular weight or high molecular weight molecules, self-assembled structures, and particles including biomolecules, including proteins, peptides, nucleic acids, and lipids. Another embodiment provides a method of biomolecular separation comprising the step of chromatographically separating a mixture of biomolecules using a microfluidic system for liquid chromatography/electrospray ionization mass spectrometry comprising:

(A) a main chip comprising: a substrate having a front face and a back face; a chromatography column on the front face of said substrate, wherein said column has an inlet and an outlet and a chromatographic medium; an electrospray ionization (ESI) nozzle on the front face of said substrate, wherein said nozzle has an inlet and an outlet, and wherein the inlet of the nozzle is microfluidically coupled to the outlet of the column; one or more pump systems on the front face of said substrate comprising a pump chamber, one or more electrodes, and an outlet microfluidically coupled to the inlet of said column;

(B) a reservoir chip comprising a front surface and a back surface, wherein the reservoir chip has one or more cavities in the back surface which when disposed next to the front surface of the main chip extends the volume of the pump chamber of one of the pump system.

The biomolecules can be proteins, peptides, nucleic acids, DNA, RNA, viruses, lipids, and other biomolecules known in the art which can be chromatographically separated. Mass spectral analysis of the separated biomolecules can be carried out using the ESI method.

The various embodiments are further illustrated with use of the following additional, non-limiting working examples and description thereof.

LC-ESI Chip

Figure 19:
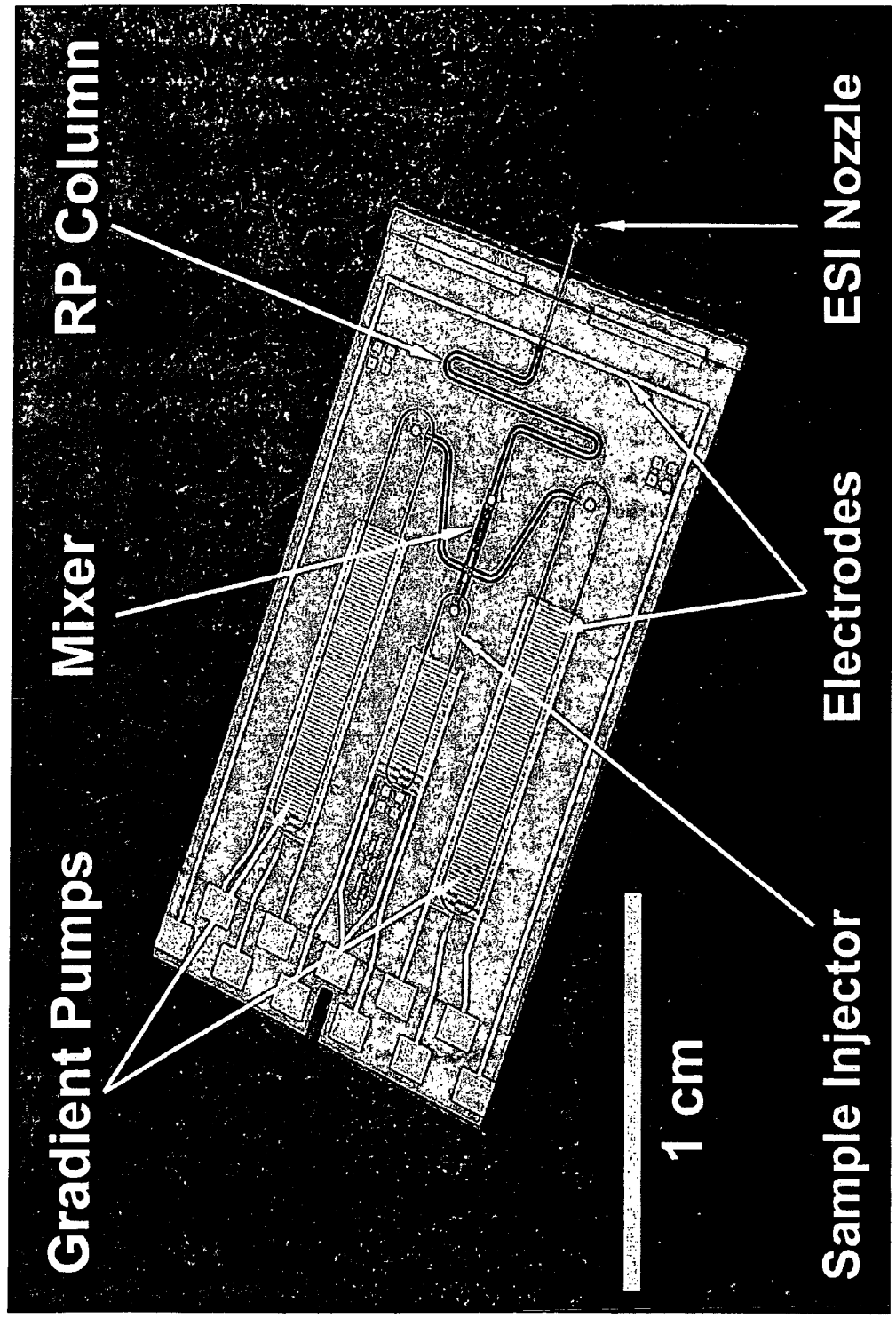
FIG. 19 shows a photograph of a fabricated microfluidic system for liquid chromatography/electrospray ionization integrating important components on a main chip.

FIGS. 1 and 19 show an LC-ESI chip. Important components of a LC-ESI system are integrated into chip format. These components include for example: solvent gradient pumps, a passive mixer, a sample injector, a reversed-phase (RP) column and an ESI nozzle. Except for solvent and sample reservoirs, all these components are integrated onto a single silicon chip.

Gradient Pump and Sample Injector

Gradient elution, mixture of aqueous (polar) and organic (non-polar) solvents, is usually used in reversed-phase chromatography. In most cases, elution starts at high aqueous concentration and gradually changes to high organic concentration.

A typical nano-LC binary solvent gradient has a total flow rate of 100 nL/min and a duration of 10 s minutes to several hours. A typical sample injection also uses a sample volume around 1 µL. Besides the gradient elution, the pumps must be able to perform other functions, such as rinsing. To realize all these functions, a total solvent volume larger than 10 µL can be used. This volume amount prevents the solvent and sample reservoirs to be integrated into a single silicon chip. To accommodate such a volume, the reservoirs are mainly built into a separate reservoir chip (500 µm thick silicon). On each side of the reservoir chip, a 300 µm PDMS is used as gasket. The area of each reservoir on the chip surface will be 1 mm wide and 10 mm long. After packaging, the height of the reservoirs is expected to be 1 mm. Thus, it is possible to build two 10 µL solvent reservoirs and one 3.5 µL sample injector on a 1 cm×2 cm chip and still leave room for other components. Details of the fabrication are presented later in the fabrication section.

For the electrodes design, an interdigitated configuration was chosen. The main reason for this is to reduce the bulk resistance, $R_{cell}$, thereby also reducing the voltages necessary for electrolysis. Decreasing the bulk resistance also reduces undesired joule heating of the fluid, which decreases pumping efficiency. $R_{cell}$, the resistance of the bulk electrolyte in the cell, is given by $R_{cell}=\rho\kappa$, where $\rho$ is the specific resistivity of the electrolyte and $\kappa$ is the cell constant. For interdigitated electrodes that have equal finger space s and finger width w and the number of the fingers>>1, the cell constant $\kappa$ is given by $\kappa=2(s+w)/w_c l_c$ where $l_c$ is the total length of the interdigitated electrodes, $w_c$ is the length of each finger. Here, s and w are 50 µm. If $l_c$ is 5 mm and $w_c$ is 1 mm, then $\kappa$ becomes 0.4 $cm^{-1}$.

Usually, in HPLC, the mobile phase can comprise water, an organic solvent, and an electrolyte such as formic acid. The specific resistivity of a mixed aqueous/organic solution is higher than that of aqueous solution for the same electrolyte concentration. The $\rho$ value for water/acetonitrile/formic acid (50:50:0.1 by volume) solution, like those commonly used in RP-HPLC, is about 8 kΩ·cm. Then the estimated Rcell is 3.2 kΩ and IRcell is 3.2 V for 1 mA current. These values can be easily handled by common IC circuit with a power supply less than 15 V.

On the other hand, typical thickness of the Nernst diffusion layer is on the order of 0.1 mm. With the space between the cathode and anode approximating that thickness, mass transport is greatly enhanced which leads to the reduction of the concentration overpotential $\eta_c$. Although this will also enhance the recombination since $H_2$ and $O_2$ gases are not separated, it can be beneficial. A binary solvent gradient requires one of the solvents pumping rate to decrease while the other increases. Besides the gas permeation and the liquid pumping itself, there is no other way to bleed the pressure inside the pumping chamber. The enhanced recombination can speed up the pressure releasing while compromising the electrolysis efficiency.

Passive Mixer

Solvents in the gradient elution should be well mixed together before entering the separation column to avoid causing any negative effect on the chromatography. Due the laminar flow in the microfluidic devices, mixing is mostly done by diffusion. The passive mixer here can be basically a mixing channel. To enhance mixing, the diffusion length can be reduced. A channel with a 20 µm×20 µm cross section is used as passive mixer. Diffusion constant D of small molecules in water is on the order of $10^{-9}$ $m^2$/s. Time needed for mixing $t_{mix}$ is approximately $t_{mix}=L^2_{diff}/D$, where $L_{diff}$ is the diffusion length which is 20 µm. $t_{mix}$ is estimated to be around 0.4 s. For a flow rate of 100 nL/min, the flow velocity in the mixing channel is about 5 mm/s. Then the length of the mixing channel should be at least 2 mm. The sweep volume of the mixer is 0.8 nL.

Reversed-Phase Column

Solid phase in the reversed-phase separation column is C18-coated 5 µm fused silica beads with a pore size of 30 mm. The beads were purchased from Vydac. Commercial nano-LC capillary column is available in diameters<100 µm with an optimal flow velocity around 1 mm/s. In the chip, column is chosen to have a cross section of 20 µm (H)×100 µm (W) whose area is equivalent to a 50 µm I.D. capillary. Then the optimal flow rate for separation is around 100 nL/min. As proof of concept, the column length is reduced to 10 mm compared to the typical 50 to 250 mm. Thus, the separation can be performed under relatively low pressure which is around 3 bar.

ESI Nozzle

The ESI nozzle is very similar to the one that was previous demonstrated by our group. Overhanging distance of the nozzle is about 1 mm. The tip orifice is about 5 µm high and 20 µm wide, and the curvature of the very end is about 1-2 µm. The channels that connect both pumping chambers and the nozzle are 5 µm high and 100 µm wide. Structural materials for the ESI nozzle are two parylene layers. An integrated platinum electrode is located in the nozzle channel to provide electrical contact for electrospray.

Fabrication

Chip Design and Packaging

The schematic diagram of the chip design and packaging is shown in FIG. 21B. There are three main components. First, an ESI nozzle, a column, a mixer, a sample injector, and gradient pumps (electrodes) are integrated onto a main chip which is a silicon substrate. On top of the main chip is a solvent and sample reservoir chip which is a silicon substrate bonded with PDMS gaskets. On the main chip, top surface is planarized using a thick 50 μm SU-8 layer which creates a flat surface for the reservoir chip to sit on. To use the chip, the reservoir chip is placed on the SU-8 planarized main chip. The adhesion between the PDMS and the SU-8 or silicon is adequate for filling the chambers with solvent using a syringe. Once the solvent chambers are filled, the two chips are clamped down using the glass cover to ensure the solvent and sample reservoirs are sealed. Clamping force and electrical connection to the chip are provided by a custom made jig.

Fabrication Process

Figure 20:
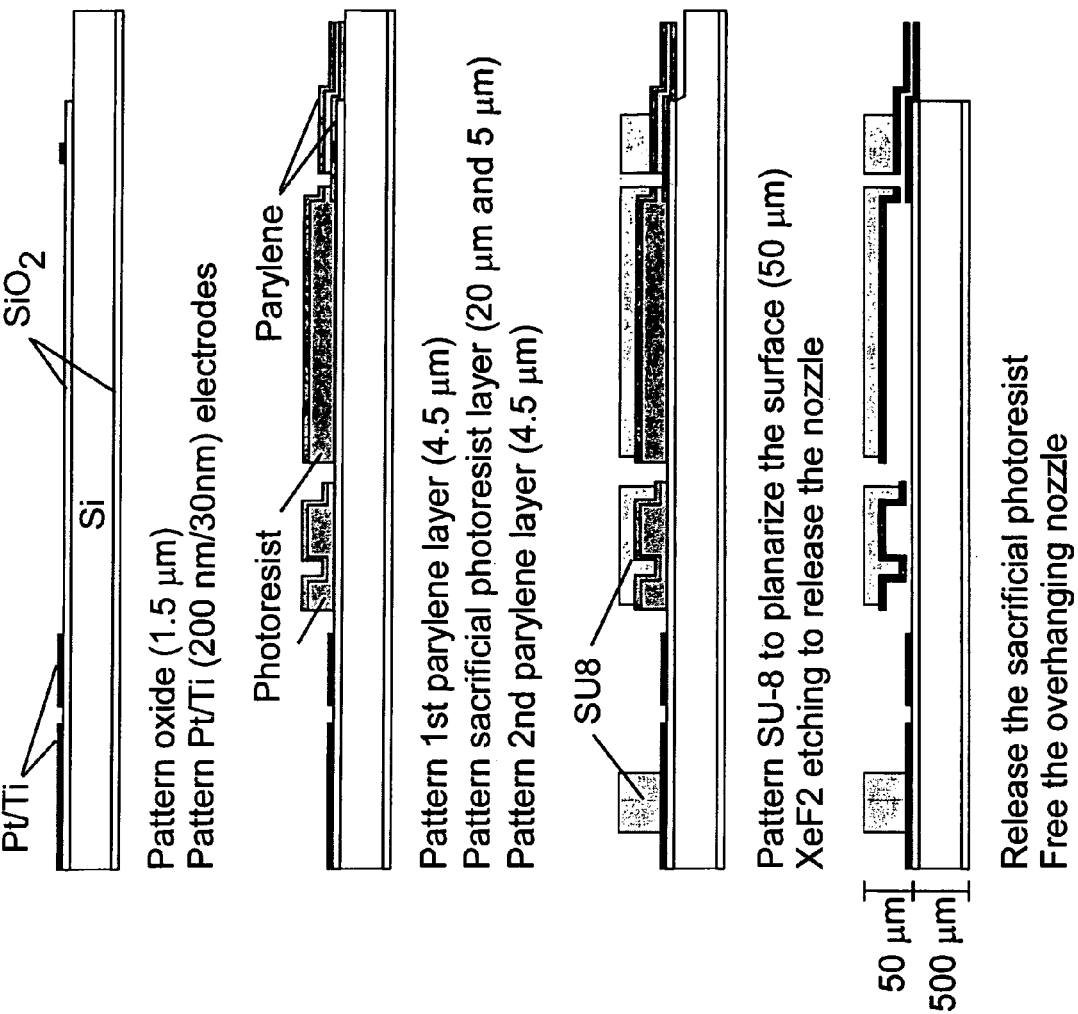
FIG. 20 shows a fabrication process flow for the main chip of the microfluidic system for liquid chromatography/electrospray ionization.

The detail fabrication process is shown in FIG. 20. The process began with a 4-inch silicon wafer with 1.5 μm of thermally grown oxide. Electrolysis electrodes were made of E-beam evaporated platinum/titanium (200 nm/30 nm). Heated (~80° C.) Aqua Regia (HNO3:HCl=1:6) was used for Pt/Ti etching. After patterning the electrodes, the front side oxide was patterned using buffered HF. Before first parylene deposition (4.5 μm), adhesion promoter (A-174 from Specialty Coating Systems) was applied to the substrate. Then 20 μm sacrificial photoresist was spun on the wafer to define fluid channels. A partial exposure was performed to reduce the height of the channels in the mixer and nozzle regions. These regions also serve as filter structures to prevent beads flowing through. Second parylene layer (4.5 μm) was deposited and pattern to form channel ceiling. In order to promote adhesion between the silicon substrate and the second parylene layer, short XeF2 dry etching was performed to roughen the exposed silicon surface. A 150 nm sputtered aluminum layer was used as a mask for parylene etching to define the shape of the nozzle. The Al was later removed by wet etching. Wafers then went through a 5% HF dip and oxygen plasma cleaning before a 50 μm SU-8 layer was spin-coated on. The SU-8 layer was patterned and served to provide a flat overall chip surface to support the reservoir chip. After SU-8 developing, wafers were left inside the SU-8 developer (propylene glycol monoether acetate, PGMEA) to release the photoresist. After the photoresist had been dissolved, an 80 μm deep anisotropic XeF2 etching was used to undercut the nozzle and make it freestanding. Wafers were then diced into 1×2 cm chips. A photomicrograph of the fabricated device is shown in FIG. 19. The reservoir chip was fabricated by using DRIE to etch through a 500 μm thick silicon wafer. 300 μm PDMS gaskets were formed by spinning it on a silicon wafer, and then peeling them off after curing. The PDMS gaskets were bonded to both sides of the reservoir chip. The bottom PDMS gasket was cut to the shape of the reservoir chip. Au, Ti and Al metals were purchased from Williams Advanced Materials (Brewster, N.Y.). Au and Al etchants and buffered HF were purchased from Transene Inc. (Danvers, Mass.). All photoresist materials were purchased from Clariant (Somerville, N.J.). SU-8 was manufactured by Microchem (Newton, Mass.). Parylene was provided by Uniglobe Kisco (San Jose, Calif.). XeF2 was purchased from Pelchem (Pretoria, South Africa). PDMS was Sylgard® 184 from Dow Corning (Midland, Mich.).

Experimental Results

Testing Setup

Solvents and samples are pre-injected into the reservoirs before testing. Filling/venting ports located at either end of the solvent and sample reservoirs were punched through the PDMS gasket. Stainless steel syringe needles from Hamilton Co. (Reno, Nev.) were inserted through the holes in the PDMS layer and fluid was injected into the reservoirs. The gas venting holes at the opposite end of the reservoirs ensured complete filling. After filling, a glass cover was placed and clamped on top of the reservoir chip to seal the reservoirs. Elastomeric connector from ARC-USA (Grand Prairie, Tex.) was used to provide robust electrical connection to chip. This method is more convenient than wire bonding since bonding wire can be damaged easily during handling of the chips, while at the same time, requires much less space than probes. Limitations of elastomeric connector are higher contact resistance and low current capacity (~1 mA/m$^2$). However, for the most experiments, it is sufficient.

Figure 22:
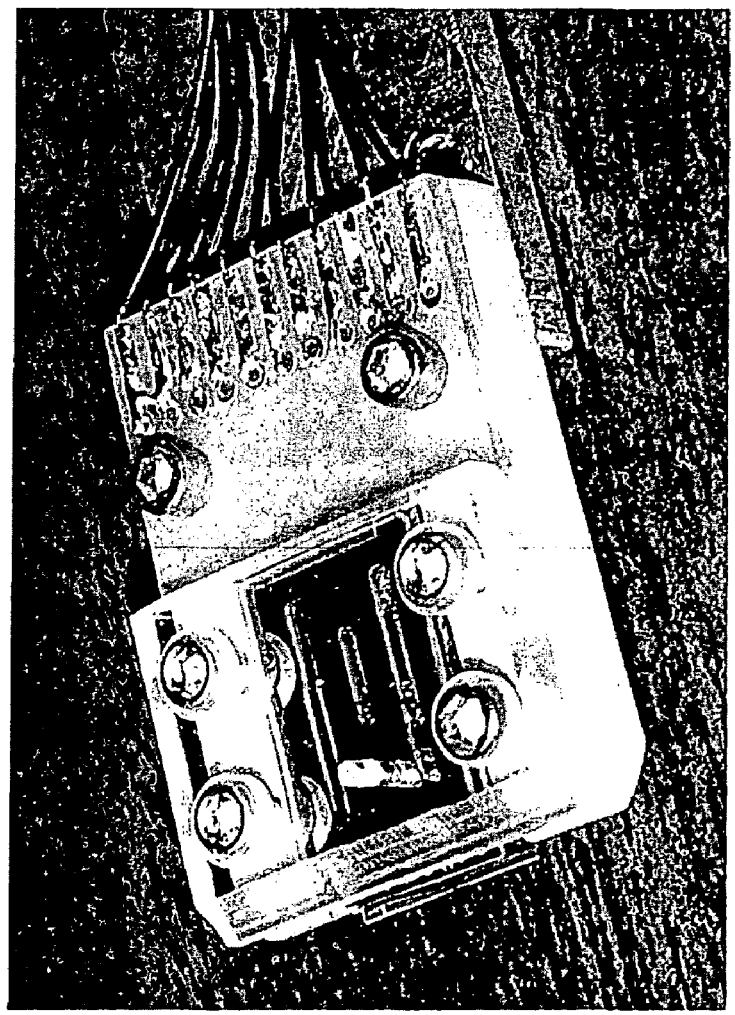
FIG. 22 shows a photograph of the packaged chip.

The three chips were manually aligned and placed in a custom-made jig shown in FIG. 22. Orthogonal electrospray configuration used in Agilent Ion Trap MSD, shown in FIG. 23 was adopted. The ESI assembly come with the MSD, shown in FIG. 24, was modified to accommodate the testing jig. Electrolysis pumps were galvanostatically controlled using output currents from custom-built voltage to current converters. Full-scale current range was normally 1 mA and it was adjustable. The voltages were programmed in LabView and were fed to the converters through a DAQPad-6020E interface board from National Instruments (Austin, Tex.).

Commercial LC-MS System

Figure 27:
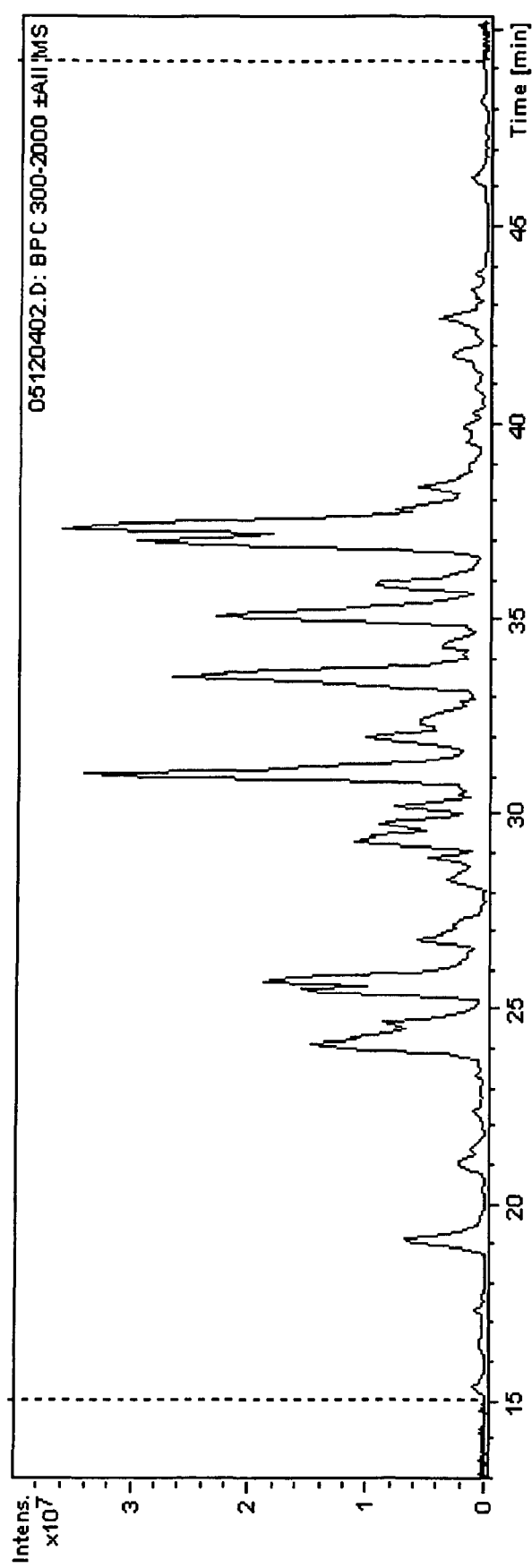
FIG. 27 presents typical peptide separation done by Agilent 1100 LC-MS system.

As a comparison for the chip performance, a typical peptide separation was performed using a commercial system. Sample was 1 pmol/μL peptide mixture from tryptic digested bovine serum albumin (BSA). Gradient elution was provided by Agilent 1100 LC pumps. Column used was a 75 μm I.D. and 15 cm long capillary. Packing material in the RP column was 3.5 μm Agilent Zorbax 300 SB-C18 beads. Aqueous solvent was (water/acetonitrile/formic acid, 95/5/0.1 by volume) and organic solvent was (water/acetonitrile/formic acid, 40/60/0.1 by volume). During the separation, a 500 nL sample (500 fmol) was injected and flow rate was set to be 100 nL/min with gradient change from 100% aqueous to 100% organic. Total separation took 55 min and the result is shown in FIG. 27.

Chip Performance

Figure 28:
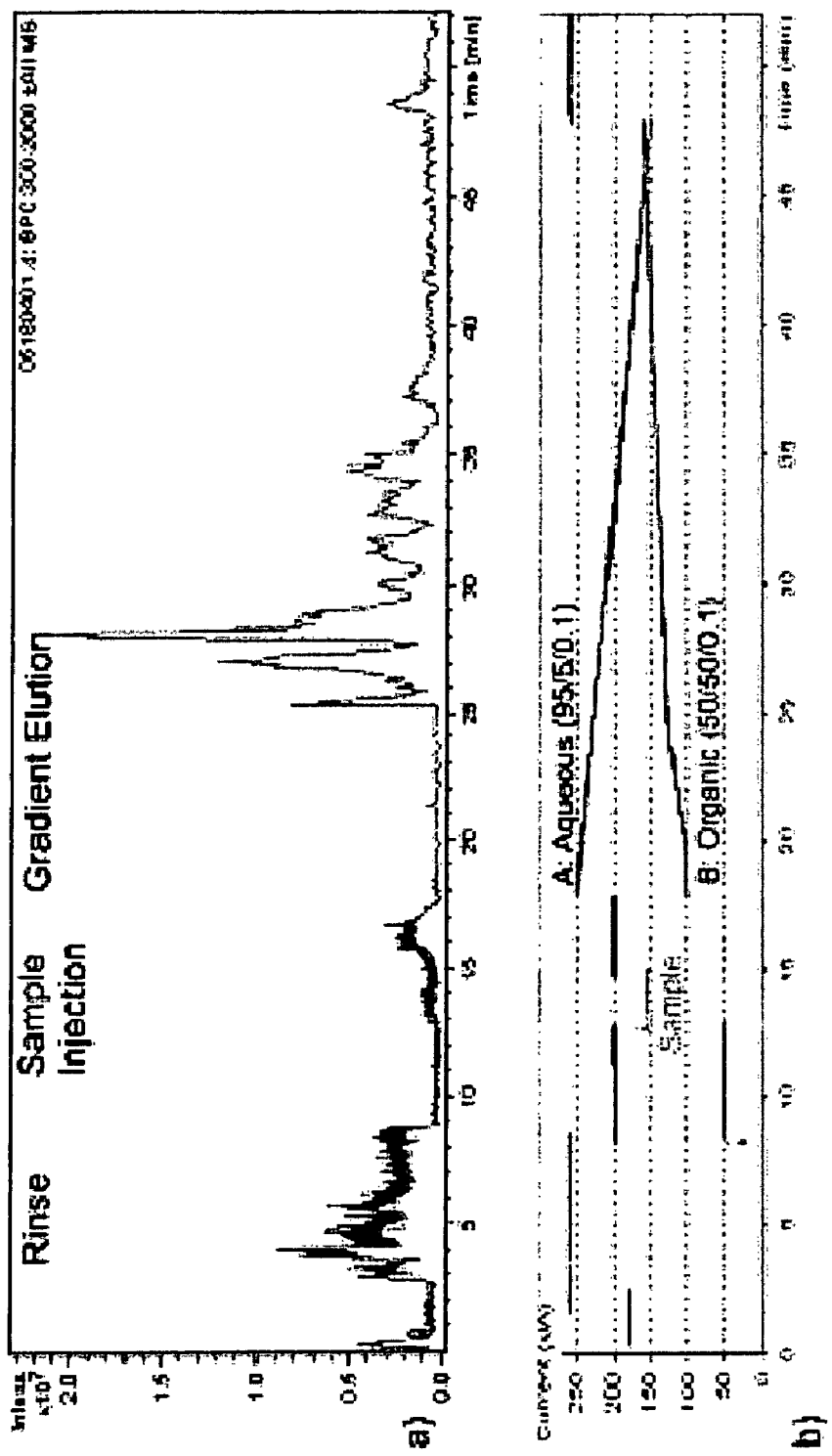
FIG. 28 presents a peptide separation done by the microfluidic system for on-chip LC-ESI. (a) is a chromatogram; (b) is a control current profile.

Similar separation was performed using the LC-ESI chip. The sample used here is the same as in the capillary case. Packing material used was 5 μm Vydac C18 beads. The 1 cm on-chip column has a cross section equivalent to a 50 μm I.D. capillary. The aqueous solvent was (water/acetonitrile/formic acid, 95/5/0.1 by volume) and organic solvent was (water/acetonitrile/formic acid, 50/50/0.1 by volume). The result is shown in FIG. 28. First, the organic solvent pump was turned on to rinse the column. Then the aqueous solvent was pumped through to regenerate the column. The injected sample volume was 500 nL (about 500 fmol sample). The gradient changed from 100% A to 100% B and lasted about 30 min with an estimated flow rate of 100 nL/min. The control current profile that was applied to the electrolysis pumps was also given in FIG. 28(b).

Comparison

Figure 29:
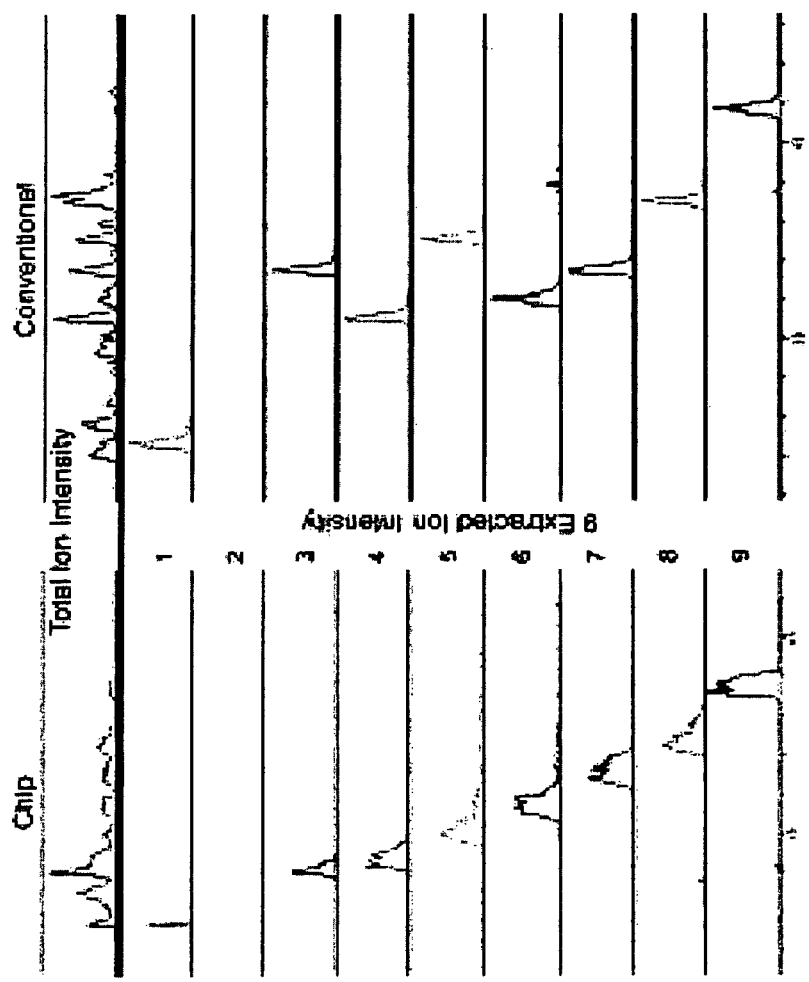
FIG. 29 illustrates separation comparison between the commercial system and the on-chip LC-ESI microfluidic system.
Figure 30:
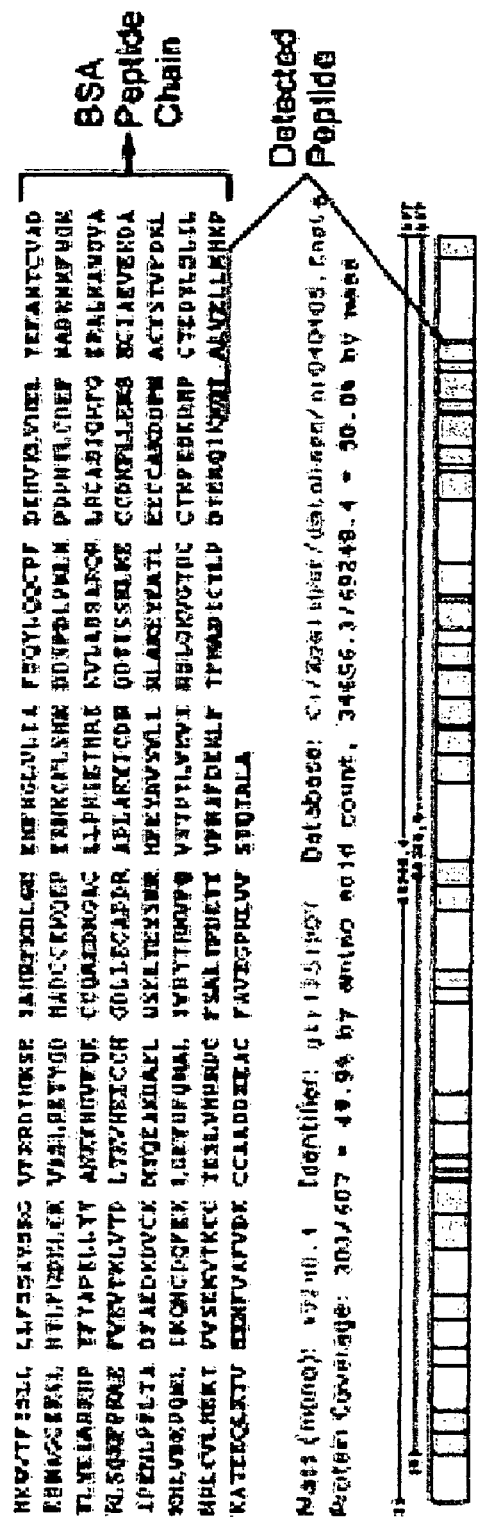
FIG. 30 shows peptide coverage from the database search in the separation done by the on-chip LC-ESI microfluidic system.

FIG. 29 compares the separation done by the commercial system and the chip. In FIG. 29, 9 ions are extracted and listed for both experiments. Except for ion No. 3 and 5, the elution orders and times are very similar for both cases. The difference in ion No. 3 and 5 could caused by the relatively high temperature of the chip due to its close placement to the heated MS inlet. Based on the MS data, a database search was carried out to identify peptides associated with those ion signals. The result for the chip is listed in FIG. 30. The peptide coverage of the experiments done by the chip was 50% which is comparable to the 60% achieved by the Agilent 1100 LC-MS system.

Other Chip Testing

Other types of experiments were tested on the chip. For example, multiple separations with re-filling the reservoirs were demonstrated. Other types of organic solvents, such as methanol, were also tested. Usually, the chip can be reused several times by rinsing it carefully after experiments.

Integrated Sensors for Feedback Control or Detection

In order to achieve precise control of fluid transport inside the LC-ESI chip, various sensors can be integrated inside the chip to provide feedback signal. For example, thermal flow sensor can be fabricated inside the channel to provide flow rate measurement. The thermal flow sensor can be one described, for example, in Jun Xie, Jason Shih and Yu-Chong Tai, "Integrated Surface Micromachinned Mass Flow Controller", *The 16th IEEE International Conference on Micro-ElectroMechanical Systems* (MEMS 2003), Kyoto, Japan, January, 2003, pp. 20-23, incorporated hereby by reference in its entirety. Pressure sensor from can be put inside the pumps, injector or any suitable locations on the chip to provide in situ pressure measurement. Various capacitive sensors can be integrated inside the channel to measure the gradient composition, or use interdigitated electrodes to measure conductivity of fluid. The pressure sensors and capacitive sensors can be, for example, similar to those described in Jason Shih, Jun Xie, Yu-Chong Tai, "Surface Micromachined and Integrated Capacitive Sensors For Microfluidic Applications", *The 12th International Conference on Solid-State Sensors, Actuators and Microsystems* (Transducers 2003), Boston, USA, June, 2003, pp. 388-391, incorporated hereby by reference in its entirety.

Many detectors can also be integrated into the chip. For example, electrochemical sensors, conductivity sensors, photodetectors for UV or refractive index measurement, and the like.

Conclusions

A complete LC-ESI system was integrated in a chip format. Nano-LC reversed phase gradient elution was demonstrated using on-chip electrolysis pump. Separated analytes from on-chip column were then sprayed into MS for analysis through an integrated ESI-nozzle. Separation results are comparable to those of commercial system. Peptide identification performance using the LC-ESI chip with MS was also very close to those achieved by the commercial system.

Additional description is provided for a microfluidic platform for liquid chromatography-tandem mass spectrometry analyses including applications with complex peptide mixtures.

Experimental Section

Microfabrication. The chips were fabricated using developed Parylene surface micromachining technology, see e.g. Xie, J.; Miao, Y.; Shih, J.; He, Q.; Liu, J.; Tai, Y. C.; Lee, T. D. *Anal Chem* 2004, 76, 3756-3763; Xie, J.; Shih, J.; Lin, Q.; Yang, B.; Tai, Y. C. *Lab Chip* 2004, 4, 495-501; Licklider, L.; Wang, X.-Q.; Desai, A.; Tai, Y.-C.; Lee, T. D. *Anal. Chem.* 2000, 72, 367-375; Ho, C.-M.; Tai, Y.-C. *Annu. Rev. Fluid Mech.* 1998, 30, 579-612, which are all incorporated herein by reference in their entirety. In this process, alternating layers of Parylene and photoresist are deposited, with the photoresist ultimately being dissolved away, leaving only the desired Parylene structures.

The process used to fabricate the chip (FIG. 20) began with a 100 mm diameter silicon wafer with 1.5 μm of thermally grown oxide on the surface. Electrolysis electrodes were deposited by e-beam evaporation of platinum/titanium (Pt/Ti) (200 nm/30 nm). This metal deposition was done using the Integrated Micromachines Inc. (Monrovia, Calif.) foundry service. Heated (~80° C.) Aqua Regia ($HNO_3$:HCl=1:6) was used to pattern the Pt/Ti. After patterning the electrodes, the oxide was patterned using buffered HF. HF is an extremely toxic substance. Personnel working with HF must take adequate precautions to protect against exposure to either the liquid solution or vapors. This step is necessary to create anchors for the channels and also provide a way to make the electrospray nozzle freestanding at the end; both of which are done using $XeF_2$ (Pelchem, Pretoria, South Africa), a gas phase isotropic silicon etchant. After A-174 adhesion promoter (Specialty Coating Systems, Indianapolis, Ind.) was applied to the substrate, the first Parylene (Uniglobe Kisco Inc., San Jose, Calif.) layer (4.5 μm) was deposited and patterned by oxygen plasma, using photoresist as a mask. Then, a 20 μm sacrificial photoresist layer was spun on the wafer and patterned to define the fluid channels. For the mixer, nozzle and filter regions, a partial lithographic exposure was performed to reduce the height to 5 μm, producing a bi-level (20 μm/5 μm) photoresist sacrificial layer. Before deposition of the second Parylene layer, a short $XeF_2$ etch was performed to roughen the silicon surface exposed during the oxide patterning step. This roughened silicon served to promote adhesion between the Parylene and the substrate, allowing our structures to sustain higher pressures. $XeF_2$ is readily hydrolyzed to HF and must be handled using the same precautions. The second Parylene layer (4.5 μm) was then deposited and patterned by oxygen plasma using a 150 nm sputtered or thermally evaporated aluminum layer as a mask. This patterning step also defines the shape of the electrospray nozzle.

Wafers then went through a 5% HF dip and oxygen plasma cleaning before a 50 μm SU-8 (Microchem, Newton, Mass.) layer was spin-coated on. The SU-8 layer was patterned and served to provide a flat overall chip surface to facilitate packaging of the chip, which is needed to create the solvent resevoirs. The SU-8 also helped strengthen the channels for the necessary high pressure operation. After SU-8 developing, wafers were left inside the SU-8 developer (propylene glycol monoether acetate, PGMEA, Microchem) to dissolve the sacrificial photoresist. Finally, $XeF_2$ was used to etch away the exposed silicon underneath the nozzle and make it freestanding. Wafers were then diced into 1 cm×2 cm chips (FIG. 19).

The Al was obtained from Williams Advanced Materials (Brewter, N.Y.). Al etchant and buffered HF were purchased from Transene Inc. (Danvers, Mass.). Acids used to etch the Pt were obtained from VWR Scientific Products (West Chester, Pa.). And all photoresist materials were purchased from AZ Electronic Materials (Sommerville, N.J.).

Column Packing and Device Assembly. The column on each chip is individually packed with Polaris 3 μm C18-A silica based support (Varian, Palo Alto, Calif.). To do this, the chip was mounted into a Polyetherimide (Ultemg) jig (not shown) that coupled a port at the front of the column to Teflon tubing via a poly(dimethylsiloxane) (PDMS) gasket. A slurry of the beaded support in 2-propanol was forced into the column from a pressurized (250 psi) reservoir until the entire length of the column was filled. The side channels between the pump chambers and the mixer were similarly packed with the same 3 μm beaded support. Once packed, the chip was mounted in a different holder that utilized a 5 mm thick Ultem cover (FIG. 21A). Chambers, which matched up with the pumps on the chip, were machined into this cover piece to form reservoirs for the sample and solvent. A PDMS gasket provided the seal between the Ultem cover and the chip. Overall, each of the solvent chambers were 20 μL in volume and the sample chamber volume was 5 μL. These chambers could be filled using a syringe via two access ports at either end of each chamber. For our experiments, the solvent A reservoir was filled with a 95/5/0.1 (water/methanol/formic acid) solution while the solvent B chamber was filled with a solution of the same components in a ratio of 40/60/0.1. The sample chamber was filled with a 1 pmol/μL solution of Trypsin digested BSA. The access ports were later sealed using an acrylic cover piece and another PDMS gasket. Electrical contacts to the chip electrodes was accomplished using a printed circuit board clamped to the metal pads on the chips with a conductive elastomeric connector (Fujipoly, Carteret, N.J.) in between.

Mass Spectrometry. All MS analyses were performed using an Agilent MSD ion trap mass spectrometer. For the on-line capillary LC separations used for comparison, an Agilent 1100 series nanoflow LC equipped with a 75 μm ID 15 cm long column packed with 3 μm Zorbax 300SB-C 18 reverse phase support was used. Samples were first loaded from the autosampler onto a 500 μm ID 5 mm long trap column packed with 5 μm Zorbax 300SB-C 18 support at a flow rate of 100 μL/min using solvent A (0.1% formic acid in water). The trap column was then switched on-line and the peptides eluted with a 60 min gradient of 5 to 55% solvent B (0.1% formic acid in acetonitrile) at a flow rate of 300 nL/min. Both full range mass spectra and MS/MS spectra were collected in an automated fashion using programs built into the Agilent data system software.

Figure 23:
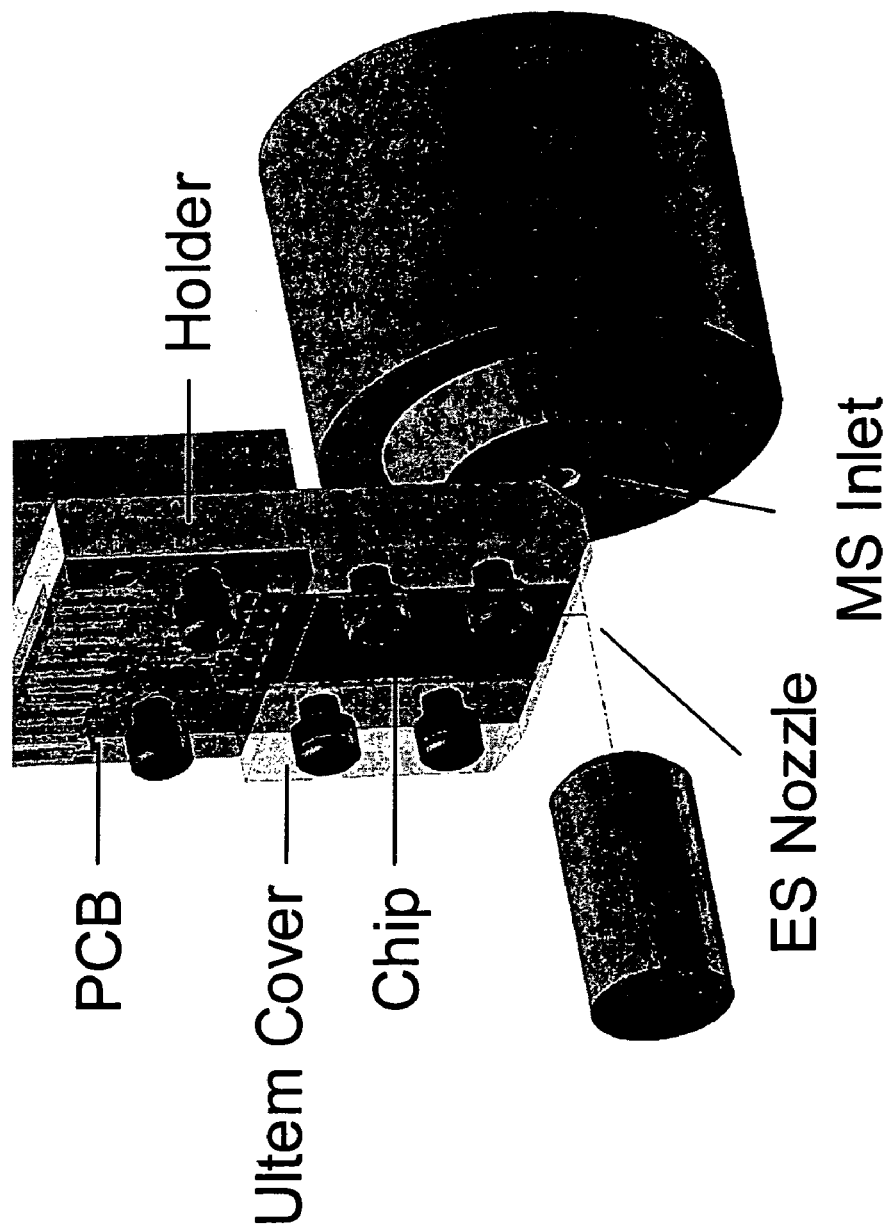
FIG. 23 illustrates positioning of the microfluidic device orthogonal to MS inlet for testing.
Figure 24:
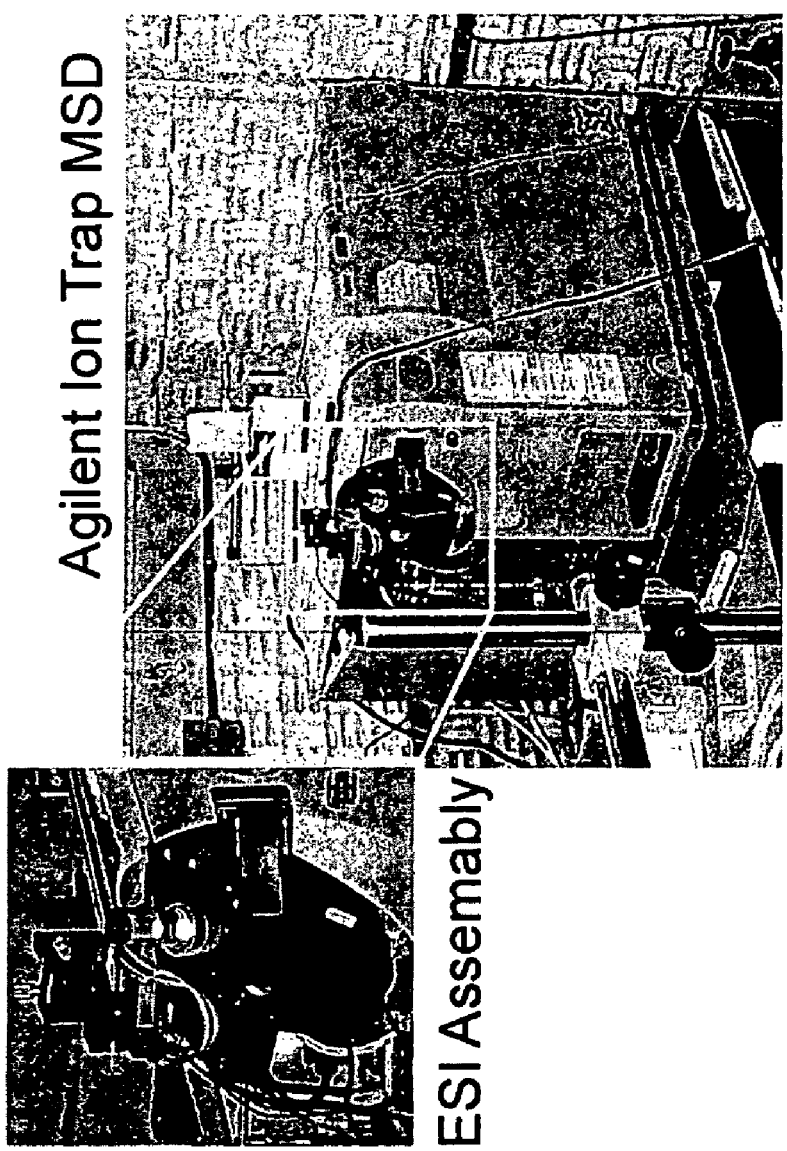
FIG. 24 illustrates a testing jig mounted inside ESI assembly of Agilent Ion Trap MSD.

For chip LC analyses, the completed chip assembly was attached to the end of a probe mounted on a three dimensional positioner. This entire assembly was bolted onto the pre-existing Agilent electrospray ion source housing. The setup is such that the chip electrospray needle is in the same position as the standard electrospray needle, orthogonal to axis of the MS inlet (FIG. 23). Electrolysis pumps on the chip were galvanostatically controlled using output currents from custom-built voltage to current converters. Control of these current sources was achieved using LabView and a DAQPad-6020E interface board from National Instruments (Austin, Tex.). Separations were done at a flow rate of 80 nL/min with gradients going from 5 to 60% organic solvent (0.1% formic acid in methanol) over 40 minutes. In these experiments, about 600 fmol of BSA digest were injected onto the column.

Results and Discussion

Device Fabrication and Assembly. One of the guiding principals of this work to develop microfluidic sample preparation systems for mass spectrometry is to utilize fabrication techniques that can be adapted to mass production. Parylene surface micromachining technology allowed to batch fabricate (FIG. 20) the micro-scale LC system using standard lithographic processes on a silicon wafer. Parylene exhibits high strength, chemical inertness, optical transparency, and can be deposited as a conformal film at room temperature. These properties make Parylene an ideal material from both an application and fabrication standpoint.

Each fabricated chip contains two solvent pumps and a sample pump. Each of these pumps consists of a pair of electrodes that are used for electrochemical pumping. The chips also integrate a mixer, an LC column, and a free standing electrospray needle extending 1 mm past the edge of the chip (FIG. 19) (ref. 24).

Electrochemical Pumps. The electrolysis-based pumps (ref. 24) are capable of producing the flow rates and pressures required for an LC separation. The pumps are controlled galvanostatically and typical currents used during operation of the chip range from 0 to 400 μA. Pumping efficiencies of up to 10% can be achieved and the total power consumption of all three pumps together was generally around 2 mW during a typical separation. Here pumping efficiency is defined as the ratio between how much liquid has been pumped out and the theoretical volume of gas that should have been generated. These losses can be attributed to factors such as chemical reactions other than hydrolysis; recombination of the hydrogen and oxygen; gas dissolution in the solvent; and gas leaking out of the reservoir.

With a decision to utilize an electrochemical pump, a concern can arise that dissolved gas in the solvents can result in gas bubble formation at the end of the column. The solvent stream between the end of the column and the electrospray needle can be carefully monitored; bubble formation has not been observed during separations. This is most likely because the solvent chambers are large enough that the gas generated over the electrodes (in the rear of the chamber) does not affect the solvent at the front of the chamber (near the outlet to the mixer and the column) within the duration of a typical separation (<1 hour).

Static Mixer. The design of the static mixer relies on diffusion to achieve uniform mixing of the solvent gradient. Rapid mixing is achieved using a channel that has a 20 μm×20 μm cross sectional area and a length of 2 mm. This small cross section effectively reduces the necessary diffusion lengths required for complete mixing and is able to provide adequate mixing at flow rates as high as 120 nL/min. The total volume of the mixer is approximately 1.5 nL and the expected pressure drop is <1 psi. Thus, the effect of the mixer on both the system back pressure and the delay in the start of the gradient is negligible.

Reverse Phase Column. The on-chip column is 1.2 cm long and rectangular in shape (20 μm×100 μm). When strengthened with the SU8 layer, it is able to withstand pressures higher than 250 psi for extended periods of time. The flow resistance for a 1.2 cm column and 3 um packed beads and normalized to a 1 cP liquid is 1.34 psi/(nL/min).

Electrospray Nozzle. Details of the fabrication and performance of the Parylene electrospray nozzle have been described previously (Ref. 24). The nozzle on this particular chip has a tip opening of approximately 5 μm×20 μm. Stable electrospray was achieved over a wide range of flow rates, from as low as 50 nL/min to 1000 nL/min. Typical potentials needed to achieve electrospray are generally around 2000 V.

Gradient Formation. For a two pump gradient system with almost no flow resistance, the solvent composition varies nearly linearly with current at each pump chamber, see e.g. Xie, J.; Miao, Y.; Shih, J.; He, Q.; Liu, J.; Tai, Y. C.; Lee, T. D. *Anal Chem* 2004, 76, 3756-3763, incorporated herein by reference in its entirety. For a system operating at higher pressure, due to the flow resistance of a packed column, the situation is more complex. A flow resistance is needed between the pump chambers and the mixer, otherwise there can be only a very narrow range of pressures for which one can achieve confluent flow (liquid flow from both chambers through the column) and there is a high possibility of liquid flowing directly from one chamber to the other. Even if one is able to achieve confluent flow, minute pressure changes in the solvent reservoirs can cause large shifts in the composition of liquid flowing into the column, significantly affecting the quality of the gradient formed. In the chip LC, the channels (4 mm in length) between the pump and mixer were packed with 3 μm chromatography support to provide the flow resistance.

Figure 31:
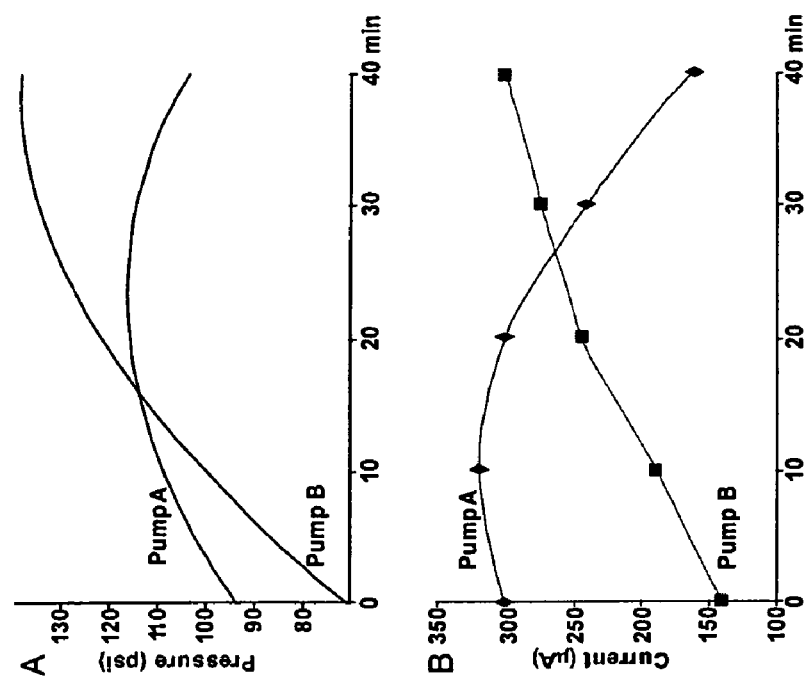
FIG. 31 shows A) Calculated pressure curves for each pump chamber that will yield a linear solvent gradient (80 nL/min, 5 to 60% methanol) through the chromatography column. B) Corresponding current calibration curves with a 2 µL initial gas volume in the aqueous pump chamber (5% methanol) and a 1 µL gas volume in the organic pump chamber (60% methanol).

By considering the flow resistance of the packed side channels and the column, and the viscosity of the solvent streams, it is possible calculate the pressure needed in each chamber, as a function of time, to create a linear gradient (FIG. 31A). By integrating the desired linear flow rate profile, one can also determine the corresponding gas volume in each chamber as a function of time, since the volume of gas in each chamber is identical to the volume of fluid that has been pumped out. The number of molecules of gas in the chamber as a function of time can be calculated using the ideal gas law. This ultimately yields the net molecular gas generation rate that is required to achieve the desired linear gradient. The net gas generation rate has to be considered (as opposed to just the gas generation rate) because of possible losses caused by gas recombination or leakage through the gasket. The currents needed to provide the calculated net gas generation rates are then determined empirically using a setup that simulates actual run conditions The calibration setup utilizes a pump and reservoir identical to those on the chip LC except that flow out the chamber is through a fused silica capillary coupled to a regulated gas pressure source at the other end. Flow rates were calculated by measuring the speed of the liquid front in the capillary and the necessary current profiles with respect to time were determined (FIG. 31B). The principal disadvantage of this approach is that the calibration assumes an initial gas volume in each pump, thus run to run reproducibility of the gradient is limited by the ability to achieve the proper initial conditions. Feedback from either flow or pressure sensors can provide more precise control of the gradient, but the present setup was sufficient to demonstrate the feasibility of performing adequate LC separations using a microfluidic device.

Figure 26:
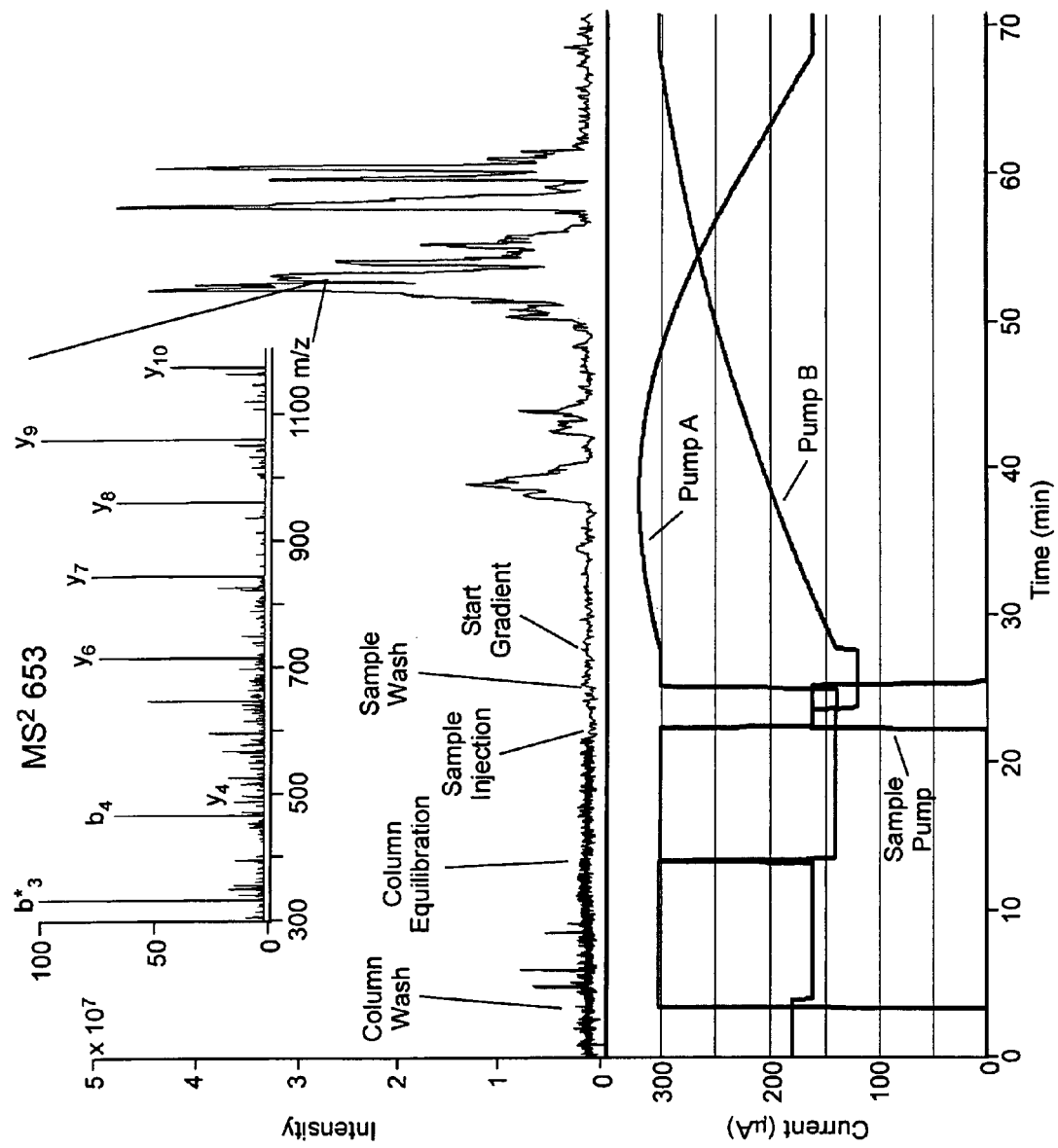
FIG. 26 shows, on lower panel: a current control sequence for gradient elution, on upper panel: LC separation of trypsin digested bovine serum albumin performed using this current control sequence, and on inset, corresponding MS/MS spectra.

LC/MS/MS Analysis of a Peptide Mixture. The typical cycle for an LC separation of a peptide mixture includes steps for a column wash, re-equilibration to initial conditions, sample loading, sample wash to remove polar contaminants, and finally gradient elution of the separated components. On the chip LC, these operations are performed in sequence by controlling the current to the electrodes for each of the pump chambers. A typical program for the current control is shown in FIG. 26 (lower panel). Pump A (95/5/0.1 water/methanol/formic acid) is started first to pressurize the system. Pump B (40/60/0.1 water/methanol/formic acid) is then turned on to wash the column, and after approximately 10 min (~100 nL/min), the current to Pump B is lowered and that of Pump A is raised to re-equilibrate the column. After several minutes, the current to Pump A is lowered and the sample pump is turned on to pump the sample solution onto the column. After approximately 600 nL of the 1 pmol/μL BSA sample is loaded, the sample pump is turned completely off and current to Pump A is increased to wash the sample on the column. During this step, the sample pump chamber was allowed to refill with aqueous solvent from Pump A. This mitigates any effect that the gas bubble in the sample pump chamber would have on flow into the mixer from the two solvent pumps during gradient formation. Finally, the currents to both pumps A and B were varied to yield a linear gradient as defined by the calibration (FIG. 31B). The time for the entire cycle from the beginning of the column wash to the end of the gradient was 65 min with the gradient elution occupying the final 40 min.

Figure 32:
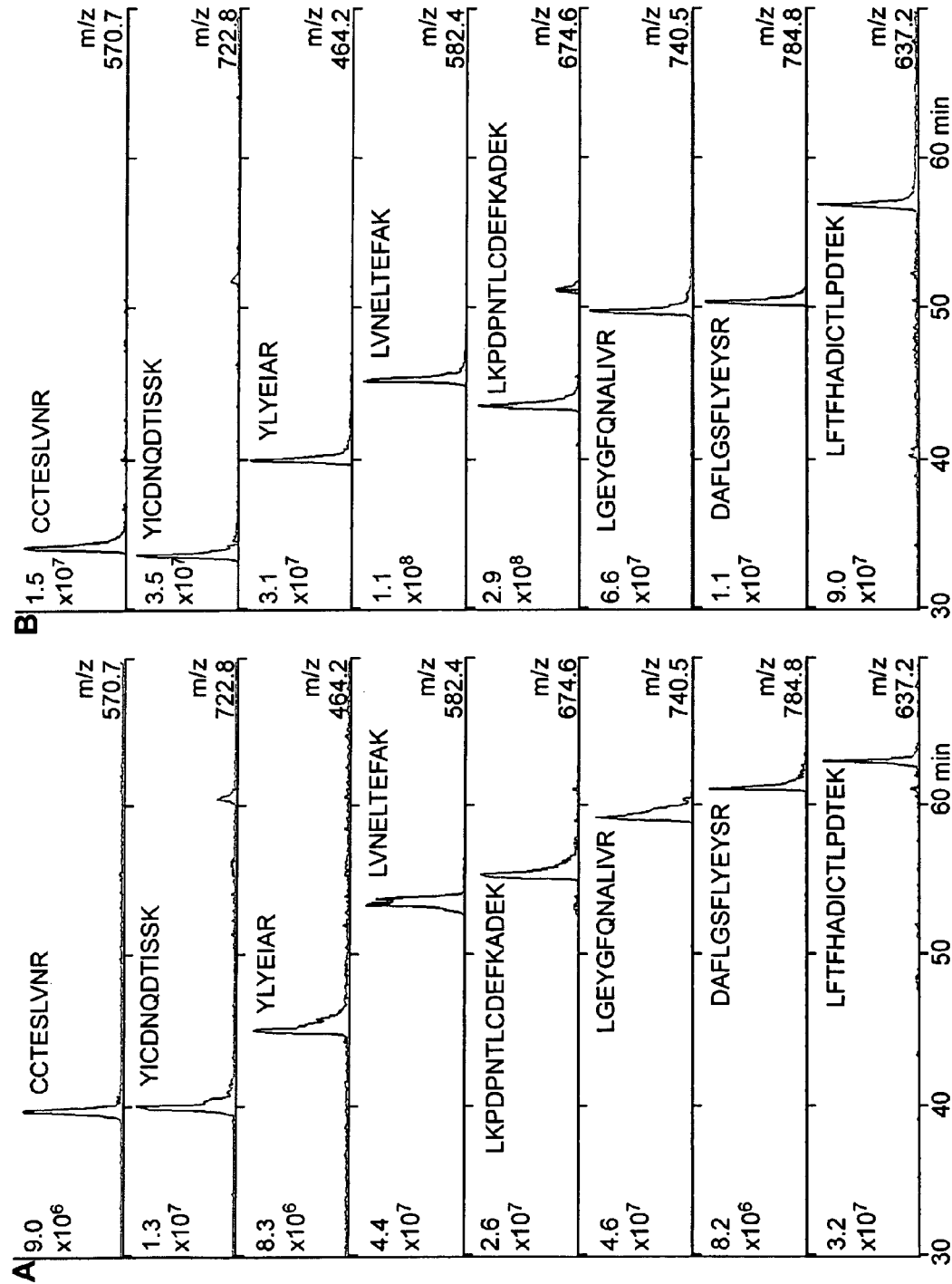
FIG. 32 presents separation comparison between the commercial system and the microfluidic system for on-chip LC-ESI.

The mixture of peptides obtained by trypsin digestion of BSA was used to evaluate the performance of the chip LC. For the run shown (FIG. 26, upper panel), both MS and MS/MS spectra (FIG. 26 inset) were collected for those ions that exceeded a preset threshold in the full mass range spectrum. The results obtained can be compared to those obtained analyzing the same sample using the Agilent 1100 series nanoflow pump (FIG. 32). The peak shape and chromatographic resolution are somewhat better for the Agilent LC separation, but this is to be expected given the differences between the two columns. The separation using the Agilent HPLC utilized a 75 um ID column 10 cm long packed with 3.5 μm C18 reverse phase media (Zorbax 300 SB-$C_{18}$). The cross sectional area of the column on the chip LC is equivalent to 50 μm ID, is only 1.2 cm long, and is packed with a different 3 μm C18 reverse phase media (3 μm Varian Polaris $C_{18}$). There were also some differences observed in peptide elution order, likely due to the difference in supports and the column temperature. The region where the chip is mounted is warmed by the electrospray interface, whereas the Agilent column was mounted outside the source. Also, because this prototype lacked sensors for the feedback control of the pump, the gradient formation on the chip is not as precise as that created by the Agilent pump.

Fragment ion spectra (MS/MS spectra) were collected for each analysis. When searched against the protein database, the run done on the Agilent LC gave 60% sequence coverage for BSA. The sequence coverage for the run done on the chip LC gave 53% sequence coverage. The primary difference was the failure to observe some of the more hydrophobic peptides that elute late in the gradient. The 60% organic solvent composition used in this experiment may not be sufficient to elute the more hydrophobic peptides from the Varian support. It should be noted that although the timescale of the two chromatographic runs appears to be comparable, for the separation using the Agilent HPLC, the gradient started at 2 min, whereas for the separation on the chip LC, the gradient started at 28 min. If one compares the delay between the start of the gradient formation and the time that it arrives at the end of the column, one sees that the delay in our chip LC is much smaller, and difference would have been even greater if the Agilent HPLC had been operating at the same flow rate (80 nL/min vs. 300 nL/min). This illustrates the time advantage that can be achieved by having pumps mounted directly on the chip. There is no longer the delay due to the volume of the components between the mixing tee and the head of the column.

Conclusions

The results obtained for the chip LC demonstrate the feasibility of using a microfluidic device to perform reverse phase separations of complex peptide mixtures. The device integrates a nanoflow electrochemical gradient pump, sample loading pump, nL scale static mixer, packed C18 column, and electrospray nozzle. The separation and on-line MS analysis of a complex peptide mixture yields results that are close to what can be achieved using a state-of-the-art nanoflow HPLC system. Placing the pumps directly on the chip dramatically shortens the total cycle time for an LC run.

The following references can be used by one skilled in the art for practicing of the various embodiments described herein and for background as needed, including references 1-22, and all of references are incorporated by reference in their entirety.

(1) Lion, N.; Rohner, T. C.; Dayon, L.; Arnaud, I. L.; Damoc, E.; Youhnovski, N.; Wu, Z. Y.; Roussel, C.; Josserand, J.; Jensen, H.; Rossier, J. S.; Przybylski, M.; Girault, H. H. *Electrophoresis* 2003, 24, 3533-3562.

(2) Jacobson, S. C.; Hergenroder, R.; Koutny, L. B.; Ramsey, J. M. *Anal Chem* 1994, 66, 1114-1118.

(3) Lacher, N. A.; de Rooij, N. F.; Verpoorte, E.; Lunte, S. M. *J Chromatogr A* 2003, 1004, 225-235.

(4) Liu, Y.; Foote, R. S.; Jacobson, S. C.; Ramsey, R. S.; Ramsey, J. M. *Anal Chem* 2000, 72, 4608-4613.

(5) Hofmann, O.; Che, D.; Cruickshank, K. A.; Muller, U. R. *Anal Chem* 1999, 71, 678-686.

(6) Tan, W.; Fan, Z. H.; Qiu, C. X.; Ricco, A. J.; Gibbons, I. *Electrophoresis* 2002, 23, 3638-3645.

(7) Li, Y.; DeVoe, D. L.; Lee, C. S. *Electrophoresis* 2003, 24, 193-199.

(8) Tsai, S. W.; Loughran, M.; Hiratsuka, A.; Yano, K.; Karube, I. *Analyst* 2003, 128, 237-244.
(9) Herr, A. E.; Molho, J. I.; Drouvalakis, K. A.; Mikkelsen, J. C.; Utz, P. J.; Santiago, J. G.; Kenny, T. W. *Anal Chem* 2003, 75, 1180-1187.
(10) Kutter, J. P.; Jacobson, S. D.; Ramsey, J. M. *Anal Chem* 1997, 69, 5165-5171.
(11) Culbertson, C. T.; Jacobson, S. C.; Ramsey, J. M. *Anal Chem* 2000, 72, 5814-5819.
(12) Ramsey, J. D.; Jacobson, S. C.; Culbertson, C. T.; Ramsey, J. M. *Anal Chem* 2003, 75, 3758-3764.
(13) Rocklin, R. D.; Ramsey, R. S.; Ramsey, J. M. *Anal Chem* 2000, 72, 5244-5249.
(14) Slentz, B. E.; Penner, N. A.; Regnier, F. E. *J Chromatogr A* 2002, 948, 225-233.
(15) Svec, F.; Peters, E. C.; Sykora, D.; Frechet, J. M. *J Chromatogr A* 2000, 887, 3-29.
(16) Throckmorton, D. J.; Shepodd, T. J.; Singh, A. K. *Anal Chem* 2002, 74, 784-789.
(17) He, B.; Regnier, F. *J Pharm Biomed Anal* 1998, 17, 925-932.
(18) Li, J.; LeRiche, T.; Tremblay, T. L.; Wang, C.; Bonneil, E.; Harrison, D. J.; Thibault, P. *Mol Cell Proteomics* 2002, 1, 157-168.
(19) Ekstrom, S.; Malmstrom, J.; Wallman, L.; Lofgren, M.; Nilsson, J.; Laurell, T.; Marko-Varga, G. *Proteomics* 2002, 2, 413-421.
(20) Gottschlich, N.; Jacobson, S. C.; Culbertson, C. T.; Ramsey, J. M. *Anal Chem* 2001, 73, 2669-2674.
(21) Fortier, M. H.; Bonneil, E.; Goodley, P.; Thibault, P. *Anal Chem* 2005, 77, 1631-1640.
(22) Xie, J.; Miao, Y.; Shih, J.; He, Q.; Liu, J.; Tai, Y. C.; Lee, T. D. *Anal Chem* 2004, 76, 3756-3763.
(23) Xie, J.; Shih, J.; Lin, Q.; Yang, B.; Tai, Y. C. *Lab Chip* 2004, 4, 495-501.
(24) Licklider, L.; Wang, X.-Q.; Desai, A.; Tai, Y.-C.; Lee, T. D. *Anal. Chem.* 2000, 72, 367-375.
(25) Ho, C.-M.; Tai, Y.-C. *Annu. Rev. Fluid Mech.* 1998, 30, 579-612.

What is claimed is:

1. A microfluidic system for liquid chromatography comprising:
    (A) a main chip comprising a front surface and a back surface, the main chip further comprising:
    a substrate having a front face and a back face;
    a chromatography column on the front face of said substrate, wherein said column has an inlet and an outlet;
    at least one pump system on the front face of said substrate comprising a pump chamber, at least one electrode, and an outlet microfluidically coupled to the inlet of said column,
    wherein said electrode is part of a set of interdigitated electrodes and at least a portion of said electrode is internal to the pump chamber;
    (B) a reservoir chip comprising a front surface and a back surface, wherein the reservoir chip has at least one cavity in the back surface which when disposed next to the front surface of the main chip extends the volume of the pump chamber.

2. The microfluidic system of claim 1, wherein the system further comprises at least one electrospray ionization (ESI) nozzle on the front face of said substrate, wherein said nozzle has an inlet and an outlet, and wherein the inlet of the nozzle is microfluidically coupled to the outlet of the column.

3. The microfluidic system of claim 1, further comprising a sealing element disposed between the back surface of the reservoir chip and the front surface of the main chip.

4. The microfluidic system of claim 2, wherein the sealing element is a gasket layer comprising a polymer material.

5. The microfluidic system of claim 1, further comprising a cover disposed next to the front surface of the reservoir chip.

6. The microfluidic system of claim 5, further comprising a sealing element disposed between the front surface of the reservoir chip and the cover.

7. The microfluidic system of claim 1, further comprising:
    a first sealing element disposed between the back surface of the reservoir chip and the front surface of the main chip;
    a cover disposed next to the front surface of the reservoir chip; and
    a second sealing element disposed between the front surface of the reservoir chip and the cover.

8. The microfluidic system of claim 1, wherein the reservoir chip further comprises at least one inlet and at least one outlet which are in fluid communication with the cavity.

9. The microfluidic system of claim 1, wherein the main chip further comprises a planarizing layer.

10. The microfluidic system of claim 1, wherein a spacing between the interdigitated electrodes approximately equals a width of the interdigitated electrodes.

11. The microfluidic system of claim 1, wherein a spacing between the interdigitated electrodes is from about 5 microns to about 200 microns.

12. The microfluidic system of claim 1, wherein the pump system is fluidically coupled to the column through a fluidic network.

13. A microfluidic system for liquid chromatography/electrospray ionization mass spectrometry comprising:
    (A) a main chip comprising a front surface and a back surface, the main chip further comprising:
    a substrate having a front face and a back face;
    at least one electrochemical pump system integrated on the front face of said substrate comprising a pump chamber, at least one electrode, and an outlet,
    wherein said electrode is part of a set of interdigitated electrodes and at least a portion of said electrode is internal to the pump chamber;
    a chromatography column integrated on the front face of said substrate, wherein said column has an inlet and an outlet, and the inlet of said column is microfluidically coupled to the pump outlet;
    a fluidic network integrated on the front face of the substrate to fluidically couple the pump and the column;
    at least one electrospray ionization (ESI) nozzle integrated on the front face of said substrate, wherein said nozzle has an inlet and an outlet, and wherein the inlet of the nozzle is microfluidically coupled to the outlet of the column;
    (B) a reservoir chip comprising a front surface and a back surface, wherein the reservoir chip has at least one cavity in the back surface which when disposed next to the front surface of the main chip extends the volume of the pump chamber, and wherein the reservoir chip further comprises at least one inlet and at least one outlet which are in fluid communication with the cavity;
    and further comprising:
    a first sealing element disposed between the back surface of the reservoir chip and the front surface of the main chip;
    a cover disposed next to the front surface of the reservoir chip; and
    a second sealing element disposed between the front surface of the reservoir chip and the cover.

* * * * *